(12) United States Patent
Conley et al.

(10) Patent No.: US 11,986,302 B2
(45) Date of Patent: May 21, 2024

(54) URINE COLLECTION SYSTEMS AND ASSOCIATED METHODS AND DEVICES

(71) Applicant: REPRIEVE CARDIOVASCULAR, INC., Milford, MA (US)

(72) Inventors: Eric Conley, York, ME (US); Andrew Victor Halpert, Brookline, MA (US); Kenneth John Luppi, Tewksbury, MA (US); Antony Jonathan Fields, San Francisco, CA (US)

(73) Assignee: Reprieve Cardiovascular, Inc., Milford, MA (US)

( * ) Notice: Subject to any disclaimer, the term of this patent is extended or adjusted under 35 U.S.C. 154(b) by 0 days.

(21) Appl. No.: 18/193,508

(22) Filed: Mar. 30, 2023

(65) Prior Publication Data
US 2023/0233124 A1 Jul. 27, 2023

Related U.S. Application Data

(63) Continuation of application No. 17/805,897, filed on Jun. 8, 2022, now Pat. No. 11,633,137, which is a
(Continued)

(51) Int. Cl.
*A61B 5/20* (2006.01)
*A61F 5/44* (2006.01)
*A61M 1/00* (2006.01)

(52) U.S. Cl.
CPC ............ *A61B 5/208* (2013.01); *A61F 5/4405* (2013.01); *A61M 1/74* (2021.05); *A61M 1/80* (2021.05);
(Continued)

(58) Field of Classification Search
CPC .......... A61B 10/007; A61B 2560/0276; A61B 5/208; A61M 2205/3396;
(Continued)

(56) References Cited

U.S. PATENT DOCUMENTS 4,411,649 A 10/1983 Kamen
5,179,862 A * 1/1993 Lynnworth ............. G01F 1/662
73/861.28
(Continued)

FOREIGN PATENT DOCUMENTS

WO 2019222485 A2 10/2020

OTHER PUBLICATIONS

International Search Report and Written Opinion dated Jul. 5, 2022; International Patent Application No. PCT/US2022/071742; 16 pages.
(Continued)

*Primary Examiner* — Adam Marcetich
(74) *Attorney, Agent, or Firm* — Perkins Coie LLP

(57) ABSTRACT

Urine collection systems and associated methods and devices are disclosed herein. A representative system can include a urine collection device, a flow control assembly configured to direct a urine flow from the patient to the urine collection device, and a urine measurement device including a first sensor and a second sensor. The first sensor is configured to generate first sensor data based on a weight of the container, and the second sensor is configured to generate second sensor data based on the urine flow from the patient to the container. The system can further include non-transitory computer readable media having instructions that, when executed by one or more processors, cause the system to perform operations comprising determining a first patient urine output based on the first sensor data; and determining a second patient urine output based on the second sensor data.

19 Claims, 31 Drawing Sheets

Related U.S. Application Data continuation of application No. 17/659,393, filed on Apr. 15, 2022.

(60) Provisional application No. 63/220,873, filed on Jul. 12, 2021, provisional application No. 63/175,380, filed on Apr. 15, 2021.

(52) U.S. Cl.
CPC ............... *A61M 2205/3396* (2013.01); *A61M 2230/005* (2013.01)

(58) Field of Classification Search
CPC .... A61M 2210/1089; A61M 2230/005; A61M 5/142; A61M 5/1723; A61M 2205/3393; A61M 2205/3334; A61M 2205/50; A61M 1/777; A61M 5/16895; A61M 3/022; A61M 5/16845; A61M 2202/0496; A61M 2205/3331; A61M 1/342; A61M 2210/1085; A61M 25/0017

See application file for complete search history.

(56) References Cited

U.S. PATENT DOCUMENTS

| | | | |
|---|---|---|---|
| 5,586,973 A | 12/1996 | Lemaire et al. | |
| 5,709,670 A | 1/1998 | Vancaillie et al. | |
| 7,739,921 B1* | 6/2010 | Babcock | G01F 1/34 73/252 |
| 8,714,030 B1* | 5/2014 | Liu | G01F 1/662 73/861.28 |
| 11,633,137 B2 | 4/2023 | Conley et al. | |
| 2001/0029340 A1* | 10/2001 | Mault | A61B 5/742 600/531 |
| 2003/0040700 A1* | 2/2003 | Hickle | A61M 39/281 604/890.1 |
| 2006/0100743 A1* | 5/2006 | Townsend | A61B 5/412 700/266 |
| 2006/0235353 A1 | 10/2006 | Gelfand et al. | |
| 2006/0270971 A1 | 11/2006 | Gelfand et al. | |
| 2007/0088333 A1 | 11/2007 | Levin et al. | |
| 2011/0046514 A1* | 2/2011 | Greenwald | G01F 1/662 702/45 |
| 2011/0120231 A1* | 5/2011 | Berger | G01F 1/667 73/861.18 |
| 2011/0288524 A1 | 11/2011 | Gelfand et al. | |
| 2013/0104667 A1* | 5/2013 | Koyano | G01F 1/662 73/861.25 |
| 2013/0235691 A1 | 9/2013 | Volker | |
| 2014/0260600 A1* | 9/2014 | Rike | G01F 23/261 73/290 R |
| 2014/0366641 A1* | 12/2014 | Jedema | G01F 1/56 73/861.12 |
| 2015/0105694 A1 | 4/2015 | Mahajan | |
| 2015/0233749 A1 | 8/2015 | Wang et al. | |
| 2016/0051176 A1 | 2/2016 | Ramos et al. | |
| 2016/0051750 A1* | 2/2016 | Tsoukalis | A61M 5/16813 235/375 |
| 2016/0136356 A1* | 5/2016 | Ribble | A61B 5/14552 705/2 |
| 2017/0016755 A1 | 1/2017 | Boussange et al. | |
| 2017/0052056 A1 | 2/2017 | Yamasaki et al. | |
| 2017/0290974 A1* | 10/2017 | Tsoukalis | A61M 5/1407 |
| 2018/0085510 A1 | 3/2018 | Halpert et al. | |
| 2018/0177945 A1 | 6/2018 | Sims et al. | |
| 2018/0245967 A1 | 8/2018 | Parker et al. | |
| 2019/0001057 A1 | 1/2019 | Tsoukalis | |
| 2019/0038833 A1 | 2/2019 | Pirazzoli et al. | |
| 2019/0262532 A1 | 8/2019 | Oh et al. | |
| 2020/0324044 A1 | 10/2020 | Gylland et al. | |
| 2020/0360604 A1* | 11/2020 | Kolko | G01G 3/14 |
| 2020/0384234 A1* | 12/2020 | Niland | A61M 16/109 |
| 2020/0405955 A1 | 12/2020 | Shah et al. | |
| 2021/0077007 A1 | 3/2021 | Jouret et al. | |
| 2021/0085853 A1 | 3/2021 | Chen et al. | |
| 2021/0128815 A1 | 5/2021 | Byrne et al. | |
| 2021/0196880 A1 | 7/2021 | O'Mahony et al. | |
| 2021/0236727 A1* | 8/2021 | Levin | A61M 5/16804 |
| 2021/0260306 A1* | 8/2021 | Gravenstein | F24H 9/2014 |
| 2021/0283357 A1* | 9/2021 | Leonard | A61M 16/204 |
| 2021/0298653 A1* | 9/2021 | Woodard | A61B 5/746 |
| 2021/0369959 A1* | 12/2021 | Abal | A61M 5/1411 |
| 2022/0288362 A1* | 9/2022 | Porter | A61B 5/0031 |
| 2022/0296406 A1* | 9/2022 | Keelen | A61B 5/208 |

OTHER PUBLICATIONS

Non-Final Office Action dated Aug. 17, 2022; U.S. Appl. No. 17/805,897; 32 pages.

Notice of Allowance dated Dec. 14, 2022; U.S. Appl. No. 17/805,897; 15 pages.

* cited by examiner

URINE COLLECTION SYSTEMS AND ASSOCIATED METHODS AND DEVICES

CROSS-REFERENCE TO RELATED APPLICATIONS

The present application is related to U.S. patent application Ser. No. 17/112,925, filed Dec. 4, 2020, and is a continuation of U.S. patent application Ser. No. 17/805,897, filed Jun. 8, 2022, which is a continuation of U.S. patent application Ser. No. 17/659,393, filed Apr. 15, 2022, which claims the benefit of priority to U.S. Provisional Patent Application No. 63/220,873, filed Jul. 12, 2021, and U.S. Provisional Patent Application No. 63/175,380, filed Apr. 15, 2021, the disclosures of which are each incorporated herein by reference in their entireties.

TECHNICAL FIELD

The present disclosure generally relates to medical devices and, in particular, to systems for urine collection and associated methods and devices.

BACKGROUND

Human physiological systems seek to naturally maintain a balance between fluid intake and fluid excretion. An imbalance in fluid intake and excretion rates may cause the body to retain excess amounts of fluid, also known as fluid overload. Fluid overload can be caused by acute decompensated heart failure (ADHF), chronic heart failure (CHF), or other conditions in which insufficient fluid is excreted. Patients exhibiting fluid overload may suffer from shortness of breath (dyspnea), edema, hypertension, and other undesirable medical conditions.

To treat fluid overload, patients are typically administered a diuretic drug which induces and/or increases urine production, thus reducing the amount of fluid and sodium in the body. The rate of urine output may be carefully monitored and/or controlled for safety reasons, e.g., to avoid placing undue stress on the patient's kidneys. Different patients may respond differently to treatment, such that the same diuretic type and/or dosage may produce drastically different urine output rates. However, conventional systems and methods for treating fluid overload may not be capable of accurately monitoring a patient's urine output and/or responding to changes in urine output. Additionally, conventional treatment systems and devices may not be capable of accommodating high urine production rates, and thus may require a nurse or other healthcare professional to empty and/or replace urine collection bags multiple times during the treatment procedure. Conventional systems and devices may also be prone to air lock and/or interruptions to urine flow.

BRIEF DESCRIPTION OF THE DRAWINGS

Features, aspects, and advantages of the presently disclosed technology may be better understood with regard to the following drawings.

Figure 1A:
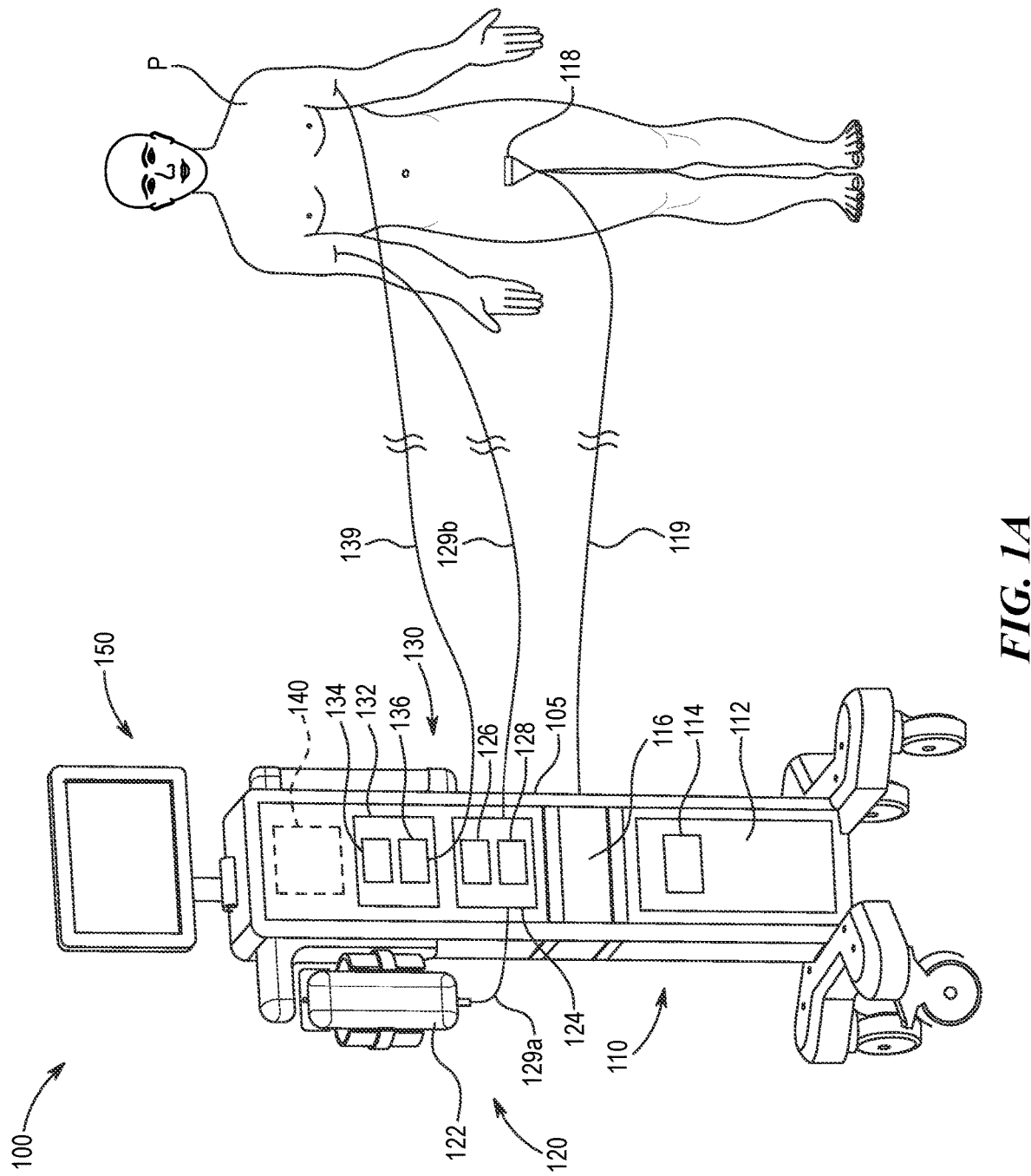
FIGS. 1A-1D are partially schematic views of fluid management systems, in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

The present technology is directed to systems for collecting and/or monitoring a patient's urine output, and associated methods and devices. In some embodiments, a urine collection system includes a first container and a second container configured to hold urine from a patient. The system can also include at least one sensor configured to generate sensor data indicative of an amount of urine in the first and/or second containers. The system can further include a flow control assembly configured to direct a urine flow from the patient into the first container or the second container, based on the sensor data. For example, the flow control assembly can include a set of valves and/or other fluid control elements to selectively direct urine flow into the first container and/or the second container. If the flow control assembly detects that one of the containers is full or nearly full, the flow control assembly can automatically redirect the urine flow into the other container. This approach can be advantageous for medical procedures in which the patient produces large volumes of urine, such as procedures for treating the patient for fluid overload by administering diuretics. For example, the present technology can reduce the number of times a user (e.g., a nurse or other healthcare professional) needs to check on and/or empty the containers. The present technology can also make it easier for the user to remove and empty the urine containers, thus reducing the likelihood of leaks or spills.

In some embodiments, a fluid therapy system and/or urine collection system includes a container, a flow control assembly configured to direct a urine flow from the patient to the container, and a urine measurement device or system including a first sensor and a second sensor. The first sensor is configured to generate first sensor data based on a weight of the container, and the second sensor is configured to generate second sensor data based on the urine flow from the patient to the container. The first and second sensor data can be used to generate first and second patient urine outputs (e.g., average urine flow rates and/or urine volume over a period of time), respectively. The system can utilize each of the first and second patient urine outputs as a primary source for determining amounts of diuretic and/or hydration fluid to be provided to the patient. For example, in some embodiments the first patient urine output (e.g., based on a changing weight of the container) is used as the primary source, unless the system detects the weight of the container is decreasing, which likely indicates the container is being drained. When the system detects the weight of the container is decreasing, the second patient urine output (based on flow of the container) can be used as the primary source. As explained herein, this approach advantageously enables an accurate and reliable urine output rate to be determined even when the container is being drained. As such, embodiments of the present technology enable continuous fluid therapy with limited risk of interruption. Additionally or alternatively, embodiments of the present technology can also enable healthcare professionals (e.g., nursing aids) who are permitted to interact with containers, but are not permitted to operate medical equipment, to drain the container without using the user interface of the system.

The present technology also provides devices and associated methods suitable for use in combination with a urine collection system. In some embodiments, for example, a device for collecting urine from a patient includes a first fluid line configured to couple to the patient's body, a second fluid line configured to couple to a urine container, and a hollow member (e.g., a flexible bulb) fluidly coupling the first and second fluid lines. The hollow member can have a first end portion coupled to the first fluid line, a second end portion coupled to the second fluid line, and a flexible body portion fluidly coupling the first and second end portions. The first and second end portions can each include a respective check valve allowing fluid flow from the patient's body to the urine container, while restricting or preventing fluid flow in the opposite direction. In some embodiments, the flexible body portion is configured to be repeatedly actuated (e.g., compressed) to draw fluid from the patient's body into one or more of the first or second fluid lines. The actuation of the flexible body portion can prime the fluid lines with a fluid (e.g., saline and/or urine) and/or remove air from the fluid lines (e.g., by moving the air into the urine container). Accordingly, the device can maintain a generally continuous urine flow from the patient's body to the urine container, which may be beneficial for fluid removal procedures and/or accurate monitoring of the patient's urine output. The device can also provide a convenient way to prime urine flow and/or remove obstructions (e.g., air locks) from the fluid line while maintaining sterility, thus reducing the likelihood of urinary tract infections and/or other complications.

The headings provided herein are for convenience only and are not intended to limit or interpret the scope or meaning of the technology.

I. FLUID MANAGEMENT SYSTEMS AND METHODS

The present technology is generally directed to systems, devices, and associated methods for managing fluid levels of a patient. In some embodiments, the systems, devices, and methods described herein are used to treat a patient for fluid overload. To treat fluid overload, patients can be administered a diuretic drug which induces and/or increases urine production. For example, loop diuretics are diuretics that act at the ascending limb of the loop of Henle in the kidney, and include bumetanide (Bumex®), ethacrynic acid (Edecrin®), furosemide (Lasix®), torsemide (Demadex®), thiazide diuretics (e.g., chlorothiazide, metolazone), potassium-sparing diuretics (e.g., amiloride, spironolactone), carbonic anhydrase inhibitors (e.g., acetazolamide), and osmotic diuretics (e.g., mannitol). Diuretics can be given orally as a pill or as an intravenous (IV) injection. IV diuretics can be used when oral diuretics are no longer effective and/or able to be absorbed.

The short-term effects of diuretics on a patient's urine production may be difficult to predict, particularly at early stages of treatment. For example, one patient may produce much less urine than expected for a given dose of diuretic, while another patient administered the same dose may produce very large amounts of urine. Low urine production can prolong treatment time and/or reduce treatment efficacy, while high urine production can raise concerns of hypotension, hypovolemia, electrolyte imbalance (e.g., hypokalemia), and/or vital organ damage. High doses of a diuretic, regardless of the urine response, can also raise concerns about ototoxicity. Due to these uncertainties, physicians typically initially prescribe a conservative (e.g., low) diuretic dosage and wait a few hours before considering whether to increase the dosage. If the physician determines that a higher diuretic dosage is needed, the physician may slowly and incrementally increase the dosage until the patient's urine output reaches the desired level and/or rate. However, this approach can prolong the time the patient remains in the fluid overloaded condition, which can exacerbate the patient's underlying clinical state. For example, conservative treatment procedures can require hours or even days before the patient's urine output is sufficiently high to cause significant fluid loss and relieve the fluid overload condition. The patient may be hospitalized for several days (e.g., 4-5 days), which can be expensive and burdensome. Additionally, the long-term treatment efficacy may be limited, such that approximately 25% of patients are readmitted for fluid overload within 30 days.

To overcome these and other challenges, the present technology provides systems, and associated devices and methods, for managing a patient's fluid levels. In some embodiments, the present technology can (i) improve efficacy, safety, and quality of fluid management treatment, (ii) improve resource management in hospitals and other clinical settings, (iii) quickly assess if a patient is diuretic resistant, and/or (iv) increase diuretic efficiency (the amount of urine and/or excreted electrolytes (e.g., sodium) obtained over a given time per mg of diuretic infused intravenously). The embodiments described herein can increase net removal of fluid and/or electrolytes (e.g., sodium and/or chloride), and can also treat fluid overload conditions in a more efficient manner (e.g., shorter timeframe and/or higher net fluid loss).

FIG. 1A is a partially schematic illustration of a fluid management system 100 ("system 100") for monitoring urine output and/or control fluid infusion into a patient P, in accordance with embodiments of the present technology.

The system 100 includes a urine collection and monitoring system 110 ("urine system 110"), an automated hydration fluid infusion system 120 ("hydration system 120"), an automated diuretic infusion system 130 ("diuretic system 130"), a controller or control system 140 ("controller 140"), and a display or input/output unit 150 ("display 150"). The controller 140 can be operably coupled to each of the urine system 110, hydration system 120, diuretic system 130, and/or display 150. The system 100 can further include a console or structure 105 ("console 105") that incorporates, houses, and/or otherwise supports all or portions of the urine system 110, hydration system 120, diuretic system 130, the controller 140, and/or the display 150.

The urine system 110 is configured to collect urine from the patient P and/or monitor the patient's urine output (e.g., urine output amount and/or rates). The urine system 110 can include one or more collection containers 112 ("container 112") configured to hold urine, such as a disposable bag or other collection device. The container 112 can be fluidly coupled to the patient P via a fluid line 119 (e.g., a tubing line). The fluid line 119 can be connectable to a disposable catheter 118 (e.g., a Foley catheter, Texan Condom catheter, PureWick catheter, etc.) placed in or otherwise connected to the bladder of the patient P.

In some embodiments, urine flow through the fluid line 119 is driven by the patient's urine production, gravity (e.g., the bladder of the patient P is positioned higher than the container 112), and/or a siphon effect between the patient's bladder and the container 112. In other embodiments, the urine system 110 can also include a pump (not shown) operably coupled to the fluid line 119 for actuating urine flow through the fluid line 119 and into the container 112. The pump can be or include any device suitable for pumping fluid, such as a peristaltic pump. The pump can be used to initiate urine flow from the patient's body at the start of the procedure. The pump can also maintain urine flow during the treatment procedure at a desired flow rate, and can operate continuously, periodically (e.g., at predetermined time intervals), and/or in response to user input and/or detected issues (e.g., unexpected interruptions in urine flow). The pump can also be used to clear air locks and/or other obstructions from the fluid line 119. Additional examples of devices suitable for priming the fluid line 119 with fluid, pumping urine through the fluid line 119, and/or clearing air locks from the fluid line 119 are described further below with reference to FIGS. 10 11, and 15A-15D.

The urine system 110 can include one or more sensors 114 ("sensor(s) 114") configured to detect the patient's urine output (e.g., an amount and/or rate of urine output). The sensor(s) 114 can be operably coupled to the controller 140 so the controller 140 can monitor and/or compute the patient's urine output based on the data generated by the sensor(s) 114. The urine output can be determined in many different ways, such as based on urine flow (e.g., through the fluid line 119 and/or into the container 112), the amount of urine in the container 112 (e.g., based on the weight of the container 112, level of urine in the container 112, etc.), and/or other properties associated with the urine. The sensor(s) 114 can include one or more of the following: a flow sensor, drip counter, fluid weight sensor, fluid level sensor, float sensor, optical sensor, ultrasonic sensor, contact-based sensor (e.g., a paddle wheel sensor) and/or other sensors known in the art suitable for measuring a urine output amount and/or rate. In the embodiment of FIG. 1A, the sensor(s) 114 are positioned at the console 105. In other embodiments, however, some or all of the sensor(s) 114 can be at a different location in the system 100, such as on or in the line 119, on or in the container 112, and/or on or in the patient P.

In some embodiments, the sensor(s) 114 can include at least one sensor configured to measure one or more characteristics of the urine, in addition to detecting the patient's urine output. For example, the sensor(s) 114 can be configured to measure urine temperature, urine conductivity, urine oxygenation, urine specific gravity, and/or levels of one or more analytes in the urine (e.g., creatinine, sodium, potassium, etc.). Such characteristics can be useful, e.g., in determining effectiveness of a particular therapy and/or whether the patient P is in or could be approaching a critical condition. For example, urine conductivity and/or urine electrolytes (e.g., sodium) can indicate whether the patient is responding well to the fluid therapy, or whether the patient is in a critical condition and fluid therapy should cease. In some embodiments, urine conductivity (either alone or in combination with urine specific gravity) is used as a proxy for measurements of urine sodium and/or other urine electrolytes, e.g., a higher urine conductivity can correlate to higher urine sodium levels and a lower urine conductivity can correlate to lower urine sodium levels. As another example, urine temperature measurements can be used to detect urine flow (e.g., based on heat loss through the fluid line 119). The urine temperature can also be used as a proxy for the patient's body temperature, which in turn can correlate to the patient's current clinical state.

Optionally, the sensor(s) 114 can include at least one sensor configured to monitor the status of the urine collection procedure, such as whether urine collection is proceeding normally, whether there are interruptions in urine flow, whether there is a blockage or leak in the urine system 110, etc. For example, the sensor(s) 114 can include a leak sensor configured to detect whether a leakage is present in the urine system 110 (e.g., at or near the fluid line 119, catheter 118, and/or container 112). Leaks can be detected based on changes in urine flow rate, changes in pressure, the presence of moisture, or any other suitable parameter. In some embodiments, the controller 140 is configured to analyze the data from the leak sensor and/or other sensor(s) 114 to differentiate between low urine output rates versus leaks in the urine system 110.

As another example, the sensor(s) 114 can include a pressure sensor configured to measure the fluid pressure in the fluid line 119. The controller 140 can use the pressure measurements to monitor the status of urine flow, and optionally, detect whether there are any interruptions (e.g., decreases, sudden stoppages) or other issues with urine collection. In some embodiments, the controller 140 analyzes the pressure measurements to determine whether interruptions are due to low urine flow (e.g., the patient's bladder is empty or nearly empty), an air lock or other obstruction in the fluid line 119, a leak in the urine system 110 and/or a kink in the fluid line 119 and/or catheter 118. The controller 140 can alert the user if manual intervention is helpful or needed (e.g., to clear the obstruction, fix the leak, remove kinks from the fluid line 119, etc.). In embodiments where the urine system 110 includes a pump, the controller 140 can automatically activate the pump and/or increase the pumping rate to clear the obstruction from the fluid line 119.

The hydration system 120 can include at least one hydration fluid source 122 ("fluid source 122"—a bag, bottle, reservoir, etc.) containing a hydration fluid, such as saline (e.g., a premixed saline solution), Ringler's lactate solution, and/or other any other liquid solution suitable for infusion in the patient P. The hydration fluid can be isotonic, hypertonic, or hypotonic, e.g., depending on the patient's condition and/or other treatment considerations. Optionally, the composition of the hydration fluid (e.g., sodium, chloride, potassium, bicarbonate, etc.) can be varied based on the patient's condition and/or expected or measured electrolyte loss during the treatment procedure.

The fluid source 122 can be connected to the patient P via at least one fluid line (e.g., an IV line or other tubing), such as first fluid line 129a and a second fluid line 129b. The fluid source 122 can be operably coupled to one or more hydration fluid components 124 for actuating and/or monitoring hydration fluid infusion via the first and second fluid lines 129a-b, such as a hydration fluid pump 126 and/or at least one hydration fluid sensor 128 ("fluid sensor 128"). In the illustrated embodiment, the fluid source 122 is fluidly coupled to the hydration fluid pump 126 via the first fluid line 129a, and the hydration fluid pump 126 can pump the hydration fluid into the patient P via the second fluid line 129b. The hydration fluid pump 126 can be or include a peristaltic pump or other pump suitable for infusing a fluid into the patient's body (e.g., via an IV route or another route).

The fluid sensor 128 can be configured to determine an amount and/or rate of hydration fluid flowing from the fluid source 122 toward the patient P, and can include a flow sensor, pressure sensor, and/or other sensor configured to determine fluid output from the pump 126. Alternatively or in combination, the fluid sensor 128 can monitor hydration infusion rate by measuring the pumping rate of the pump 126 (e.g., the number of rotations of the pump 126 per minute). As described elsewhere herein, the controller 140 can be operatively coupled to the hydration system 120 and can receive sensor data from the fluid sensor 128 to determine a hydration fluid infusion rate. The controller 140 can control the pumping rate of the pump 126 to control the amount and/or rate of hydration fluid provided to the patient P.

Optionally, the amount of hydration fluid in the fluid source 122 can be monitored, e.g., based on weight, volume, fluid levels, flow rates, etc. In such embodiments, the fluid source 122 can be operably coupled to an additional sensor separate from the fluid sensor 128 (not shown), such as a fluid level monitor, float sensor, weight sensor, optical sensor, drip counter, flow measurement sensor, or the like. The additional sensor can provide an independent source of measurement data for determining and/or verifying the amount and/or rate of hydration fluid being provided to the patient P, which can be helpful for improving measurement accuracy.

In some embodiments, the hydration system 120 includes at least one sensor configured to detect the presence of the fluid source 122, such as a location sensor, optical sensor, weight sensor, etc. The hydration system 120 can use the sensor data to automatically determine whether the fluid source 122 is present or absent, e.g., to assess whether the system 100 is ready to initiate the fluid therapy treatment. Optionally, the sensor data can be used to detect if the user is removing the fluid source 122 during the treatment procedure, e.g., to switch an empty or nearly empty fluid source 122 with a new fluid source 122. In such embodiments, the system 100 can automatically pause hydration fluid infusion until the fluid source 122 has been replaced. Accordingly, the user can switch fluid sources 122 without having to inform the system 100 or manually pause the procedure.

The diuretic system 130 can be configured to automatically provide a diuretic to the patient P. The diuretic system 130 can include a diuretic source 134 (e.g., syringe, bag, reservoir, etc.) containing a diuretic, such as bumetanide (Bumex®), ethacrynic acid (Edecrin®), furosemide (Lasix®), torsemide (Demadex®), and/or other diuretics known in the art, each of which may be part of a fluid solution (e.g., a mixture of saline and a diuretic or other agent). In some embodiments, the identity and/or concentration of the diuretic can be received by the controller 140 via user input (e.g., using the display 150), by scanning a barcode of the diuretic source 134 or other container of the diuretic, and/or any other suitable technique.

The diuretic source 134 can be connected to the patient P via a fluid line 139 (e.g., an IV line or other tubing). The diuretic source 134 can also be operably coupled to one or more diuretic components 136 for actuating and/or monitoring diuretic delivery via the fluid line 139. For example, the diuretic components 136 can include a diuretic pump configured to pump the diuretic through the fluid line 139 and toward the patient P. The diuretic pump can include a peristaltic pump, a syringe pump, a metering pump, or other device suitable for delivering the diuretic to the patient P at a plurality of dosage rates. The diuretic pump can deliver the diuretic according to any suitable delivery profile, such as at a controlled continuous rate and/or in controlled boluses delivered at regular intervals through the fluid line 139. Additional details of diuretic delivery profiles are provided below in connection with FIG. 2.

In some embodiments, the diuretic pump is or includes a syringe pump having a mechanical injector or plunger that is operably coupled to the controller 140, such that the controller 140 causes movement of the injector to transfer the diuretic to the patient P. The syringe pump can include or be coupled to an actuator that mechanically drives the injector to control the delivery of the diuretic to the patient P. For example, the actuator can be or include a mechanical actuator, such as a nut for rotating a screw to drive the injector. The syringe pump can also include or be operably coupled to a sensor for detecting the position of the injector. Alternatively or in combination, the diuretic pump can include other types of pumps and/or actuators. For example, the diuretic pump can include a motor, a gearbox operatively connected to the motor, a sensor for measuring rotation of said motor (e.g., a tachometer or an optical encoder), and/or a microcontroller configured to control operation of the motor and monitor the quantity of diuretic delivered to the patient P. As another example, the diuretic pump can include an electric motor, such as a rotary motor, a linear motor, and/or a series of electrically actuated solenoids configured to propel liquid from the diuretic source 134 and through the line 139 toward the patient P.

In some embodiments, the diuretic components 136 include one or more diuretic sensors configured to determine an amount and/or rate of diuretic flowing toward the patient P. The one or more diuretic sensors can include, for example, a flow sensor, weight sensor, and/or other sensor type configured to determine the amount and/or rate of diuretic delivered from the diuretic source 134. Optionally, the diuretic sensors can measure diuretic delivery based on the output from the diuretic pump, such as by monitoring the pumping rate (e.g., number of rotations of the diuretic pump per minute, plunger position, etc.). The diuretic components 136 can include additional functional components, such as an air bubble detector, pressure sensor, extravasation sensor (e.g., ivWatch device), and/or other embedded electronics, e.g., to provide feedback signals to the controller 140 to ensure accurate diuretic infusion and/or monitor infusion status.

The controller 140 is configured to automatically control hydration fluid and/or diuretic infusion (e.g., based at least in part on the patient's urine output) to promote safe and effective diuresis of the patient P. The controller 140 can include one or more processor(s) and tangible, non-transient memory configured to store programmable instructions. The controller 140 can be operably coupled to the urine system 110, hydration system 120 and/or diuretic system 130 to receive data (e.g., sensor data) from and transmit data (e.g., control signals) to the various components of these systems. For example, the controller 140 can receive sensor data from the urine system 110 (e.g., from sensor(s) 114) to determine and/or monitor the patient's urine output. Based on the urine output, the controller 140 can determine an appropriate diuretic dosage amount and/or rate to administer to the patient P, and can cause the diuretic system 130 to deliver the diuretic accordingly. For example, the controller 140 can determine a pumping rate of the diuretic pump to produce the desired delivery profile for the diuretic. Similarly, the controller 140 can determine an appropriate hydration fluid infusion rate for the patient P (e.g., based on the urine output and/or the diuretic dosage rate), and can cause the hydration system 120 to deliver the appropriate hydration fluid amount and/or rate. For example, the controller 140 can determine a pumping rate for the hydration fluid pump 126 to achieve the desired hydration fluid infusion rate. The controller 140 can regulate the diuretic dosage rate and/or hydration fluid infusion rates based on a suitable treatment regimen protocol, e.g., prescribed by a physician and/or managed by the controller 140.

During the procedure, the controller 140 can receive sensor data from the various sensors of the urine system 110, hydration system 120 and/or diuretic system 130 to monitor the urine output, hydration fluid infusion rate, and/or diuretic dosage rate, respectively. The controller 140 can also receive sensor data from additional sensors configured to monitor patient status and/or operational status of the system 100, such as fluid pressure sensors, blood pressure sensors, air bubble detectors, and the like. For example, the controller 140 can be operably coupled to at least one sensor implanted in, attached to, or otherwise associated with the patient P. The sensor(s) can provide data regarding any of the following patient parameters: pressure levels (e.g., pulmonary artery pressure, left atrial pressure), bioelectric measurements (e.g., bioimpedance vector analysis (BIVA)), hemoglobin measurements (e.g., non-invasive hemoglobin measurements), urine oxygenation levels, urine composition (e.g., creatine, sodium, potassium, chloride, etc.), urine temperature, body temperature (e.g., bladder temperature), oral fluid intake, and the like. The controller 140 can use the data from any of the sensors described herein to monitor treatment progress (e.g., whether the treatment is complete), patient status (e.g., whether the patient is responding well or poorly to treatment), and/or potential safety concerns (e.g., whether the diuresis is too aggressive, whether the patient is exhibiting side effects). The controller 140 can also adjust the hydration fluid infusion rate and/or diuretic dosage rate based on the sensor data. Additionally, the sensor data can also provide feedback to the controller 140 to confirm or verify the effectiveness of the fluid therapy.

The controller 140 can also use other data for monitoring and/or controlling the therapy, such as settings for the system 100, user input, data indicative of a desired treatment regimen (e.g., a programmed diuretic and/or hydration fluid delivery profile over time), and/or other data collected or calculated by the controller 140. In some embodiments, the data used by the controller 140 includes current and/or historical data for the patient P, such as diuretic dosages delivered to the patient P, urine output volume or rate, the amount of hydration fluid infused into the patient P, the weight or change in weight of the patient P at various times during the infusion of the diuretic, indicators of the patient's renal function (e.g., estimated glomerular Filtration Rate (eGFR)), and/or the time(s) during which the patient P was treated with the system 100.

The display 150 (e.g., a touchscreen, monitor, etc.) can include a user interface configured to receive inputs from the user and display outputs to the user. In some embodiments, the display 150 is operatively coupled to the controller 140 and thus can be used to receive user input indicating treatment parameters, such as parameters for urine output, hydration fluid infusion, and/or diuretic dosage. The treatment parameters can include, for example: a desired fluid balance level (e.g., a positive, negative, or neutral fluid balance), target fluid removal volume (e.g., minimum and/or maximum amount of fluid to be removed), desired urine output level (e.g., a total amount of urine output; a target maximum, minimum, and/or average urine output rate), treatment duration (e.g., maximum and/or minimum duration of the treatment procedure; planned duration of the input balance level and/or urine output level), hydration fluid type, hydration fluid infusion rate (e.g., maximum, minimum, and/or average infusion rate), hydration fluid infusion profile (e.g., a function indicating how the amount and/or rate of hydration fluid infusion should vary over time), time limits associated with hydration fluid infusion (e.g., maximum and/or minimum time period for hydration fluid infusion), diuretic type, diuretic dosage (e.g., maximum and/or minimum dosage), diuretic dosage rate (e.g., maximum, minimum, and/or average dosage rate), diuretic dosage profile (e.g., a function indicating how the dosage amount and/or dosage rate of diuretic should vary over time), time limits associated with diuretic delivery (e.g., maximum and/or minimum time period for diuretic delivery), other fluids received by the patient during the procedure (e.g., volume of ingested fluid, volume of fluid from other medical agents besides the diuretic and/or hydration fluid), and/or suitable combinations thereof. Other patient-related inputs may also be received at the display 150 and can include, for example, the patient's sex, weight (e.g., "dry" weight), age, ethnicity, clinical state (e.g., renal function parameters, electrolyte levels such as serum chloride levels), medical history (e.g., outcomes of previous fluid removal procedures), diagnoses (e.g., ADHF, CHF), medications (e.g., whether the patient is diuretic-naïve or diuretic-resistant), dietary factors (e.g., whether the patient is consuming a high-salt or low-salt diet, amount of oral fluid intake), etc.

Alternatively or in combination, the user input via the display 150 can prompt the controller 140 to retrieve treatment parameters (e.g., maximum diuretic dosage, maximum continuous diuretic dosage, and minimum desired urine rate) from tables and/or other data sources. The data sources can be stored in the system 100 (e.g., in a memory associated with the controller 140) and/or can be stored in a separate device (e.g., a remote computing device). In some embodiments, the controller 140 retrieves data from a remote database and/or server via a communication network (e.g., a wired network, a wireless network, a cloud-based network, the Internet, and/or suitable combinations thereof). In such embodiments, the controller 140 can be operably coupled to a communication device and/or interface configured to transmit and receive data via the communication network.

The controller 140 can output the treatment parameters to the user via the display 150 for review and/or feedback. For example, the display 150 can show recommended treatment parameters for the patient P, such as recommendations for the diuretic dosage rate (e.g., initial, maximum, and/or minimum dosage rate), hydration fluid infusion rate (e.g., initial, maximum, and/or minimum infusion rate), urine output rate (e.g., maximum and/or minimum output rate), treatment duration (e.g., maximum time period for diuretic and/or hydration fluid infusion; maximum total treatment duration), and so on. As another example, the display 150 can output one or more predetermined treatment programs so the user can select the appropriate program for the particular patient P. Optionally, the user can modify any of the displayed treatment parameters, if desired.

During the treatment procedure, the controller 140 can output information regarding procedure status to the user via the display 150. For example, the controller 140 can display information regarding any of the following: urine output (e.g., current urine output rate and/or amount, urine output rate and/or amount over time, total amount of urine output so far), hydration fluid infusion (e.g., current infusion rate and/or amount, infusion rate and/or amount over time, total amount of hydration fluid infused so far), diuretic delivery (e.g., current dosage rate and/or amount, dosage rate and/or amount over time, total amount of diuretic delivered so far), fluid balance (e.g., current fluid balance, fluid balance over time, net fluid removal so far), system status (e.g., amount of hydration fluid remaining in the fluid source 122, amount of diuretic remaining in the diuretic source 134, remaining storage capacity in the container 112), treatment time (e.g., treatment start time, projected and/or planned treatment end time, total treatment duration so far), notifications (e.g., alerts, alarms, error messages), and the like. The user can review the displayed information, and, if appropriate, provide input instructing the controller 140 to adjust, pause, and/or stop the treatment procedure.

In some embodiments, the system 100 includes redundancy in the urine system 110, hydration system 120, and/or diuretic system 130 to reduce or minimize treatment interruptions, e.g., due to running out of urine collection capacity, running out of hydration fluid, and/or running out of diuretic. For example, the system 100 can include redundant components (e.g., containers 112, fluid sources 122, and/or diuretic sources 134), which can be stored at predetermined locations (e.g., on or within the console 105 or another portion of the system 100). The controller 140 can be configured to detect the presence of the redundant components, and can automatically or semi-automatically switch between these components so the treatment procedure can continue uninterrupted or substantially uninterrupted. Alternatively or in combination, the system 100 can adjust the timing of user alerts related to urine collection capacity, hydration fluid levels, and/or diuretic levels, based on the availability of redundant components. For example, if redundant components are available, the system 100 can generate alerts at a later time (e.g., closer in time to when the container 112 would be full, when the fluid source 122 would be empty, and/or when the diuretic source 134 would be empty), since the system 100 can automatically switch to using the redundant components, or the user can rapidly perform the switch using the redundant components that are already stored locally at the system 100, rather than having to retrieve replacements from another location.

The lack of interruption in fluid therapy can help ensure effectiveness of the fluid therapy, e.g., by relieving the patient's fluid overload condition as quickly and safely as possible. In some embodiments, even brief interruptions in diuretic delivery and/or hydration fluid infusion can significantly affect the patient's urine output (e.g., cause the urine output rate to drop), which can interfere with therapeutic efficacy and prolong treatment time. The concerns described above regarding diuretic and/or hydration fluid backup supply may be unique to the present technology, e.g., due to the relatively large amounts of diuretic and/or hydration fluid that are utilized over time in some embodiments of the treatment procedures described herein. That is, whereas conventional systems and methods may utilize just a single diuretic source and/or a single hydration fluid source because of the relatively low amount of diuretic and/or hydration fluid administered, the present technology may benefit from multiple diuretic sources and/or hydration fluid sources to ensure treatment continuity. Similarly, the treatment procedures of the present technology can cause the patient P to produce relatively large volumes and/or rates of urine output compared to conventional procedures, such that multiple containers 112 may be helpful to reduce the number of times the user has to empty and/or replace the containers 112 during the procedure.

For example, in some embodiments, the urine system 110 includes two or more redundant containers 112 to ensure fluid therapy does not need to be stopped or interrupted due to the container 112 being full. In such embodiments, the urine system 110 can include a flow control assembly 116 (e.g., valves and/or other flow control components) operably coupled to the controller 140, and configured to selectively direct the urine from the patient P to one or more of the containers 112. The flow control assembly 116 can initially direct the urine received from the patient P to a first container 112. Once the flow control assembly 116 detects or determines the first container is full or nearly full (e.g., based on sensor data from the sensor(s) 114), the flow control assembly 116 can redirect the urine received from the patient P to a second container 112. While urine is being directed to the second container 112, a user can empty the first container 112 or replace the first container 112 with an empty container 112. The flow control assembly 116 and/or controller 140 can generate an alert to the user to indicate the first container is full and needs to be replaced or emptied. This process can be repeated such that fluid management therapy is not inadvertently interrupted due to the containers 112 being full and/or the urine system 110 being unable to accept urine output. In some embodiments, the treatment procedures described herein result in relatively large amounts and/or rates of urine output (e.g., compared to conventional therapies), such that automatic switching between multiple urine containers is advantageous to minimize treatment interruptions. Additional details of the urine system 110 and multiple container 112, and associated devices and methods, are described below with reference to FIGS. 3-11.

As another example, the hydration system 120 can include multiple redundant hydration fluid sources 122, e.g., to ensure the hydration fluid infusion can continue without interruption for the entirety of a therapy session and/or to provide an additional time window for switching hydration fluid sources 122 without interrupting hydration fluid infusion. In such embodiments, the hydration system 120 can include a hydration control assembly (e.g., valves and/or other flow control components—not shown) operably coupled to the controller 140, and configured to switch the source of hydration fluid from a first fluid source 122 to a second fluid source 122. In such embodiments, the hydration control assembly can initially deliver hydration fluid from the first fluid source 122 to the patient P. The hydration control assembly can monitor whether the first fluid source 122 is empty or nearly empty, e.g., based on data from the fluid sensor 128 and/or other sensors associated with the hydration system 120. Once the hydration control assembly detects or determines the first fluid source 122 is empty or nearly empty (e.g., the remaining amount of hydration fluid is below a predetermined threshold), the hydration control assembly can switch to delivering hydration fluid from the second source 122. The switching process can be repeated such that fluid therapy is not inadvertently interrupted due to the fluid source 122 being empty and/or the hydration system 120 being unable to provide hydration fluid.

The process of switching the hydration fluid source 122 can be performed automatically, semi-automatically, or manually. In some embodiments, semi-automatic or manual switching between the first and second fluid sources 122 may be beneficial to ensure the hydration system 120 does not automatically infuse hydration fluid without user confirmation. In such embodiments, the hydration control assembly and/or controller 140 can output an alert asking the user to verify that the hydration fluid should be switched from the first fluid source 122 to the second fluid source 122. Upon switching to the second fluid source 122, the controller 140 can generate an alert to the user to indicate the first fluid source 122 is empty and needs to be replaced. Optionally, the hydration control assembly and/or controller 140 can implement a pre-approval procedure in which the user allows the hydration system 120 to automatically infuse a specified volume of additional hydration fluid. Once that volume has been delivered to the patient P, the user may need to provide re-approval before further automatic infusion of hydration fluid.

In some embodiments, the different fluid sources 122 of the hydration system 120 each provide the same type of hydration fluid. In other embodiments, however, some or all of the fluid sources 122 can provide different types of hydration fluid. The hydration fluids can differ from each other with respect to tonicity, composition, electrolyte content, etc. Depending on the patient's response to diuresis, the hydration system 120 can deliver multiple different hydration fluids to the patient P sequentially or concurrently. For example, if the patient's urine output indicates that the patient P has an electrolyte imbalance (e.g., a positive sodium balance), the hydration system 120 can switch to delivering a hydration fluid that would address the imbalance (e.g., a hydration fluid with lower sodium content). The switching can be performed using any of the techniques and/or devices described above. Accordingly, the particular fluid or fluids delivered to the patient P can be tailored to the patient's particular clinical state and/or response to treatment.

In yet another example, the diuretic system 130 can include multiple redundant diuretic sources 134, e.g., to ensure the diuretic delivery can continue without interruption for the entirety of a therapy session and/or to provide an additional time window for switching diuretic sources 134 without interrupting diuretic delivery. For example, if a first diuretic source 134 (e.g., a first syringe or container) is spent, the diuretic can continue to be supplied (e.g., without substantial interruption) via a second diuretic source 134 (e.g., a second syringe or container). The second diuretic source 134 can be connected to the console 105, and can be operably coupled to a sensor configured to detect the presence of the second diuretic source 134 (e.g., a location sensor, optical sensor, weight sensor, etc.). Accordingly, the diuretic system 130 can switch to the second diuretic source 134 if the first diuretic source 134 is empty or nearly empty, and the second diuretic source 134 is present.

In some embodiments, the diuretic system 130 includes two independent diuretic pumps each including its own diuretic source 134. For example, the diuretic system 130 can include syringe pumps each fluidly coupled to its own syringe filled with diuretic. In some cases, such syringes may only be filled by pharmacists or other health care professionals, and thus may not be readily replaced (e.g., in less than a few hours) by the user. When the diuretic system 130 and/or controller 140 detects that the first diuretic source 134 is empty or nearly empty (e.g., below a predetermined threshold), the diuretic supply can be switched (e.g., automatically or manually) to a second diuretic source 134. In some embodiments, the diuretic system 130 can include one or more sensors configured to detect whether a backup syringe pump is available for use. The switching process can include stopping a first syringe pump fluidly coupled to the first syringe, and starting a second syringe pump fluidly coupled to the second syringe. In other embodiments, the diuretic system 130 includes a single diuretic pump (e.g., syringe pump) connected to two diuretic sources 134. In such embodiments, case switching between the first and second diuretic sources 134 can involve using a diuretic control assembly (e.g., valves and/or other flow control components) to switch the diuretic pump from delivering diuretic from the first diuretic source 134 to the second diuretic source 134. The switching process can be repeated such that fluid therapy is not inadvertently interrupted due to the diuretic source 134 being empty and/or the diuretic system 130 being unable to provide diuretic.

The process of switching the diuretic source 134 can be performed automatically, semi-automatically, or manually. In some embodiments, manual or semi-automatic switching between the first and second diuretic sources 134 may be beneficial to ensure the diuretic system 130 does not automatically infuse a large volume of diuretic without user confirmation. In such embodiments, the controller 140 can output an alert asking the user to verify that the diuretic should be switched from the first diuretic source 134 to the second diuretic source 134. Upon switching to the second diuretic source 134, the controller 140 can generate an alert to the user to indicate the first diuretic source 134 is empty and needs to be replaced. Optionally, the controller 140 can predict a time point and/or time range when the first diuretic source 134 will be empty (e.g., based on the diuretic dosage rate), and can output a notification so the user can order or otherwise prepare a replacement diuretic source 134 before the first diuretic source 134 runs out. Moreover, the diuretic control assembly and/or controller 140 can implement a pre-approval procedure in which the user allows the diuretic system 130 to automatically delivery a specified additional dosage of diuretic. Once that dosage has been delivered to the patient P, the user may need to provide re-approval before further automatic delivery of diuretic.

In some embodiments, the different diuretic sources 134 of the diuretic system 130 each provide the same type of diuretic. In other embodiments, however, some or all of the diuretic sources 134 can provide different types of diuretics. Depending on the patient's response to diuresis, the diuretic system 130 can deliver multiple different diuretics to the patient P sequentially or concurrently. For example, the diuretic system 130 can initially deliver a first diuretic to the patient P from a first diuretic source 134. If the patient P responds poorly to the first diuretic (e.g., the urine output rate does not increase or increases very slowly), the diuretic system 130 can switch to delivering a second, different diuretic from a second diuretic source 134. The diuretic system 130 can continue delivering the first diuretic concurrently with the second diuretic, or can terminate delivery of the first diuretic when the second diuretic is delivered. The switching can be performed using any of the techniques and/or devices described above. As another example, if the patient P does not respond well to a single diuretic, the diuretic system 130 can simultaneously administer multiple diuretics to the patient P. The ratio of the different diuretics can be varied as appropriate to elicit a suitable urine output rate. In other embodiments, however, rather than automatically administering additional diuretics, the diuretic system 130 can output a notification recommending that the user manually administer a different diuretic to the patient P and/or requesting that the user approve administration of a different diuretic, which may be beneficial for patient safety.

Figure 1B:
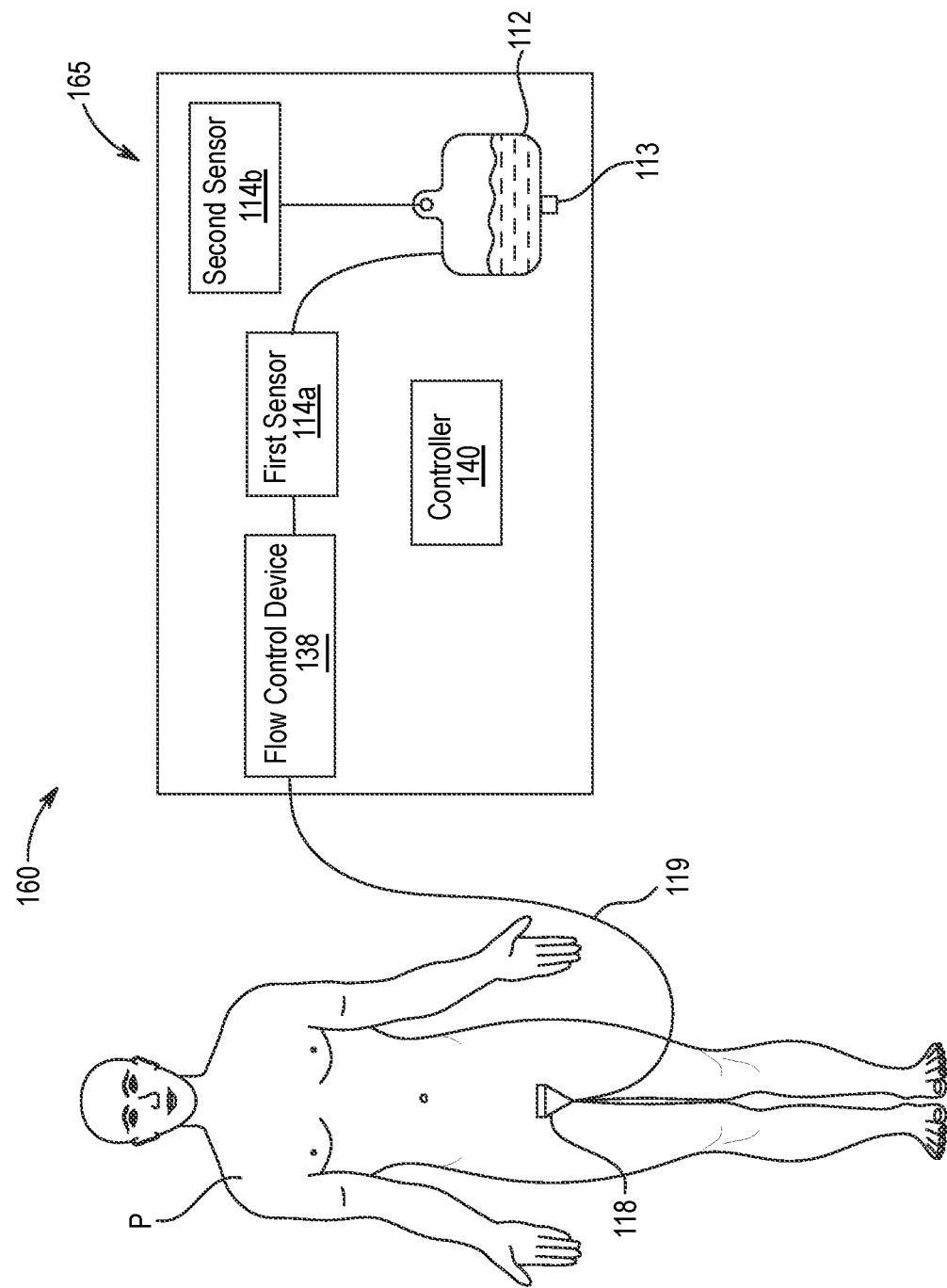

The system 100 illustrated in FIG. 1A can have several configurations, e.g., to include additional and/or fewer components. As an example, FIG. 1B is a partially schematic view of another fluid management system 160 for monitoring urine output and/or controlling fluid infusion into a patient P, in accordance with embodiments of the present technology. As shown in FIG. 1B, the system 160 can include a console 165 (e.g., the console 105; FIG. 1A) and many of the same features of the system 100, including the container 112 having a drain valve 113, the catheter 118, the fluid line 119, and the controller 140 (as previously described with reference to FIG. 1A). The system 160 can further include a flow control device 138 (e.g., a pinch valve), and multiple sensors for monitoring urine production and some of the sensors can be redundant sensors. The flow control device 138 can be operably coupled to the controller 140 and be configured to regulate flow from the patient to the container 112. In some embodiments, the flow control device 138 includes a pinch valve that regulates flow by externally pinching the fluid line 119. As shown in FIG. 1B, the flow control device 138 is upstream of the first sensor 114a. However, in other embodiments the flow control device 138 can be downstream of the first sensor 114a.

The sensors can include (i) a first sensor 114a (e.g., a flow sensor, thermal flow sensor (e.g., the Sensirion SLF3x Liquid Flow Sensor), a mechanical paddlewheel type flow sensor, an ultrasonic flow sensor, etc.) coupled (e.g., fluidly coupled) to the fluid line 119 and the catheter 118 and configured to measure a flow rate of urine from the patient P, and (ii) a second sensor 114b (e.g., a weight sensor) coupled to the container 112 and configured to measure weight of the container 112. The first and second sensors 114a-b can be operably coupled to the controller 140. For embodiments in which the first sensor 114a comprises an ultrasonic flow sensor, the ultrasonic flow sensor can be positioned external to the fluid line 119 and thus not contact the fluid therein.

As disclosed elsewhere herein, the signal associated with urine production from the patient can be used by the system, e.g., to determine how much diuretic and/or hydration fluid to administer (e.g., automatically controlled administration of a diuretic and/or a hydration fluid). Accordingly, obtaining an accurate and reliable urine output signal can be beneficial. In such embodiments, the signal from the first or second sensor 114a-b can be compared to the signal from the other one of the first or second sensor 114a-b to ensure accuracy of measurement. The signals can be obtained at regular intervals (e.g., every second, 30 seconds, minute, 2 minutes, 5 minutes, 10 minutes, etc.), and can be used to produce average flow rates on a rolling basis or to calculate total urine volume over a given time period. For example, based on the signals obtained from the first and second sensors 114a-b, an average flow rate or patient urine output rate can be determined and continuously updated, e.g., for the previous minute.

In some embodiments, the signal from the second sensor 114b can be used as the primary source or input and the signal from the first sensor 114a can be used as a backup or secondary signal source. Alternatively, the signal from the first sensor 114a can be used as the primary source and the signal from the second sensor 114b can be used as a secondary signal source. The primary source may switch between the first and second sensors 114a-b if (e.g., only if) the current sensor serving as the primary source fails, is not available (e.g., taken offline), or other predetermined condition is met. For example, in some embodiments the signal from the second sensor 114b can be used as the primary source unless and/or until (i) the weight of the container 112 is above a predetermined threshold, indicating the container 112 is nearly full and needs to be drained, (ii) the weight of the container 112 is decreasing, likely indicating the container 112 is being drained and thus rendering the second sensor 114b less able to produce an accurate urine flow measurement, (iii) the weight of the container 112 is increasing at a rate less than expected, or is decreasing in weight, indicating the container 112 is being drained and thus rendering the second sensor 114 less able to produce an accurate urine flow measurement, and/or (iv) there is a discrepancy between the signals of the first and second sensors 114a-b, indicating the container 112 is being drained and/or one of the signals is not accurate. If one or more of these conditions is met, the system 160 or controller 140 can (i) be configured to preference one of the sensors over the other, and/or (ii) analyze the signals from both sensors and select the most reliable signal based on other operating conditions (e.g., the immediately previous obtained urine output rate, the average urine output rate, the diuretic dosage, the hydration infusion, etc.).

In such embodiment where a sensor used as the primary source is deactivated, that sensor may not be reactivated until another condition is met. For example, if the signal from the second sensor 114b is removed from being the primary source, e.g., due to a decrease in weight of the container 112, the signal from the second sensor 114b may not reengage as the primary source until a predetermined condition (e.g., an increase in weight of the container 112) occurs or a time (e.g., 30 seconds, 1 minute, 2 minutes, etc.) after the predetermined condition has elapsed. If the predetermined condition (e.g. an increase in weight of the container) is not met after a pre-specified time period, an alert may be generated to indicate to the user that an unexpected condition has been encountered, such as a suggestion that the drain valve 113 has not been closed, or that the urine bag is leaking.

In some embodiments, a determined discrepancy between the first and second sensors 114a-b can identify a potential fault in the system (e.g., faulty sensor) and cause the system 160 to stop all or portions of the fluid therapy, and/or alert the user that such discrepancy exists. In some embodiments, depending on which of and/or how long the first or second sensors 114a-b are offline or determined to be inaccurate, the system 160 or controller 140 may alter other aspects of therapy provided to the patient. For example, the amount of diuretic and/or hydration fluid provided to the patient may be maintained or decreased. In some embodiments, the first and second sensor can be tested during preparation of the system 160 for connection to the patient, such that if a failure of either of the sensors 114a-b is detected, or if there is a large discrepancy between the readings of the sensors 114a-b, an alert can be generated prior to the initiation of therapy, preventing the use of the system in a non-functional state.

In some embodiments, the first sensor 114a (i.e., the flow sensor) is omitted and the second sensor 114b (i.e., the weight sensor) is relied on to provide a urine flow output from the patient. In such embodiments, the sensor data obtained from the second sensor 114b is utilized to determine an average urine flow rate over a period of time, e.g., based on the rate of change of weight of the container 112. Additionally, in such embodiments, when the system 160 determines via the second sensor 114b that the weight of the container 112 is decreasing or not increasing at an expected rate, which may indicate the container 112 is being drained, the system can ignore the signal from the second sensor 114b for a predetermined period of time (e.g., 1 minute, 2 minutes, 5 minutes, etc.), before again relying on the signal to provide the urine flow output. During this predetermined period of time, the diuretic and/or hydration fluid provided to the patient can be maintained and/or decreased.

Advantageously, the system 160 and other embodiments of the present technology can remain operational and provide therapy even when the container 112 is replaced and/or emptied. For example, because the first sensor 114a is upstream of the container 112 and can be a flow sensor not dependent on weight of the container, the urine output of the patient can be monitored while the container is being replaced and/or emptied. As such, unlike other embodiments only having a sensor configured to measure weight of the container 112, and thus unable to provide accurate urine output measurements when the container is being replaced and/or emptied, embodiments of the present technology enable the system 160 to continue providing therapy uninterrupted. Additionally or alternatively, embodiments of the present technology enable a healthcare professional to drain the container 112 (e.g., via a drain valve 113 of the container 112) without (i) having to replace the container 112 and remove the container 112 from the system, and (ii) using the interface of the system, which may be prohibited and/or can inadvertently lead to interrupting fluid therapy of the patient.

Figure 1C:
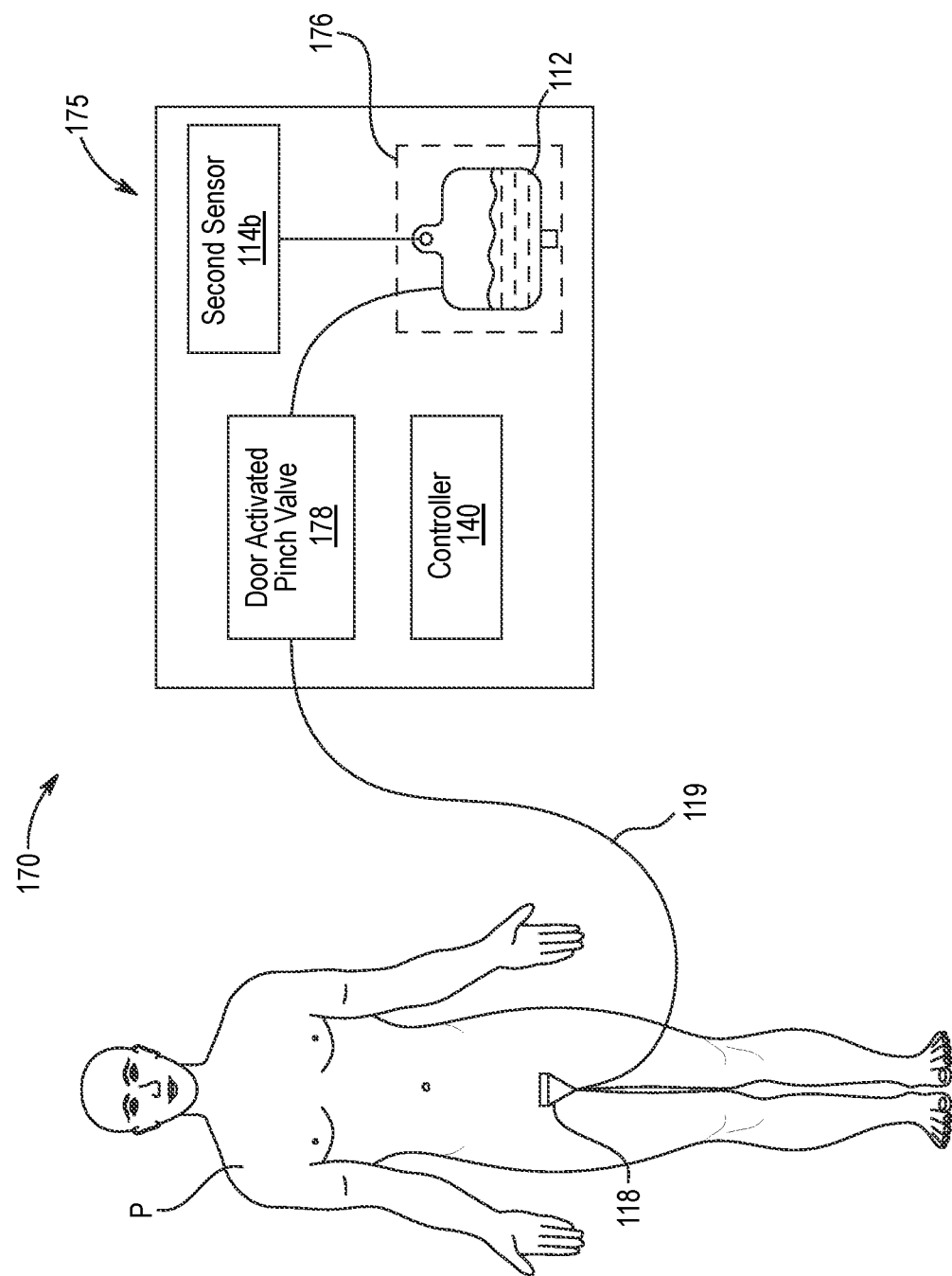

FIG. 1C is a partially schematic view of another fluid management system 170 for monitoring urine output and/or controlling fluid infusion into a patient P, in accordance with embodiments of the present technology. The system 170 can include a console 175 (e.g., the console 105; FIG. 1A) and many of the same features of the system 100 and/or system 160. As shown in FIG. 1C, the system 170 can further include an access door 176 enabling access to the container 112, and a door-activated valve 178 (e.g., a pinch valve) coupled (e.g., fluidly coupled) to and positioned between the catheter 118 and container 112. The door 176 and valve 178 can be operably coupled to the controller 140, such that the controller can determine whether each of the door 176 and valve 178 is open or closed, and/or actuate the valve 178 based on the position of the door 176. Additionally or alternatively, the valve 178 can be mechanically actuated by movement of the door 176. For example, opening the door 176 can mechanically close the valve 178, and closing the door 176 can mechanically open the valve 178.

In operation, the valve 178 can be (i) actuated and closed, e.g., via the controller 140, when the door 176 is determined to be open or not closed, and (ii) actuated and opened, e.g., via the controller 140, when the door 176 is closed or not open. As such, when the door 176 is opened to empty or replace the container 112, the valve 178 can be closed via the controller to prevent urine from draining from the system 170, during which time urine builds up in the patient's bladder. Once the container 112 is emptied or replaced with a new empty container 112 and the door 176 is closed, the valve 178 can be opened via the controller 140 to enable flow into the new container 112. At such time, the volume of urine excreted during the time the door 176 was open and/or the valve 178 was closed could be measured via the second sensor 114b and/or by the first sensor 114a.

Figure 1D:
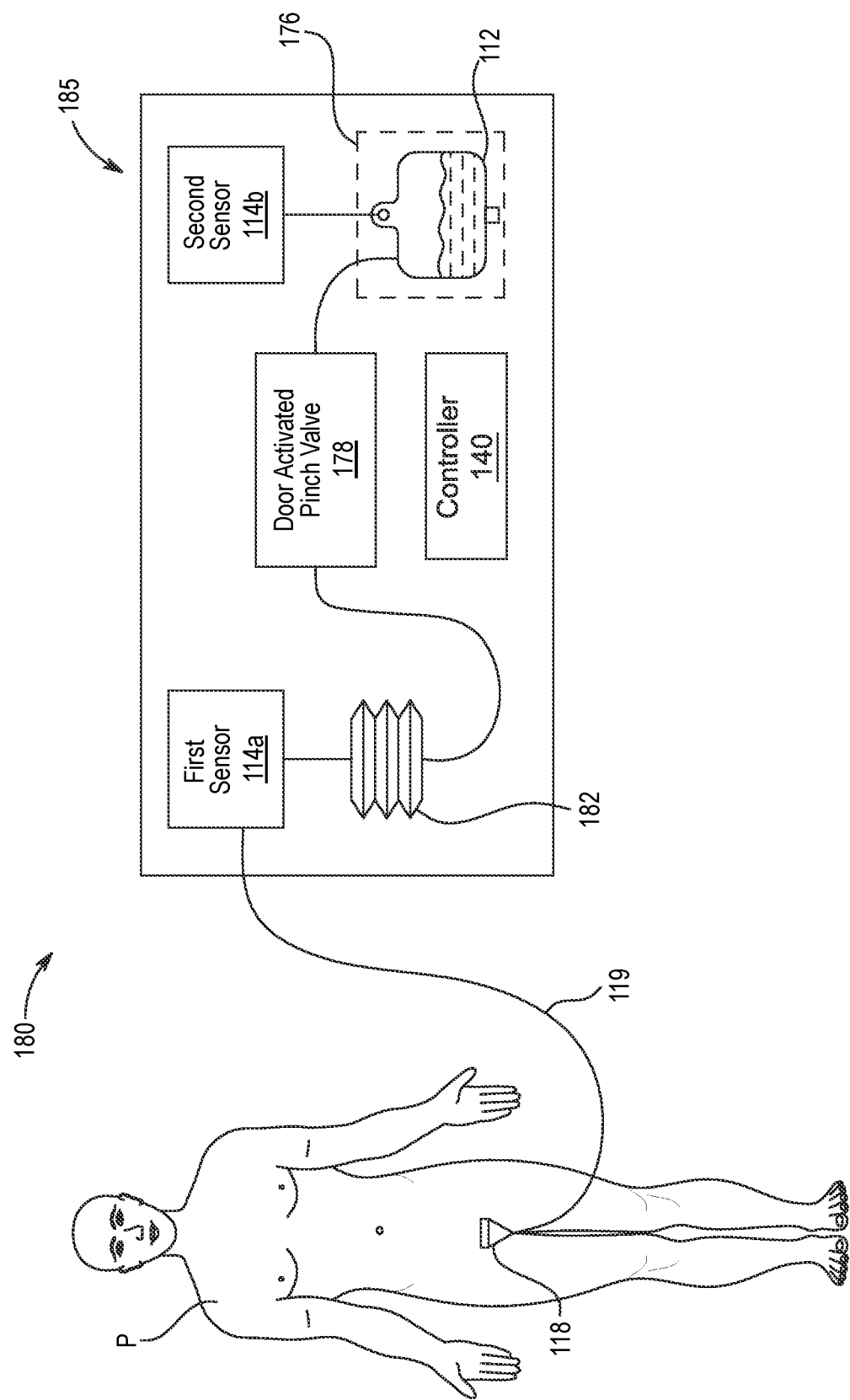

FIG. 1D is a partially schematic view of another fluid management system 180 for monitoring urine output and/or controlling fluid infusion into a patient P, in accordance with embodiments of the present technology. The system 180 can include a console 185 (e.g., the console 105; FIG. 1A) and many of the same features of the system 100, system 160, and/or system 170. As shown in FIG. 1D, the system 180 can further include a reservoir 182 fluidly coupled to and positioned between the catheter 118 and the container 112. The reservoir 182 can be an expandable reservoir, and/or be configured to store a volume of fluid provided from the patient P. As shown in FIG. 1D, the reservoir 182 can be positioned between the first sensor 114a and the valve 178.

In operation, when the door 176 is opened to empty or replace the container 112, the valve 178 is actuated to a closed position and urine from the patient begins to build in the reservoir 182. As previously noted, the valve 178 can be actuated by the controller 140 and/or mechanically actuated by the opening and closing of the door 176. Advantageously, because the reservoir 182 is positioned downstream of the first sensor 114a, the system 180 can remain online and does not need to pause or cease fluid therapy (e.g., diuretic and/or hydration fluid infusion) until the container 112 is replaced and/or the valve 178 is opened. Once the container 112 is emptied or replaced, flow to the container 112 can continue and the reservoir 182 can be drained.

In some embodiments, the system 180 may include other configurations to provide the same or similar functionality described above. For example, in some embodiments the access door 176 is omitted and the valve 178 is actuated based on the signal from the second sensor 114b. For example, in such embodiments if a weight below a predetermined threshold is detected by the second sensor 114b then the valve 178 is closed, and if a weight at or above the predetermined threshold is detected by the second sensor 114b then the valve is opened or remains open. Alternatively, the system can include an optical or proximity sensor, e.g., to detect a user reaching into the area to empty the container 112, and close the valve 178 in response.

The systems 100, 160, 170, 180 illustrated in FIGS. 1A-1D can have several configurations. For example, the locations of the various components of the system 100 can be altered, e.g., the urine system 110, hydration system 120, and/or diuretic system 130 can be at different locations in the console 105. As another example, any one of the urine system 110, hydration system 120, or diuretic system 130 can be part of a separate system or device (e.g., a separate console), or can be omitted altogether. For instance, in some embodiments, the urine system 110 is replaced with a mechanism for monitoring the patient's urine output that does not require the catheter 118 and/or urine collection, such as an ultrasound sensor that measures the patient's bladder volume. The ultrasound sensor can be implemented as a patch or similar device that is coupled to the patient's body. The controller 140 can process the ultrasound sensor data to detect changes in the bladder volume, and can determine the corresponding amount and/or rate of urine output based on the bladder volume. The use of non-invasive urine monitoring mechanisms such as an ultrasound sensor can allow the treatment procedures described herein to be performed in outpatient settings, and would allow the urine bag to be emptied at any time without disturbing the continuous measurement of urine flow or volume.

As another example, in some embodiments, the hydration system 120 is omitted such that diuresis is performed without hydration fluid infusion, or the hydration fluid is infused manually. Diuresis with hydration fluid infusion may be more beneficial for patients with low serum chloride levels (e.g., patients with low-salt diets), while patient with high serum chloride levels (e.g., patients with high-salt diets) may tolerate diuresis with little or no hydration fluid infusion. Optionally, the hydration fluid infusion rate can be varied at least partially based on the patient's serum chloride levels, e.g., lower amounts and/or rates of hydration fluid infusion can be used if the patient's serum chloride level is high (e.g., greater than or equal to 105 mmol/L).

In yet another example, the diuretic system 130 can be omitted such that no diuresis is performed, or the diuresis is performed manually. In such embodiments, the system 100 can provide automated fluid replacement via the hydration system 120 and/or can automatically monitor the patient's urine output via the urine system 110, but the diuretic would be administered manually by a healthcare professional in accordance with techniques known to those of skill in the art.

The systems 100, 160, 170, 180 can optionally include or be used in combination with additional systems or devices, such as systems or devices configured to perform any the following functions: administering other medications and/or agents besides the diuretic and hydration fluid (e.g., heart failure medication), monitoring other patient parameters besides urine output (e.g., blood pressure, weight, heart rate, blood oxygenation, respiratory rate, temperature), and/or performing other types of medical procedures on the patient P concurrently or sequentially with the fluid removal procedure (e.g., dialysis, ultrafiltration).

Figure 2:
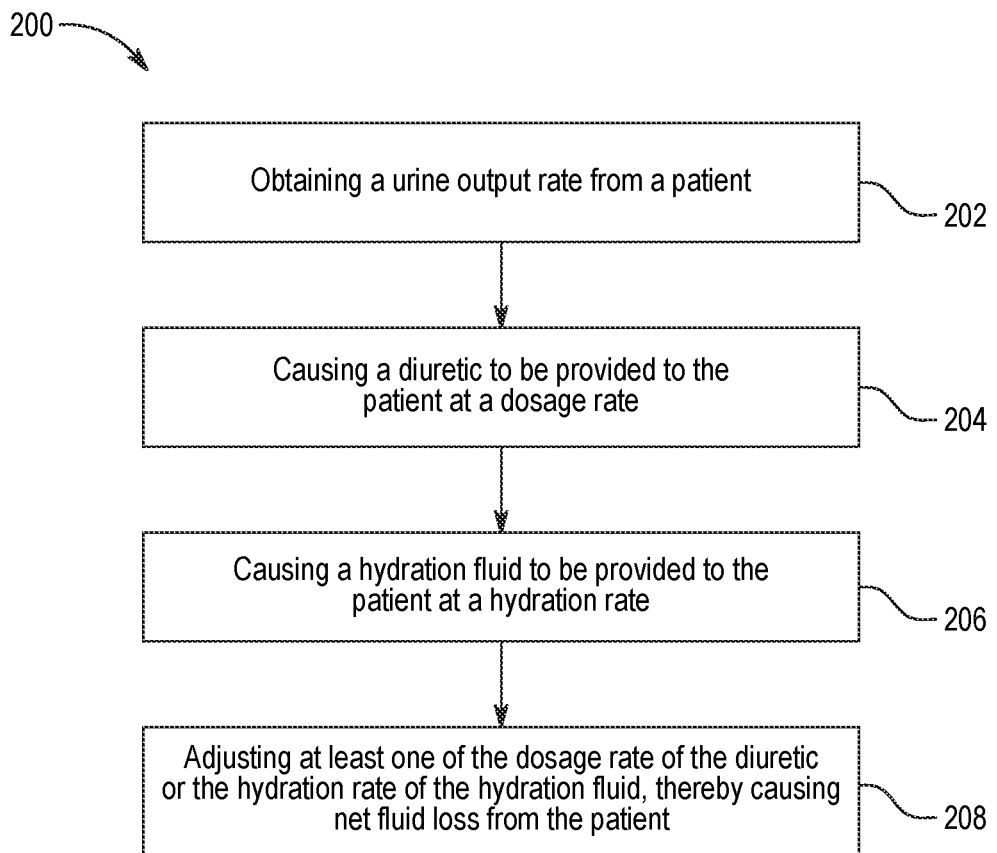
FIG. 2 is a flow diagram of a method for treating a patient, in accordance with embodiments of the present technology.

FIG. 2 is a flow diagram of a method 200 for treating a patient, in accordance with embodiments of the present technology. In some embodiments, the method 200 is used to treat the patient for fluid overload by removing fluid from the patient to produce a negative fluid balance (net fluid loss). The method 200 (and the other methods described herein) include one or more steps, blocks, phases, acts, portions, operations, or the like. The method 200 can be performed by any embodiment of the systems and devices described herein, such as the system 100 of FIG. 1A. In some embodiments, some or all of the stages of the method 200 are performed by a system or device including one or more processors and a memory storing instructions that, when executed by the one or more processors, cause the system or device to perform one or more of the stages described herein. For example, the method 200 can be performed by the controller 140 of the system 100 of FIG. 1A. Optionally, some or all of the stages of the method 200 can performed automatically or semi-automatically, with little or no human intervention.

The method 200 can begin at stage 202 with obtaining a urine output rate from a patient. The urine output rate can be obtained from a urine monitoring and/or collection system connected to the patient, such as the urine system 110 of FIG. 1A. The system can determine the urine output rate based on received input data, such as data from one or more sensors (e.g., the sensor(s) 114 of FIG. 1A). As described above, the sensor(s) can be configured to measure the urine output rate based on flow rate, weight (e.g., of the container 112 of FIG. 1A), volume, fluid level, and/or any other suitable parameter. The urine output rate can be calculated based on the received input, e.g., by a controller (e.g., controller 140 of FIG. 1A) operatively coupled to the sensor(s). The urine output rate can be a current rate or an average rate measured over a predetermined time period (e.g., the previous 5 or 10 minutes). The urine output rate can be updated on a continuous or recurring basis (e.g., every 30 seconds, 1 minutes, 2 minutes, etc.). In some embodiments, the process of stage 202 is performed concurrently with some or all of the other stages of the method 200 (e.g., stages 204, 206, and/or 208) to provide continuous or substantially continuous urine output monitoring through the entirety of the method 200.

At stage 204, the method 200 optionally continues with causing a diuretic to be provided to the patient at a dosage rate. The diuretic can be or include furosemide, bumetanide, ethacrynic acid, torsemide, combinations thereof, and/or other diuretics known in the art. In some embodiment, the diuretic is delivered as part of a solution including saline or other hydration fluid(s) mixed therewith. The diuretic can be provided automatically or semi-automatically by a diuretic system connected to the patient, such as the diuretic system 130 of FIG. 1A. The diuretic system can be operably coupled to a controller (e.g., controller 140 of FIG. 1A) for causing diuretic delivery in accordance with a planned and/or pre-programmed treatment procedure.

In some embodiments, the treatment procedure includes multiple phases, and each phase is associated with a different delivery profile for the diuretic. In such embodiments, stage 204 can be performed as part of an initial phase to determine an appropriate diuretic dosage rate for treating the patient (also known as a "dosage determining phase"). In the dosage determining phase, the diuretic is injected at an initial dosage rate, and the dosage rate can then be gradually increased to elicit an increase in the patient's urine output rate. The diuretic dosage rate can be increased according to a desired function or delivery profile, such as a continuous function, a step-wise function, or a combination thereof. The function can include iteratively increasing the dosage rate linearly, exponentially, according to a polynomial function, and/or any other suitable ramp function or profile. In some embodiments, the diuretic is delivered in a manner such that a subsequent dosage rate is a predetermined percentage (e.g., at least 5%, 10%, 15%, 25%, etc.) above the immediately previous dosage rate. The predetermined percentage can increase or decrease over time, e.g., depending on the desired fluid therapy and/or patient considerations. Optionally, the diuretic can be provided in a manner that doubles the diuretic dosage rate or total diuretic within a period of time (e.g., 10 minutes, 15 minutes, 20 minutes, or within a range of 10-20 minutes). In other embodiments, however, the dosage determining phase can include one or more time periods during which the diuretic dosage rate does not increase and/or is held substantially constant. The dosage determining phase can continue until the patient's urine output reaches or exceeds a desired threshold rate and/or a predetermined time period has elapsed, at which point the diuretic dosage rate can be adjusted, as described in stage 208 below.

At stage 206, the method 200 can optionally include causing a hydration fluid to be provided to the patient at a hydration rate. The hydration fluid can comprise saline and/or other fluids having sodium, and can be provided automatically or semi-automatically by a hydration fluid system connected to the patient, such as the hydration system 120 of FIG. 1A. The hydration fluid can be provided before, during, and/or after providing the diuretic in stage 204 (e.g., before, during, and/or after the dosage determining phase). Intravenous infusion of hydration fluid containing electrolytes (e.g., sodium and/or chloride) can increase diuretic efficiency, which is counterintuitive since a goal of fluid therapy is net removal of fluid. Hydration fluid can also reduce or inhibit intravascular depletion, decreases in cardiac output, and/or decreases in renal perfusion, among other benefits.

In some embodiments, the hydration fluid is provided to the patient based at least in part on the corresponding urine output rate, e.g., to drive net fluid loss from the patient. For example, the hydration rate can be less than the urine output rate. In some embodiments, the hydration rate is a percentage of the urine output rate (e.g., 90%, 80%, 70%, 60%, 50%, 40%, 30%, 20%, or 10% of the urine output rate) for a given range of urine output rates (e.g., from 0 ml/hr to 1000 ml/hr). Optionally, the percentage can be higher for certain parts of the range (e.g., for the lower end of the range to reduce the likelihood of hypotension) and/or lower for other parts of the range (e.g., for the higher end of the range to increase net fluid loss). As another example, the hydration rate can substantially match the urine output rate (e.g., 100% of the urine output rate) for an initial amount of urine output by the patient (e.g., at least the initial 150 ml, 200 ml, or 250 ml), for an initial time period (e.g., the first hour, 2 hours, or 3 hours), and/or until the patient's urine output rate reaches a predetermined threshold. Subsequently, the hydration rate can be adjusted to be less than the urine output rate. In a further example, the hydration rate may be determined based on whether the urine output rate is above or below one or more different thresholds, with the difference between the urine output rate and hydration fluid rate increasing as the urine output rate increases. In such embodiments, the difference between the urine output rate and the hydration fluid rate can increase (with the urine rate being higher than the hydration fluid rate) as the urine output rate increases, and thus the net fluid loss from the patient can increase as the urine output rate increases.

At stage 208, the method 200 can include adjusting at least one of the dosage rate of the diuretic or the hydration rate of the hydration fluid, thereby causing net fluid loss from the patient. For example, the (i) diuretic dosage rate can be adjusted, (ii) the hydration rate can be adjusted, or (iii) the diuretic dosage rate and the hydration rate can both be adjusted. In some embodiments, the diuretic dosage rate is adjusted after the dosage determining phase of the treatment procedure is complete. As discussed above in stage 204, the dosage determining phase can end when (i) a predetermined amount of time has elapsed since the initial diuretic administration, and/or (ii) the urine output rate is or becomes greater than or equal to a predetermined threshold rate. The treatment procedure can then switch to a phase in which the diuretic dosage rate is adjusted to a dosage rate configured to maintain the patient's urine output rate at or above a desired output rate to cause net fluid loss (also known as a "continuous delivery phase" or "fluid reduction phase").

The adjusted diuretic dosage rate can be the initial dosage rate for the fluid reduction phase, and can be determined in many different ways. For example, the adjusted diuretic dosage rate can be based on the outcome of the dosage determining phase. The adjusted diuretic dosage rate can be less than or equal to the diuretic dosage rate at the end of the dosage determining phase (e.g., the dosage rate when the patient's urine output reaches or exceeds the target threshold). Decreasing the diuretic dosage rate can decrease the rate of increase in urine output rate (e.g., cause the patient's urine output to approach a constant or substantially constant rate) but without actually decreasing the urine output rate itself. Additionally or alternatively, the decrease in diuretic dosage rate can maintained the patient's urine output rate at a predetermined rate and/or within a predetermined range (e.g., no more than 5%, 10%, or 20% variability from a predetermined rate).

In some embodiments, the adjusted diuretic dosage rate is a predetermined percentage or fraction of the current dosage rate (e.g., the dosage rate at the end of the dosage determining phase) or a predetermined percentage of the cumulative diuretic dosage amount (e.g., the cumulative amount delivered during the dosage determining phase). For example, the adjusted dosage rate can be a predetermined percentage (e.g., 10%, 15%, 20%, 25%, 30%, or within a range of 10-30%) of a value of the total amount of diuretic delivered to the patient at that time. For example, if the total amount delivered is 100 mg, and the predetermined percentage is 25%, then the adjusted dosage rate can be 25 mg/hr. In some embodiments, the percentage used to calculate the adjusted diuretic dosage rate is based on a pharmacokinetic characteristic of the particular diuretic being infused. For example, the percentage can be 20% for furosemide, such that if 50 mg of furosemide is infused in 60 minutes, then the adjusted diuretic dosage rate can be 10 mg/hr.

In some embodiments, stage 208 includes delivering the diuretic at the adjusted diuretic dosage rate until the fluid reduction phase is complete, e.g., until a predetermined period of time has elapsed and/or until a target net fluid loss volume is achieved. During the fluid reduction phase, the diuretic dosage rate can be constant or substantially constant (e.g., no more than 5%, 10%, or 20% variability from the initially determined adjusted diuretic dosage rate). In other embodiments, however, stage 208 can include making additional adjustments to the diuretic dosage rate during the treatment procedure (e.g., increasing and/or decreasing the diuretic dosage rate). The adjustments can be based on whether one or more of a predetermined set of conditions is met, such as whether the urine output rate is too high. The set of conditions can include (i) an average urine rate being greater than a predetermined rate for a period of time, (ii) an average rate of change of the urine rate being greater than a predetermined rate of change, and/or (iii) a diuretic dosage rate being greater than a predetermined dosage rate. If some (e.g., two) or all of the conditions are met, the diuretic dosage rate can be decreased (e.g., by a predetermined amount or percentage), also referred to herein as "down-titration."

In some embodiments, a down-titration is performed only if all or a majority of the above conditions are met, which can avoid unnecessarily decreasing the diuretic dosage rate, thereby allowing urine output rates to remain high and avoiding unnecessary interruptions to the treatment procedure. For example, whereas other methodologies may interrupt fluid therapy and decrease the diuretic dosage rate (e.g., to zero mg/hr) when the urine rate is just too high, the process described herein can only decrease the dosage rate (e.g., to a non-zero or zero dosage rate) when the urine output rate is both high and continuing to increase. Stated differently, the process herein can prevent the diuretic dosage rate from being unnecessarily decreased when urine rates are temporarily high (e.g., above the predetermined rate), but are trending downward. This approach can prevent or inhibit over-diuresis, excess fluid loss and/or electrolyte loss, as well limit unnecessary exposure of the patient to additional diuretic. Additionally, because the diuretic dosage rate can be down-titrated, rather than stopping the diuretic entirely, the fluid therapy can continue (albeit at lower urine output rates) without needing to completely restart the procedure.

As another example, the additional adjustments to the diuretic dosage rate in stage 208 can include increasing the diuretic dosage rate, also referred to herein as "re-ramping" or "up-titration." In some embodiments, re-ramping is performed if urine output rates are too low, as determined based on a set of conditions. The set of conditions can include (i) the average urine rate being below a predetermined threshold rate for a predetermined period of time, and/or (ii) more than a predetermined amount of debt has accumulated over the predetermined period of time. "Debt" can be defined as the area on a plot between the urine output rate and a set rate (e.g., 325 ml/hr), and can represent how much of and for how long the urine output rate has been below the set rate. If some or all of the conditions are met, re-ramping can be performed by incrementally increasing the diuretic dosage rate until (i) a predetermined amount of time has elapsed, and/or (ii) the urine output rate is or becomes greater than or equal to a predetermined threshold rate. The re-ramp process can be identical or generally similar to the dosage determining process previously described in stage 204.

The re-ramping process can be performed automatically, semi-automatically, or manually. In some embodiments, re-ramping is a semi-automatic or manual process requiring user approval, e.g., for regulatory and/or safety reasons. In such embodiments, the system can output a notification to the user (e.g., via the display 150 of FIG. 1A) instructing the user to confirm that re-ramping should be initiated. Optionally, the system can implement a pre-approval procedure in which the user can allow the system to automatically perform re-ramping under certain conditions (e.g., within a specific time period, until a certain urine output volume and/or rate is achieved, for a maximum diuretic amount and/or dosage rate, etc.). This approach can allow for automatic re-ramping under limited circumstances, which can reduce the amount of human intervention during the treatment procedure and improve the responsiveness of the system to the patient's current state. Once the pre-approval conditions have elapsed, the user may need to provide re-approval before additional automatic re-ramping is allowed.

In some embodiments, stage 208 also includes adjusting the diuretic dosage rate in response to a detected blockage (e.g., an air lock, a kink in a fluid line, etc.) in the urine collection system. For example, an air lock can be any partial or complete obstruction of fluid flow due to trapped gas (e.g., air) within a fluid system. Examples of situations where air locks may arise are described further below in connection to FIGS. 6A and 6B. As described elsewhere herein, air locks may produce an artificial drop in urine output rates, which can affect the determination of the diuretic dosage rate (e.g., result in a diuretic dosage rate that is too high). In some embodiments, the presence of an air lock is detected based on a period of little or no urine output (due to the air lock blocking urine flow), followed by a sudden large bolus of urine output (due to built-up pressure in the fluid line clearing the air lock). When the system detects that an air lock or other blockage was or is present, the system can compensate by adjusting the diuretic dosage rate to the dosage rate that should have been used if the air lock or other blockage had not occurred. The appropriate dosage rate can be determined based on historical data (e.g., the diuretic dosage rate before the air lock occurred, a diuretic dosage rate calculated from the patient's urine output rate before the air lock occurred, etc.).

Alternatively or in combination, stage 208 can include adjusting the hydration rate, e.g., by increasing or decreasing the hydration rate based on the patient's urine output rate to drive net fluid loss from the patient. For example, as previously described, the hydration rate can initially match the patient's urine output rate for a set of initial conditions (e.g., certain time period, initial urine output amount, and/or initial urine output rate). Once the initial conditions have elapsed, the hydration rate can be maintained at a rate lower than the urine output rate (e.g., a percentage of the urine output rate) so the patient exhibits net fluid loss during the fluid reduction phase. The hydration rate can be determined in various ways, such as a percentage or fraction of the patient's urine output rate, based on whether the urine output rate is above or below a number of different thresholds (e.g., with the difference between the urine output rate and hydration rate increasing as the urine output rate increases), and/or any other suitable approach.

Optionally, the diuretic dosage rate and/or hydration rate can be adjusted based on factors other than patient's urine output rate. For example, the diuretic dosage rate and/or hydration rate can be adjusted based on the patient's blood pressure in order to avoid placing the patient in a hypotensive state. In some embodiments, if the patient's blood pressure level is too low (e.g., below a threshold value or range), the system can avoid increasing the diuretic dosage rate and/or can decrease the diuretic dosage rate for a certain period of time. Alternatively or in combination, the system can increase the hydration rate (e.g., to the maximum allowable hydration rate and/or to provide a desired fluid replacement profile (e.g., a 100% match to the patient's urine output rate)) for a certain period of time if low blood pressure levels are detected. The system can also output an alert indicating that the patient's blood pressure level is low so a user can check on the patient's status. Optionally, the system can take both blood pressure levels and urine output rates into account, e.g., the system can generate alerts and/or can adjust the diuretic dosage rate and/or hydration rate if the patient's blood pressure is low and the patient's urine output rate drops. This approach can improve patient safety and control over the treatment procedure.

In some embodiments, some or all of the stages of the method 200 are performed as part of a medical procedure for treating the patient for a fluid overload condition. The method 200 can be used as a primary, standalone therapy for treating fluid overload, or can be used in combination with other therapies (e.g., as a post-primary therapy to reduce the likelihood of re-hospitalization). The method 200 can be performed in any suitable setting, such as an inpatient setting or an outpatient setting. In embodiments where the method 200 is performed as an outpatient therapy, the overall duration of the method 200 can be reduced (e.g., to no more than 10 hours, 5 hours, 4 hours, 3 hours, 2 hours, or 1 hour).

The method 200 illustrated in FIG. 2 can be modified in many different ways. For example, any of the stages of the method 200 can be omitted, such as stages 204 or 206. In some embodiments, stage 204 is omitted so that the method 200 controls hydration fluid infusion but not diuretic delivery, or so that the method 200 does not involve any diuretic delivery at all. Similarly, stage 206 can be omitted so that the method 200 controls diuretic delivery but not hydration fluid infusion, or so that the method 200 does not involve any hydration fluid infusion at all. As another example, some or all of the stages 200 of the method 200 can be performed in a different order and/or repeated (e.g., any of stages 202, 204, 206, and/or 208). In a further example, the method 200 can optionally include additional stages not shown in FIG.

2 (e.g., causing delivery of additional medications, obtaining parameters other than urine output rate, etc.).

The present technology can provide many advantages for treating fluid overload and/or managing patient fluid levels. For example, embodiments of the present technology have been shown to consistently reduce the fluid volume in patients faster and safer than conventional treatment systems and methods. For example, whereas conventional methods can typically take at least five days to remove 4-5 L of net fluid volume, embodiments of the present technology have been shown to remove 4-5 L liters of net fluid volume in no more than 24 hours. Additionally, embodiments of the present technology have also been shown to remove significant amounts of salt via high sodium urine from patients. This can reduce the likelihood of the patient reaccumulating fluid after discharge, which can lead to reductions in rehospitalization rates. Moreover, embodiments of the present technology can automatically and continuously monitor urine output, hydration fluid infusion, and/or diuretic delivery to mitigate patient safety concerns (e.g., over-diuresis and/or hypotension) during the treatment procedure.

Embodiments of the present technology can provide various benefits, such as any of the following: (i) optimizing net fluid volume removal; (ii) reducing the time needed to achieve desired net fluid removal by allowing physicians to use higher diuretic dosages and/or dosage rates earlier in treatment compared to conventional treatments; (iii) avoiding or reducing risk of adverse events such as over-diuresis, dehydration, and/or intravascular depletion; (iv) quickly assessing if a patient is diuretic resistant; and (v) providing a record of treatment data. Embodiments of the present technology may obtain an average net fluid removal rate (e.g., average urine output rate minus average hydration fluid infusion rate) of at least 225 ml/hr, which provides 3.4 L per day of net fluid volume removal based on introducing 2 L of fluid per day orally or through IV infusion. This rate of fluid removal, while replacing sodium, may reduce the overall length of stay and/or provide enhanced decongestion.

II. URINE COLLECTION SYSTEMS AND ASSOCIATED DEVICES AND METHODS

FIGS. 3-8 and the accompanying description provide various examples of urine collection systems, and associated devices and methods, that are suitable for use with the fluid management system 100 of FIG. 1A and/or the method 200 of FIG. 2. Any of the features of the embodiments of FIGS. 3-8 can be combined with each other and/or incorporated into any of the other embodiments of the present technology. For example, any of the embodiments of FIGS. 3-8 can be combined with and/or incorporated into the urine system 110 of FIG. 1A.

A. Systems, Devices, and Methods with Multiple Urine Collection Containers

Figure 3:
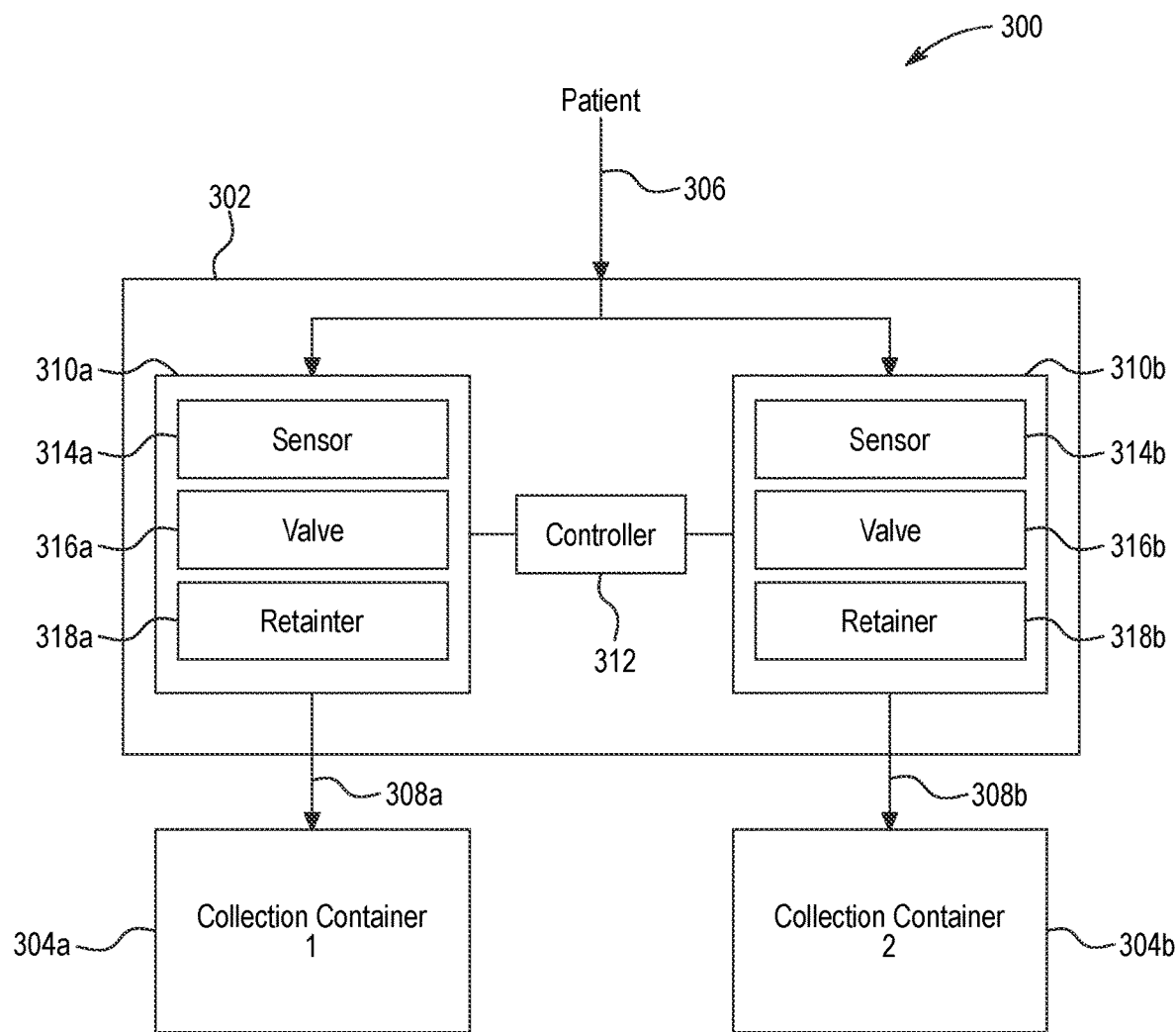
FIG. 3 is a schematic diagram of a urine collection system, in accordance with embodiments of the present technology.
Figure 4A:
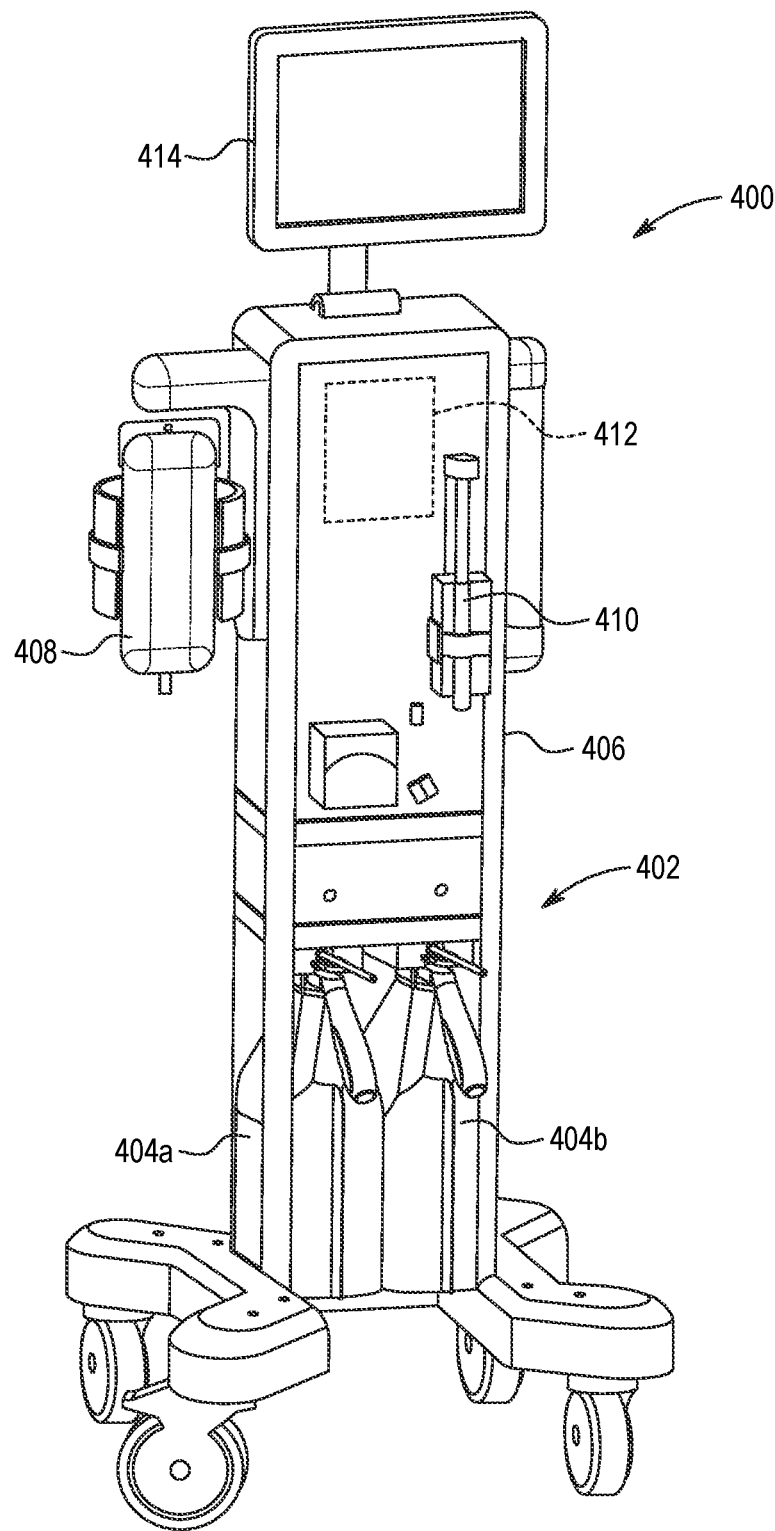
FIGS. 4A-4J illustrate a representative example of a urine collection system, in accordance with embodiments of the present technology.
Figure 4B:
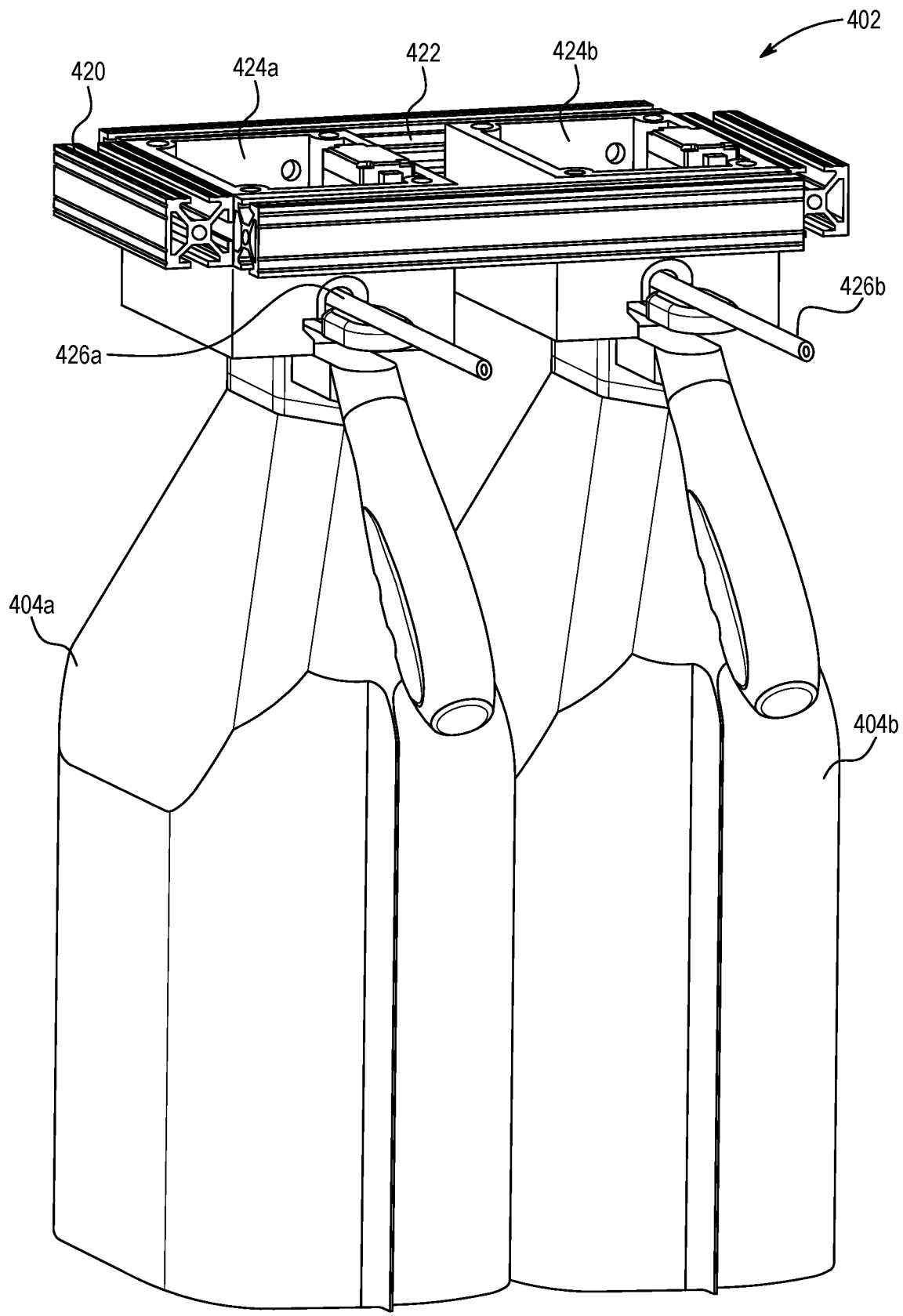
Figure 4C:
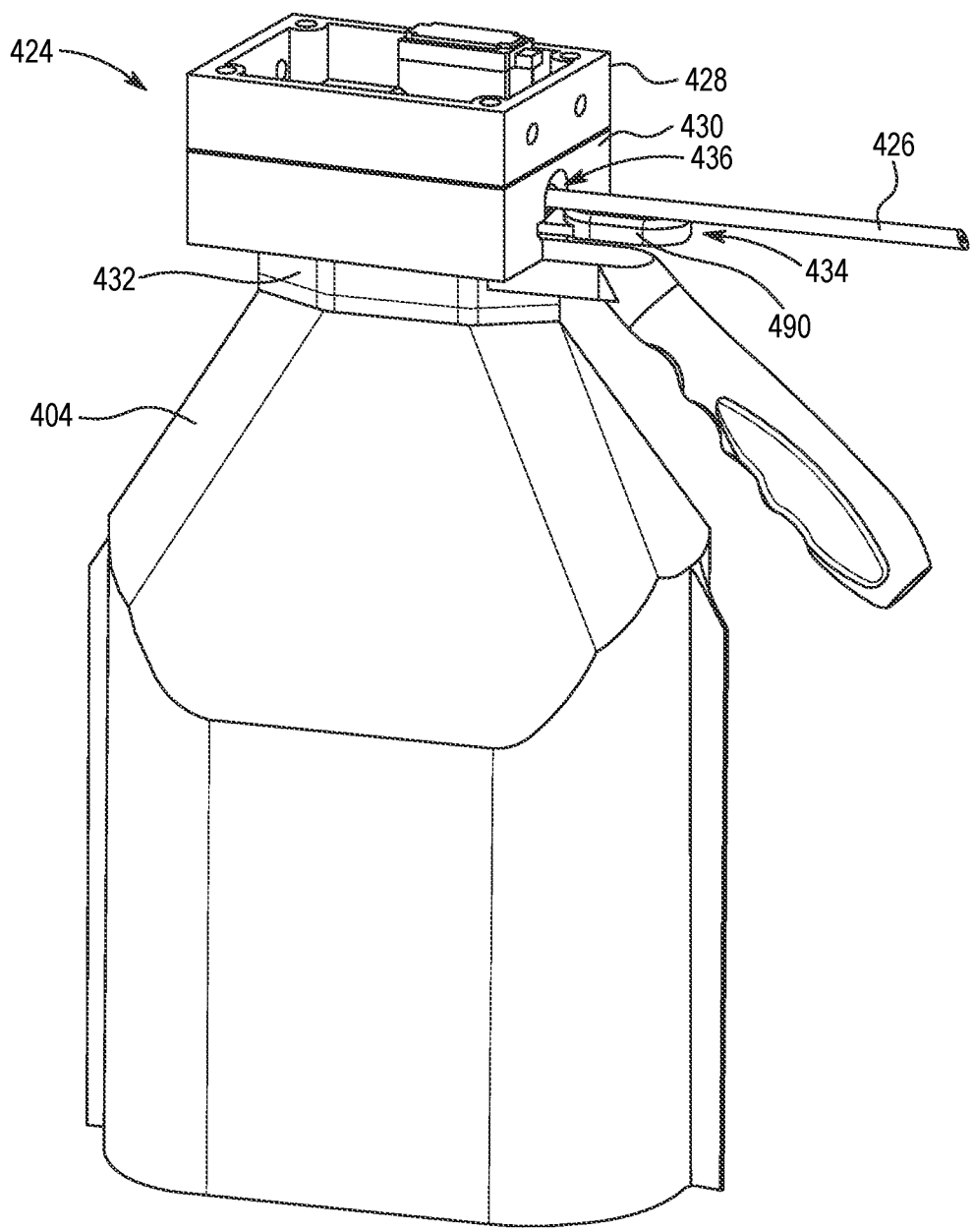
Figure 4D:
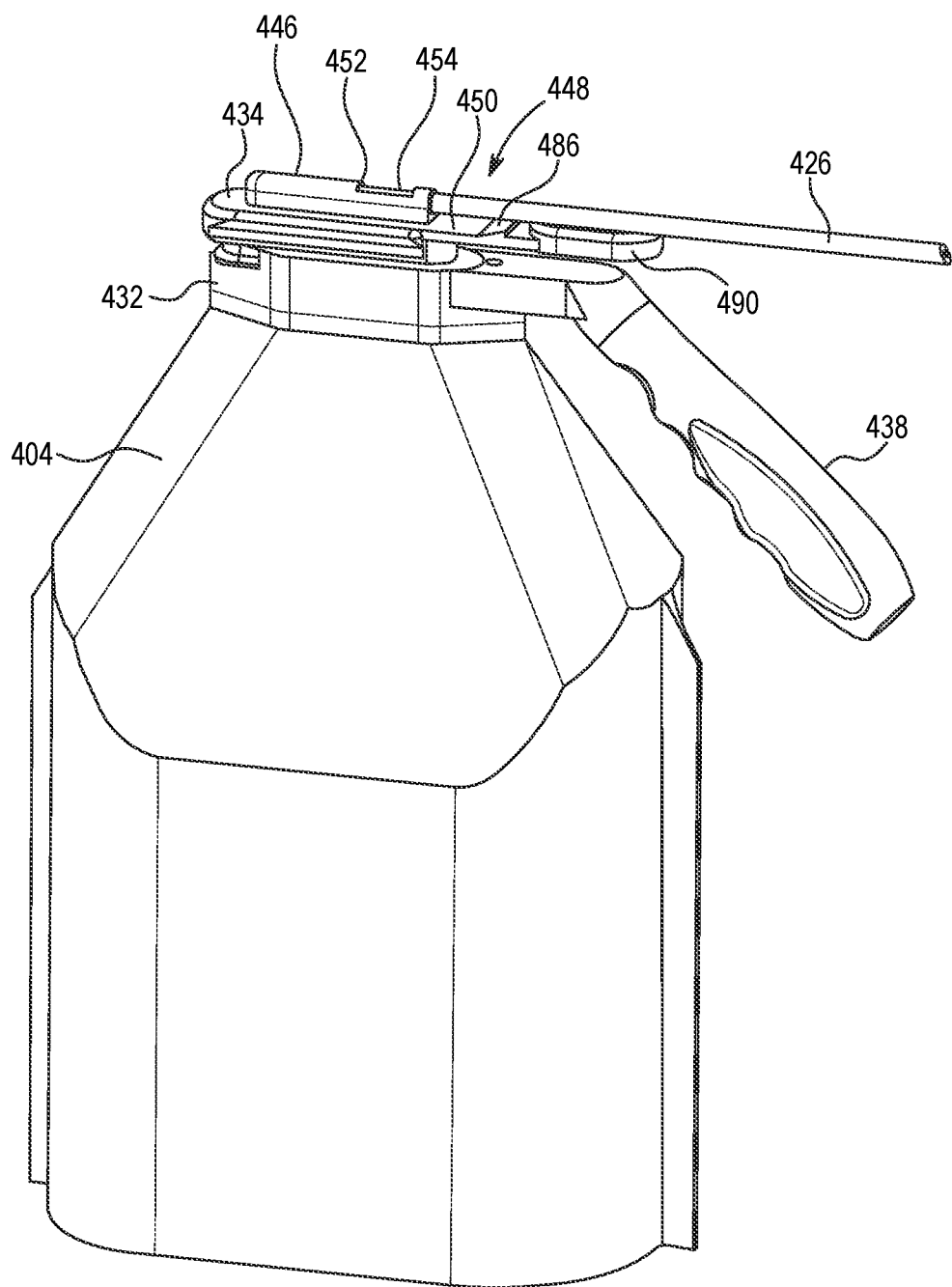
Figure 4E:
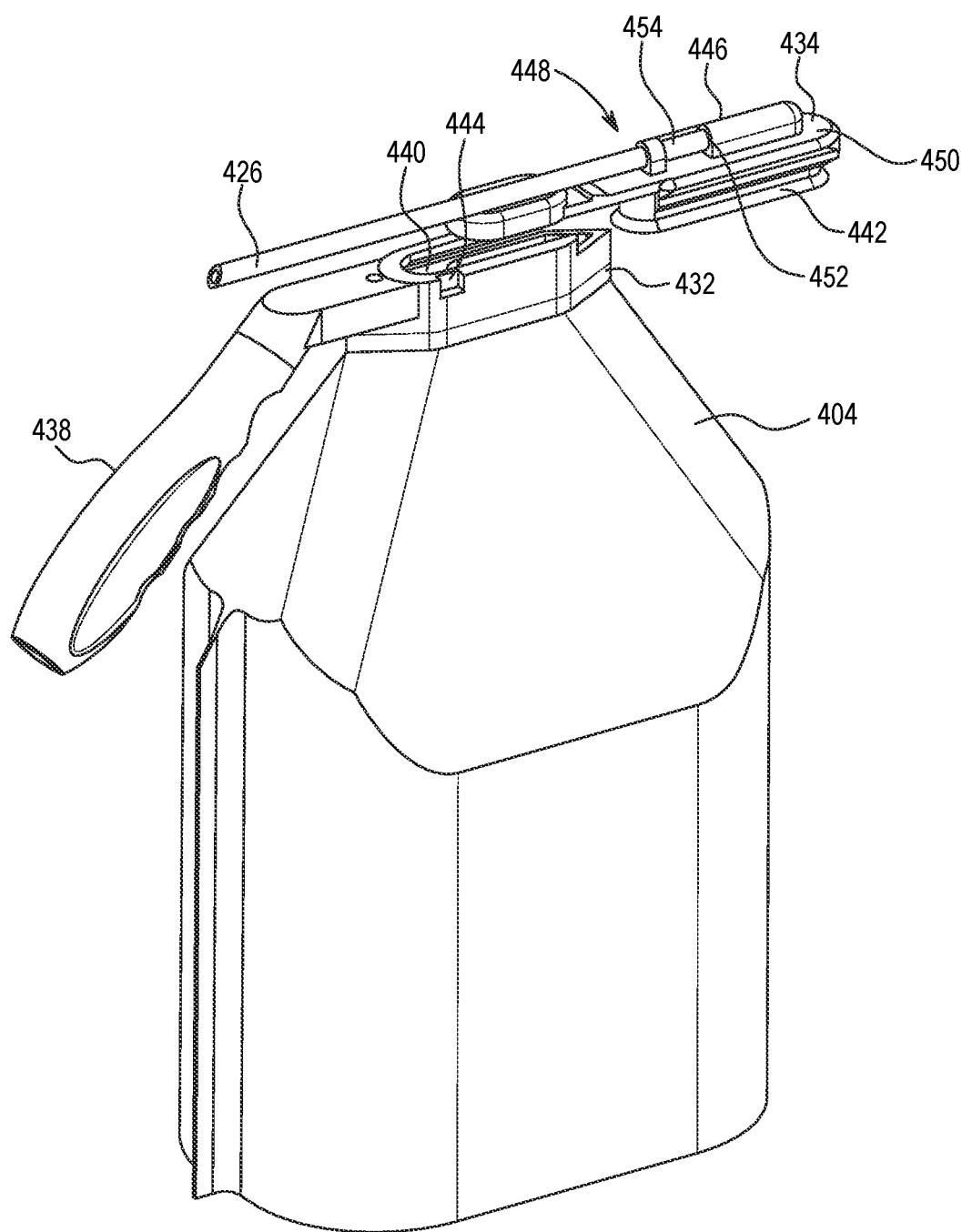
Figure 4F:
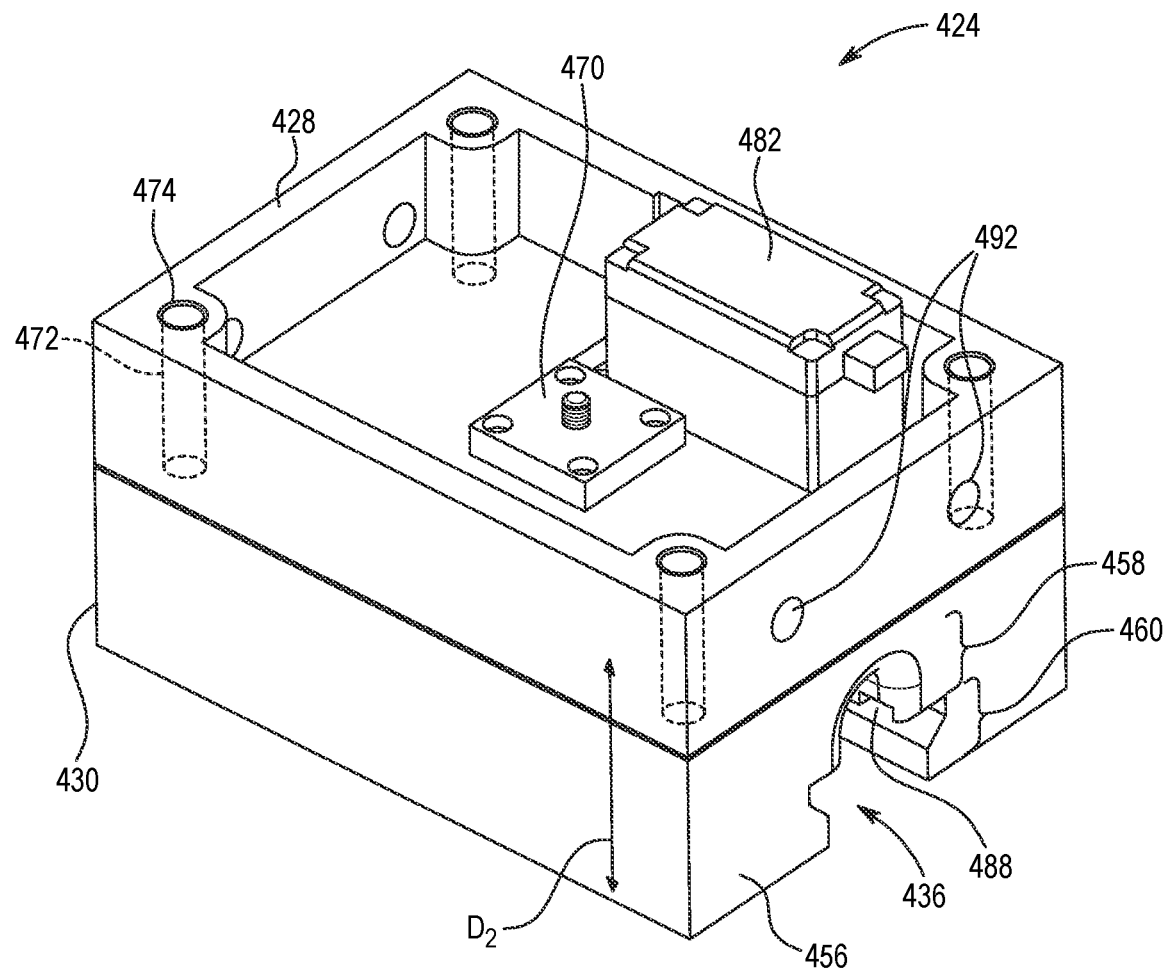
Figure 4G:
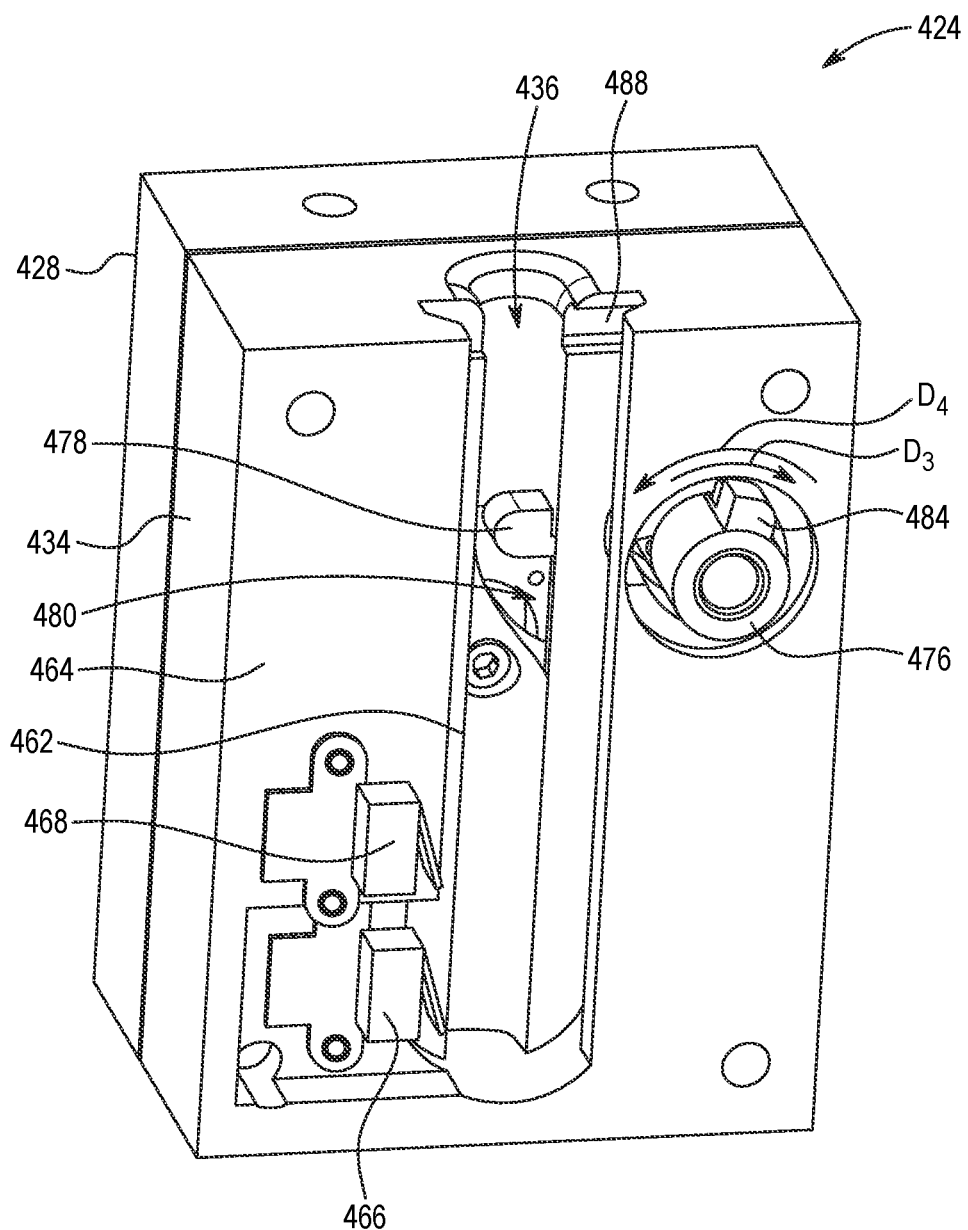
Figure 4H:
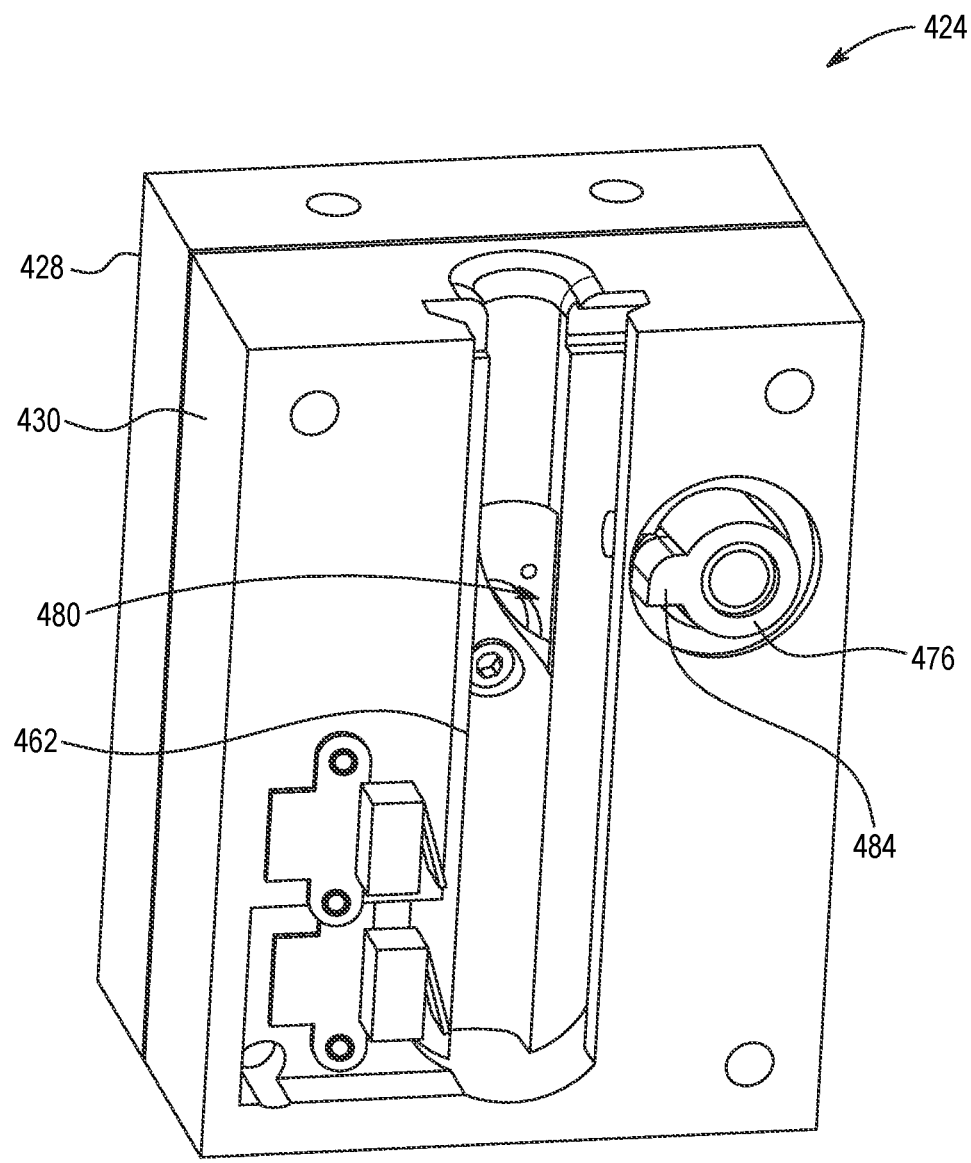
Figure 4I:
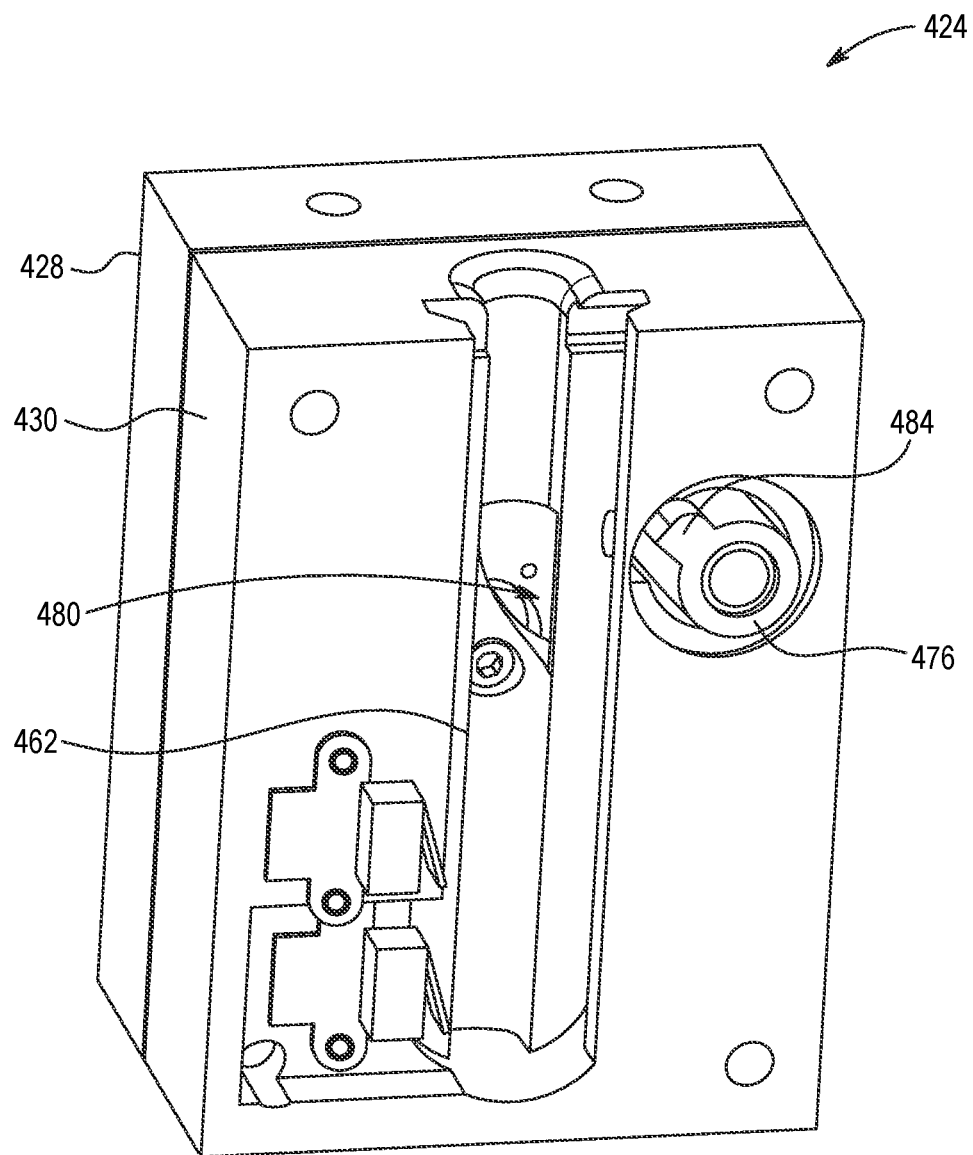
Figure 4J:
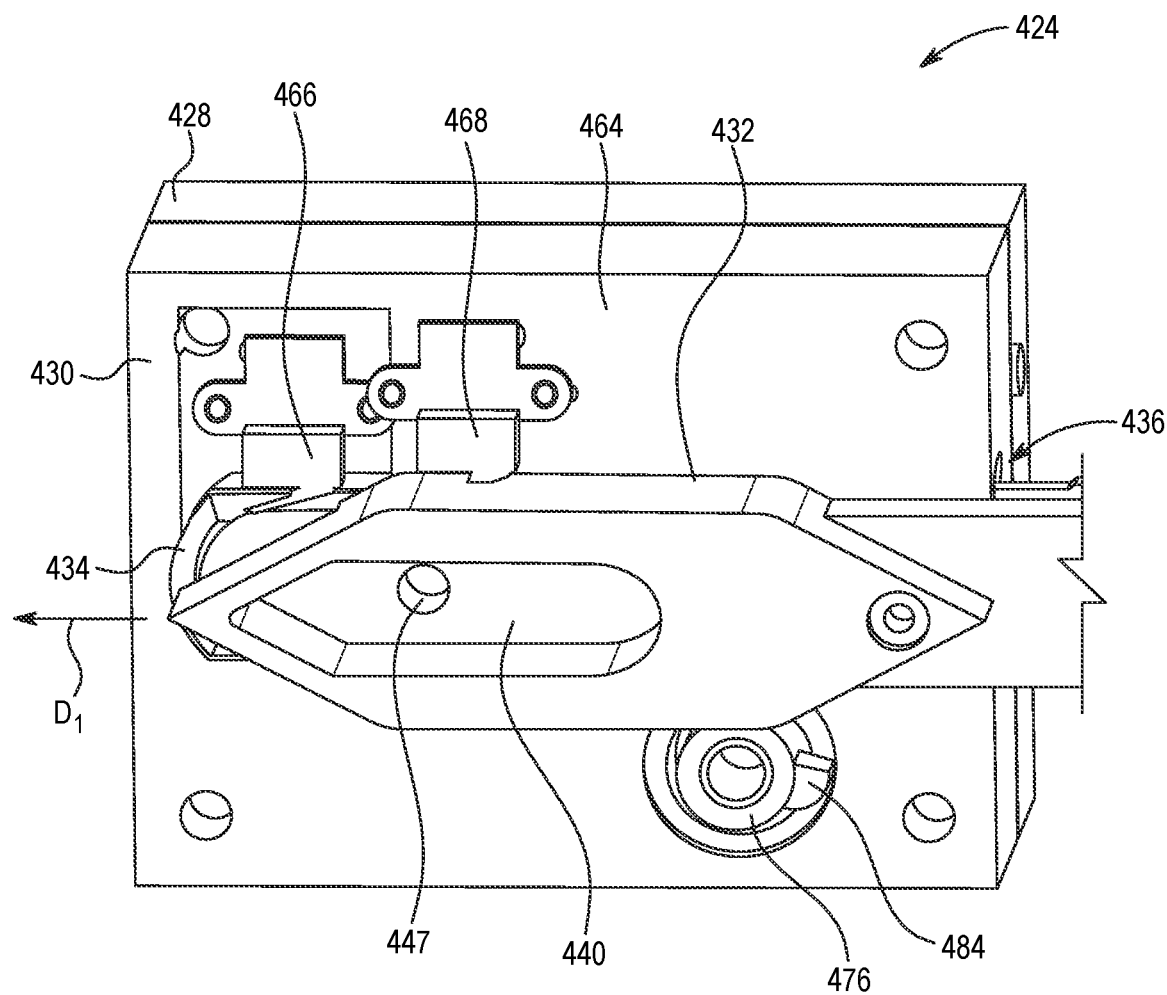

FIGS. 3-4J illustrate various examples of urine collection systems configured in accordance with embodiments of the present technology. Specifically, FIG. 3 provides a general overview of the components of a urine collection system, and FIGS. 4A-4J provide a representative example of a urine collection system. Any of the features of the embodiments of FIGS. 3-4J can be combined with each other and/or with any of other systems and devices described herein (e.g., the system 100 of FIG. 1A).

FIG. 3 is a schematic diagram of a urine collection system 300 configured in accordance with embodiments of the present technology. The system 300 can be used to collect urine from a patient during a medical procedure in which the patient is expected to output a large total volume of urine (e.g., at least 2 L, 5 L, 10 L, 15 L, or 20 L of urine within a 24-hour period) and/or exhibit high urine output rates (e.g., at least 0.5 L/hr, 1 L/hr, 1.5 L/hr, 2 L/hr or 2.5 L/hr). In other embodiments, however, the system 300 can be used in any procedure involving collecting urine from a patient and/or monitoring the patient's urine output.

The system 300 includes a flow control assembly 302 operably coupled to a plurality of urine collection containers. In the illustrated embodiment, for example, the system 300 includes a first collection container 304a and a second collection container 304b for receiving urine or other body fluids. In other embodiments, however, the system 300 can include a different number of containers 304a-b, such as three, four, five, or more containers 304a-b. The containers 304a-b can be any suitable flexible or rigid receptacle for holding urine from a patient, such as bags, bottles, cans, vials, etc. Each of the containers 304a-b can have an interior volume of at least 0.5 L, 1 L, 1.5 L, 2 L, or 5 L.

The flow control assembly 302 is configured to direct urine from the patient into one or more of the containers 304a-b. As shown in FIG. 3, the system 300 receives urine from a patient via an intake fluid line 306, which can be coupled to the patient's body via a catheter (e.g., a Foley catheter, Texan Condom catheter, PureWick catheter, etc.). The intake fluid line 306 can connect to multiple fluid lines (e.g., first fluid line 308a and second fluid line 308b) that each connect to one of the containers 304a-b. In the illustrated embodiment, for example, the first fluid line 308a connects the first container 304a to the intake fluid line 306, and the second fluid line 308b connects the second container 304b to the intake fluid line 306. In other embodiments, the system 300 can include a different number of fluid lines, depending on the number of containers 304a-b used.

In some embodiments, the flow control assembly 302 includes a first subassembly 310a and a second subassembly 310b configured to control fluid flow from the patient to the first and second containers 304a-b, respectively. The first subassembly 310a can be operably coupled to the first container 304b and/or first fluid line 308a, and the second subassembly 310b can be operably coupled to the second container 304b and/or second fluid line 308b. Each of the subassemblies 310a-b can include various components for controlling and/or monitoring urine output to the respective container 304a-b, such as one or more sensors, valves, and/or retainers, as described in detail further below. The flow control assembly 302 can also include a controller 312 (e.g., a microprocessor) operably coupled to the subassemblies 310a-b to control the operations thereof. The controller 312 can receive and process data from the subassemblies 310a-b, transmit control signals to the subassemblies 310a-b, and/or transmit data to a separate device (e.g., a user device such as a smartphone, the controller 140 of FIG. 1A, etc.). Additional details of the operation of the controller 312 are provided below.

The sensors (e.g., first sensor 314a and second sensor 314b) can be or include any device configured to measure an amount of urine in and/or a rate of urine flow to the corresponding container 304a-b. For example, the sensors 314a-b can include weight sensors, flow sensors, fluid level sensors, float sensors, optical sensors, drip counters, or the like. The sensors 314a-b can be included in or coupled to the containers 304a-b, fluid lines 308a-b, and/or any other suitable portion of the system 300. The controller 312 can receive and process the sensor data generated by the sensors 314a-b to calculate an amount of urine within each container 304a-b and/or a rate of urine flow to each container 304a-b. Based on the calculations, the controller 312 can assess the status of each container 304a-b (e.g., full, partially full, empty) and determine whether the container 304a-b is available to hold urine, needs to be emptied, etc.

The valves (e.g., first valve 316a and second valve 316b) can be or include any device configured to control fluid flow to the respective container 304, such as pinch valves, ball valves, butterfly valves, diaphragm valves, check valves, and the like. Each valve 316a-b can be coupled to an actuator (e.g., a servomotor—not shown in FIG. 3) that actuates the valve 316a-b between an open configuration permitting fluid flow, and a closed configuration preventing fluid flow. The controller 312 can be operably coupled to the actuator to control whether the corresponding valve 316a-b is open or closed. Accordingly, by selectively opening and closing the valves 316a-b, the controller 312 can direct the urine flow from the patient to a particular container 304a-b and/or prevent urine from entering a particular container 304a-b.

The retainers (e.g., first retainer 318a and second retainer 318b) can be or include any device configured to secure the corresponding container 304a-b to the flow control assembly 302, such as latches, fasteners, etc. The retainers 318a-b can prevent the containers 304a-b from being inadvertently removed or dislodged during a procedure, thus reducing the likelihood of spills or leaks. Each retainer 318a-b can be coupled to an actuator (not shown in FIG. 3) that actuates the retainer 318a-b between an unlocked configuration and a locked configuration. For example, the controller 312 can be operably coupled to the actuator to control whether the corresponding retainer 318a-b is locked or unlocked. The controller 312 can coordinate the state of each retainer 318a-b with the corresponding valve 316a-b. For example, if the first valve 316a is open so that urine is flowing into the first container 304a, the controller 312 can lock the first retainer 318a so the first container 304a cannot be removed. As another example, if the second valve 316b is closed so that no urine is flowing into the second container 304b, the controller 312 can unlock the second retainer 318b to permit removal of the second container 304b (e.g., in order to empty the second container 304b). Alternatively or in combination, the first and second retainers 318a-b can be manually actuated by a user (e.g., in response to a notification or alarm via a light, sound, message, etc.). In other embodiments, however, the first and second retainers 318a-b are optional and can be omitted.

The system 300 of FIG. 3 can be configured in many different ways. For example, although the illustrated embodiment shows two separate subassemblies 310a-b, in other embodiments, the subassemblies 310a-b can be combined into a single component. Additionally, although FIG. 3 illustrates a single controller 312, in other embodiments, the controller 312 can be implemented as multiple discrete controllers (e.g., one controller per subassembly 310). Optionally, the controller 312 can be located partially or entirely outside the flow control assembly 302 (e.g., as part of a console for a larger patient fluid management system). For example, the controller 312 can be the controller 140 of the system 100 of FIG. 1A. The locations of the various components shown in FIG. 3 can also be varied as desired. For example, the sensors 314a-b can be within or on any of the containers 304a-b, within or on any of the fluid lines 308a-b, or at any other suitable location within the system 300. Additionally, the system 300 can include a different number of containers 304a-b, subassemblies 310a-b, sensors 314a-b, valves 316a-b, and/or retainers 318a-b.

FIGS. 4A-4J illustrate a representative example of urine collection system 400 configured in accordance with embodiments of the present technology. More specifically, FIG. 4A is a perspective view of the system 400, and FIGS. 4B-4J are various views of a flow control assembly 402 of the system 400.

Referring first to FIG. 4A, the system 400 includes a flow control assembly 402 operably coupled to a first container 404a and a second container 404b. The flow control assembly 402 can monitor and/or control urine flow from a patient into the containers 404a-b, as described in greater detail below. The system 400 can include additional functional components, such as any of the components for monitoring and/or managing fluid levels previously described with reference to FIG. 1A. In the illustrated embodiment, for example, the system 400 is configured as a console 406 including the flow control assembly 402, a hydration system for delivering a fluid (e.g., a saline solution) from a fluid source 408, a diuretic system for delivering a diuretic from a diuretic source 410, and a computer or controller 412 (shown schematically), and a user input/output device (e.g., a touchscreen or display 414). As shown in FIG. 4A, the containers 404a-b can be at the lower portion of the console 406 and/or relatively close to the floor. This arrangement can create a stronger siphon vacuum in the fluid line(s) connected to the patient, which can improve urine collection by decreasing pooling of fluid in the bladder, avoiding large boluses of urine when the patient moves, and/or reducing the likelihood of air lock by clearing small air bubbles in the fluid line(s). In other embodiments, however, the components of the console 406 can be arranged differently, or can be omitted.

FIG. 4B is a perspective view of the flow control assembly 402 together with the containers 404a-b. The flow control assembly 402 can include a frame 420 configured to connect the containers 404a-b to the console 406 (FIG. 4A). The containers 404a-b can each be flexible bags, rigid bottles, or any other suitable structure for holding urine (e.g., as previously described with reference to FIG. 3). In the illustrated embodiment, the frame 420 is configured as a generally rectangular support structure with an opening 422 for receiving a first subassembly 424a and a second subassembly 424b. The first subassembly 424a can be coupled to the first container 404a to control urine flow into the first container 404a via a first fluid line 426a, and the second subassembly 424b can be coupled to the second container 404b to control urine flow into the second container 404b via a second fluid line 426b. The first and second fluid lines 426a-b can be fluidly coupled to an intake fluid line (not shown) via a fitting (e.g., a Y-fitting), manifold, or other suitable connector. The subassemblies 424a-b can include sensors, valves, retainers, etc., for monitoring and/or controlling urine flow into the respective containers 404a-b, as previously discussed with reference to FIG. 3.

FIGS. 4C-4J are various views of an individual container 404 and subassembly 424 of the flow control assembly 402. Any of the features of the container 404 can be incorporated in the first container 404a and/or the second container 404b of FIGS. 4A and 4B, and any of the features of the subassembly 424 can be incorporated in the first and/or second subassemblies 424a-b of FIGS. 4A and 4B.

Referring first to FIG. 4C, which is a perspective view of the container 404 together with the subassembly 424, the subassembly 424 is configured to connect the container 404 to the rest of the flow control assembly 402. The subassembly 424 can monitor and/or control fluid flow through a fluid line 426 into the container 404. As shown in FIG. 4C, the subassembly 424 can include an upper section 428 and a lower section 430. Although the upper and lower sections 428, 430 are depicted as having a generally rectangular shape, in other embodiments, the upper and/or lower sections 428, 430 can have a different shape (e.g., square, oval, etc.). The upper section 428 can be a mounting plate for attaching to the frame 420 of the flow control assembly 402 (FIG. 4B), while the lower section 430 can be a nest or receptacle for receiving and supporting the container 404. The lower section 430 can connect to any suitable portion of the container 404, such as a cap 432 on the upper portion of the container 404. In the illustrated embodiment, the cap 432 is coupled to an interface cartridge 434, and the interface cartridge 434 fits within an aperture 436 in the lower section 430 of the subassembly 424.

FIG. 4D is a left perspective view of the interface cartridge 434 attached to the container 404, and FIG. 4E is a right exploded perspective view of the interface cartridge 434 and container 404. Referring first to FIG. 4D, the interface cartridge 434 is configured to removably couple to the container 404 via the cap 432, which can be a rigid structure connected to or integrally formed with the upper end of the container 404. Optionally, the cap 432 can include a handle 438 with ergonomic features (e.g., texturing, ridges, etc.) so the user can grasp the handle 438 to insert, remove, carry, and/or otherwise manipulate the container 404.

Referring next to FIG. 4E, the cap 432 includes an opening 440 allowing fluid flow into the container 404. The interface cartridge 434 can fit at least partially into the opening 440 in the cap 432 to provide a fluid-tight seal. In the illustrated embodiment, the opening 440 has an elongate shape, and the interface cartridge 434 includes a corresponding elongate bottom section 442 that mates with the opening 440. The cap 432 and/or interface cartridge 434 can be secured to each other via any suitable technique, such as interference fit, snap fit, latches, fasteners, magnetic elements, and so on. The coupling between the cap 432 and interface cartridge 434 can be a temporary, releasable connection such that the user can separate the cap 432 and container 404 from the interface cartridge 434 by pulling on the handle 438 of the cap 432. The cap 432 can also include at least one slot or recess 444 configured to secure the cap 432 and container 404 to the subassembly 424, as described in detail below in connection with FIGS. 4G-4J.

The interface cartridge 434 can fluidly couple the fluid line 426 to the container 404. In the illustrated embodiment, the interface cartridge 434 includes a receptacle 446 that receives a proximal portion 448 of the fluid line 426. The receptacle 446 can be a hollow structure or housing located on an upper surface 450 of the interface cartridge 434. To allow fluid to flow from the proximal portion 448 of the fluid line 426 into the container 404, the interface cartridge 434 can include a channel or hole 447 (shown in FIG. 4J) extending from the receptacle 446 and through the elongate bottom section 442. Accordingly, when the interface cartridge 434 is assembled onto the cap 432 (shown in FIG. 4D), fluid in the fluid line 426 can flow through the channel 447 of the interface cartridge 434 and into the opening 440 of the container 404.

Referring again to FIG. 4D, in some embodiments, the receptacle 446 includes a window 452 (e.g., aperture, cutout, etc.) exposing a section 454 of the proximal portion 448 of the fluid line 426. The exposed section 454 of the fluid line 426 can interface with a corresponding valve in the subassembly 424 (FIG. 4C) to control fluid flow into the container 404, as described in detail below with reference to FIGS. 4G-4J.

FIG. 4F is a top perspective view of the subassembly 424, FIGS. 4G-4I are bottom perspective views of the subassembly 424, and FIG. 4J is a bottom perspective view of the subassembly 424 connected to the cap 432 and interface cartridge 434. Referring first to FIG. 4F, the lower section 430 of the subassembly 424 can include a front surface 456 with an aperture 436 for receiving at least a portion of the interface cartridge 434. The shape of the aperture 436 can be complementary to the shape of the interface cartridge 434. For example, in FIG. 4F, the aperture 436 includes an upper portion 458 configured to accommodate the receptacle 446 and/or fluid line 426 of the interface cartridge 434 (FIGS. 4D and 4E), and a lower portion 460 configured to accommodate the upper surface 450 and at least part of the bottom section 442 of the interface cartridge 434 (FIGS. 4D and 4E). As shown in FIG. 4G, the aperture 436 can be connected to a cavity 462 in a bottom surface 464 of the lower section 430. The cavity 462 can have an elongate shape that is similar to the shape of the interface cartridge 434 so the interface cartridge 434 can fit at least partially into the cavity 462.

Referring next to FIG. 4J, the lower section 430 of the subassembly 424 can engage the interface cartridge 434 and cap 432 to secure the container 404 to the subassembly 424 (the container 404 is omitted from FIG. 4J for purposes of simplicity). To connect the container 404 to the subassembly 424, the user can slide the interface cartridge 434 and cap 432 along the bottom surface 464 of the lower section 430 (e.g., along direction $D_1$), so that the interface cartridge 434 passes through the aperture 436 and at least partially into the cavity 462.

The lower section 430 can additionally include at least one sensor configured to detect whether the container 404 is present (e.g., connected to the lower section 430). The sensor(s) can be or include any of the following: a mechanical sensor (e.g., a switch); an optical sensor; a sensor configured to detect a signal from a tag on the container 404, cap 432, and/or interface cartridge 434 (e.g., an RFID reader); or suitable combinations thereof. In the illustrated embodiment, for example, the lower section 430 includes a first sensor 466 configured to detect the presence of the interface cartridge 434, and a second sensor 468 configured to detect the presence of the cap 432 (which can serve as a proxy for the presence of the container 404). The first sensor 466 can be a first mechanical sensor (e.g., a first microswitch) that is actuated (e.g., depressed) when the interface cartridge 434 is within the cavity 462 (e.g., completely inserted into the cavity 462). Similarly, the second sensor 468 can be a second mechanical sensor (e.g., a second microswitch) that is actuated (e.g., depressed) when the cap 432 is positioned adjacent or near the bottom surface 464 of the lower section 430. The first and second sensor 466, 468 can operate independently so the flow control assembly 402 can determine whether the interface cartridge 434, the container 404, or both have been removed from the subassembly 424. The first and second sensors 466, 468 can each be at or near the end of the cavity 462 away from the aperture 436 so that the sensors 466, 468 are actuated only when the interface cartridge 434 and cap 432 are properly engaged with the cavity 462. In other embodiments, the first and/or second sensors 466, 468 can be at a different location on the lower section 430 (e.g., a different location relative to the cavity 462), can be located on the upper section 428 instead of the lower section 430, or can be omitted altogether.

Referring again to FIG. 4F, the subassembly 424 can further include at least one sensor configured to monitor an amount of fluid in the container 404 and/or a rate of fluid flow into the container 404. The sensor(s) can be or include any of the sensors discussed above with reference to FIG. 3, such as weight sensors, flow sensors, fluid level sensors, float sensors, optical sensors, drip counters, or the like. In the illustrated embodiment, for example, the upper section 428 includes a weight sensor 470 (e.g., a load cell) configured to measure the weight of the container 404 when the container 404 is coupled to the lower section 430. The lower section 430 can be connected to the upper section 428 via a slidable connection so the lower section 430 can translate up and/or down (e.g., along vertical axis $D_2$) relative to the upper section 428. As shown in FIG. 4F, the lower section 430 can include one or more pins 472 (shown in broken lines) that slidably fit within corresponding holes 474 in the upper section 428. Accordingly, when the container 404 is attached the lower section 430, the weight of the container 404 can displace the lower section 430 downward. The weight sensor 470 can be coupled to the lower section 430 such that the downward displacement of the lower section 430 applies a force against the weight sensor 470, which can output a sensor signal in response to the applied force that is indicative of the weight of the container 404.

The fit between the upper and lower sections 428, 430 can be sufficiently tight for facilitating removal and insertion of the container 404 and/or interface cartridge 434, while also being sufficiently loose for providing accurate weight measurements. For example, if the fluid distribution in the container 404 is off-center, an excessively tight fit between the upper and lower sections 428, 430 may produce uneven loading and/or drag on the pins 472, which can interfere with the measurements generated by the weigh sensor 470. Accordingly, the subassembly 424 can optionally include an adjustment mechanism that can vary the fit between the upper and lower sections 428, 430. In some embodiments, when the container 404 and/or interface cartridge 432 are being removed from and/or inserted into the subassembly 424, the adjustment mechanism tightens the fit between the upper and lower sections 428, 430 to facilitate removal and/or insertion. When the container 404 and/or interface cartridge 432 are connected to the subassembly 424, the adjustment mechanism can loosen the fit between the upper and lower sections 428, 430 so that the lower section 430 hangs freely from the weight sensor 470, with little or no contact with the pins 472. Optionally, the adjustment mechanism can also automatically lock the container 404 and/or interface cartridge 432 to the subassembly 424 while the upper and lower sections 428, 430 are loosely engaged. The adjustment mechanism can include any suitable combination of actuators, latches, etc., and can be operated manually by the user, automatically by a controller, or any suitable combination thereof.

Referring again to FIG. 4G, the subassembly 424 also includes at least one valve for controlling fluid flow to the container 404. The valve(s) can be or include any of the embodiments discussed above with reference to FIG. 3, such as such as pinch valves, ball valves, butterfly valves, diaphragm valves, check valves, etc. In the embodiment of FIG. 4G, the lower section 430 includes a cam unit 476 having an elongate arm 478 that serves as a pinch valve. The cam unit 476 can be located near the cavity 462 and/or an access slot 480 connected to the cavity 462, such that rotation of the cam unit 476 moves the elongate arm 478 through the access slot 480, and thus into and/or out of the cavity 462. For example, the cam unit 476 can rotate clockwise (e.g., along direction $D_3$) to move the elongate arm 478 into the cavity 462, and can rotate counterclockwise (e.g., along direction $D_4$) to move the elongate arm 478 out of the cavity 462. The subassembly 424 can also include an actuator 482 (e.g., a servomotor—FIG. 4F) operably coupled to the cam unit 476 to actuate the rotation of the cam unit 476. The actuator 482 can be in the upper section 428, lower section 430, or any other suitable location in the subassembly 424.

In some embodiments, the cam unit 476 is configured to rotate between a plurality of different positions to control fluid flow into the container 404. For example, the cam unit 476 can rotate between a first position allowing fluid flow into the container 404, and a second position reducing or preventing fluid flow into the container 404. When the cam unit 476 is in the second position (e.g., as shown in FIG. 4G), the elongate arm 478 can extend into the cavity 462 to engage (e.g., compress) the exposed section 454 of the fluid line 426 carried by the interface cartridge 434 (FIGS. 4D and 4E), thus obstructing fluid flow into the container 404. Conversely, when the cam unit 476 is in the first position (e.g., as shown in FIG. 4H), the elongate arm 478 (obscured in FIG. 4H) can be spaced apart from the cavity 462, thus disengaging from the exposed section 454 of the fluid line 426 and allowing fluid to flow unobstructed or substantially unobstructed into the container 404.

Optionally, the subassembly 424 also includes at least one retainer (e.g., a latch, fastener, etc.) configured to engage a portion of the container 404 (e.g., the cap 432) to secure the container 404 to the subassembly 424. For example, the cam unit 476 can include a protrusion 484 that serves as the retainer. The protrusion 484 can mate with a portion of the container 404 to prevent the container 404 from being removed from the subassembly 424. In the illustrated embodiment, for example, the protrusion 484 has a geometry (e.g., size, shape) that is similar to the geometry of the slot 444 in the cap 432 (FIG. 4E). Accordingly, when the interface cartridge 434 and cap 432 are connected to the bottom section 430 of the subassembly 424 (e.g., as shown in FIG. 4J), the protrusion 484 can fit at least partially into the slot 444 to latch the cap 432 (and thus the container 404) to the subassembly 424.

In some embodiments, the retainer (e.g., protrusion 484) is coordinated with and/or operably coupled to the valve (e.g., elongate arm 478) so that the container 404 cannot be removed from the subassembly 424 when fluid is flowing into the container 404. In the illustrated embodiment, because the protrusion 484 and elongate arm 478 are both connected to the cam unit 476, the cam unit 476 controls the position of both the protrusion 484 and the elongate arm 478. The protrusion 484 can be rotationally offset from the elongate arm 478, such that the protrusion 484 is disengaged from the container 404 when the elongate arm 478 is engaging the fluid line 426, and the protrusion 484 engages the container 404 when the elongate arm 478 is disengaged from the fluid line 426. For example, when the cam unit 476 is in the second position (e.g., as shown in FIG. 4G), the protrusion 484 can be spaced apart from the cavity 462 and can be disengaged from the slot 444 of the cap 432. When the cam unit 476 is in the first position (e.g., as shown in FIG. 4H), the protrusion 484 can be within or near the cavity 462 and can fit at least partially within the slot 444, thus locking the cap 432 (and therefore, the container 404) to the subassembly 424. In other embodiments, however, the subassembly 424 can include a retainer that operates independently of the valve (e.g., a retainer that is not located on and/or coupled to the cam unit 476).

Referring again to 4D, the interface cartridge 434 can optionally include a second retainer for locking the interface cartridge 434 to the subassembly 424, such that the container 404 can be removed from the subassembly 424 independently of the interface cartridge 434. In the illustrated embodiment, for example, the second retainer is configured as a latch 486 (e.g., a ramp, protrusion, etc.) extending from the upper surface 450 of the interface cartridge 434. When the interface cartridge 434 is inserted into the aperture 436 of the subassembly 424, the latch 486 can engage a corresponding notch or recess 488 (FIG. 4G) near the aperture 436. The contact between the latch 486 and the notch 488 can prevent the interface cartridge 434 from being removed from the subassembly 424. Accordingly, the interface cartridge 434 can remain secured to the subassembly 424 (e.g., within the cavity 462 of the lower section 430) while the cap 432 can be separated from the interface cartridge 434, such as when the user wishes to remove the container 404 without removing the interface cartridge 434 (e.g., in order to empty and/or replace the container 404 during a treatment procedure). Accordingly, the user can remove the container 404 from the subassembly 424 with little or no disruption to the fluid line 426 connected to the patient, which can decrease the likelihood of infection and/or contamination. Optionally, the interface cartridge 434 can include a movable flap, seal, barrier, etc., that temporarily seals the exposed end of the fluid line 426 (e.g., by covering the channel 447 (FIG. 4J)) to maintain sterility of the fluid line 426 until the container 404 is reconnected.

Referring next to FIG. 4I, in some embodiments, the cam unit 476 is rotatable to a third position in which both the interface cartridge 434 and container 404 can be removed from the subassembly 424. For example, as shown in FIG. 4I, when in the third position, the cam unit 476 can be oriented such that the protrusion 484 and elongate arm 478 (obscured in FIG. 4I) are spaced apart from the cavity 462 and disengaged from the cap 432 and fluid line 426, respectively. The cam unit 476 can be placed in the third position when the user first connects the interface cartridge 434 and container 404 to the subassembly 424 (e.g., during a setup procedure). The cam unit 476 can also be in the third position when the user is removing the interface cartridge 434 and container 404 from the subassembly 424 (e.g., after the treatment procedure has ended).

Referring again to FIGS. 4C and 4D together, to remove the interface cartridge 434 from the subassembly 424, the user can depress a trigger 490 on the interface cartridge 434. The trigger 490 can be an elongated lever that remains positioned outside of the aperture 436 when the interface cartridge 434 is coupled to the subassembly 424. The trigger 490 can be adjacent to or otherwise connected to the latch 486, such that when the user pushes down on the trigger 490, the latch 486 disengages from the notch 488 of the subassembly 424 (FIG. 4F), thus allowing the interface cartridge 434 to slide out of the aperture 436.

The mechanisms for securing the container 404 and/or interface cartridge 434 can be configured in many different ways. In other embodiments, for example, the container 404 can be locked to the interface cartridge 434, in addition or as an alternative to being locked to the subassembly 424. This approach can be used in situations where the interface cartridge 434 is only removed once per treatment procedure (e.g., after the procedure is completed). Locking the container 404 to the interface cartridge 434 can reduce the likelihood of the container 404 becoming inadvertently dislodged when it is not actively receiving urine (and thus, not locked to the subassembly 424 by the cam unit 476). This may be advantageous, for example, if the console 406 is moved during therapy, e.g., to allow the patient to ambulate. In such embodiments, the retainer for locking and unlocking the interface cartridge 434 can be controlled by the subassembly 424 (or other component of the console 406), rather than by the trigger 490. The trigger 490 can instead be used to unlatch the container 404 from the interface cartridge 434, when the container 404 is not receiving fluid (e.g., the cam unit 476 is not locking the container 404 to the subassembly 424). Alternatively, the subassembly 424 can include a separate electromechanical latch or other retainer for locking and unlocking the container 404 to the cartridge 434, which may be operated by pressing a release button on the console 406, inputting a command via the touchscreen 414, or any other suitable technique.

Optionally, the subassembly 424 can include or be operably coupled to at least one notification device configured to output status notifications. The notifications can inform the user of any of the following statuses: the container 404 is present, the container 404 is not present, the container 404 is empty, the container 404 is partially full, the container 404 is completely full, the amount of fluid in the container 404 greater than or equal to a threshold value, the amount of fluid in the container 404 is less than or equal to a threshold value, the container 404 is currently locked, the container 404 is currently unlocked, the interface cartridge 434 is currently locked, the interface cartridge 434 is currently unlocked, there is a system error, and so on.

Referring again to FIG. 4F, the notification device(s) can include a set of indicator lights 492 (e.g., LED lights). Although FIG. 4F depicts two indicator lights 492 located on the upper section 428 of the subassembly 424, in other embodiments, some or all of the indicator lights 492 can be located on a different portion of the subassembly 424 (e.g., the lower section 430), a different portion of the flow control assembly 402, and/or a different portion of the system 400. Each indicator light 492 can be turned on, turned off, flash, change color, etc., to indicate the status of the subassembly 424 and/or container 404. Alternatively or in combination, the notification device(s) can be configured to output other types of notifications, such as sounds or messages. Notification messages can be displayed on the touchscreen 414 of FIG. 4A or another output device, and/or can be transmitted to a separate device (e.g., a user's mobile device, pager, computer, etc.).

The subassembly 424 can include or be operably coupled to a controller (e.g., a microprocessor—not shown) configured to control the various functional components described herein (e.g., location sensors 466, 468, weight sensor 470, cam unit 476, actuator 482, and/or indicator lights 492). For example, the controller can receive and process sensor data from the location sensors 466, 468 to detect whether the interface cartridge 434 and container 404, respectively, are coupled to the subassembly 424. The controller can also receive and process sensor data from the weight sensor 470 to measure the amount of fluid within the container 404. Optionally, the actuator 482 and/or cam unit 476 can include a positional sensor (e.g., a potentiometer), and the controller can use data from the positional sensor to determine the current state of the actuator 482 and/or cam unit 476 (e.g., whether the cam unit 476 is in the first, second, or third position).

Based on the received sensor data, the controller can adjust the position the cam unit 476 to control fluid flow to the container 404. For example, if the controller determines that the container 404 is too full (e.g., the amount of fluid within the container 404 is above a threshold level), the controller can actuate the cam unit 476 to the second position so the elongate arm 478 cuts off fluid flow into the container 404. Conversely, if the controller determines that the container 404 still has available space (e.g., the amount of fluid within the container 404 is below a threshold level), the controller can maintain the cam unit 476 in the first position so fluid can continue to flow into the container 404. The controller can also adjust the status of the indicator lights 492 to reflect the current status of the subassembly 424.

Referring again to FIG. 4B, in some embodiments, each subassembly 424*a-b* includes a respective individual controller. In such embodiments, each controller can be at any suitable location within the corresponding subassembly 424*a-b* (e.g., in the upper section 428 or the lower section 430). In other embodiments, however, both subassemblies 424*a-b* are operably coupled to a single controller. In such embodiments, the controller can be at any suitable location in the flow control assembly 402 (e.g., mounted on or otherwise coupled to the frame 420). Alternatively, the controller can be spaced apart from the flow control assembly 402, such as within the console 406 of the system 400 of FIG. 4A. Optionally, the controller can be the same as the controller 412 of the system 400 of FIG. 4A.

Figure 5:
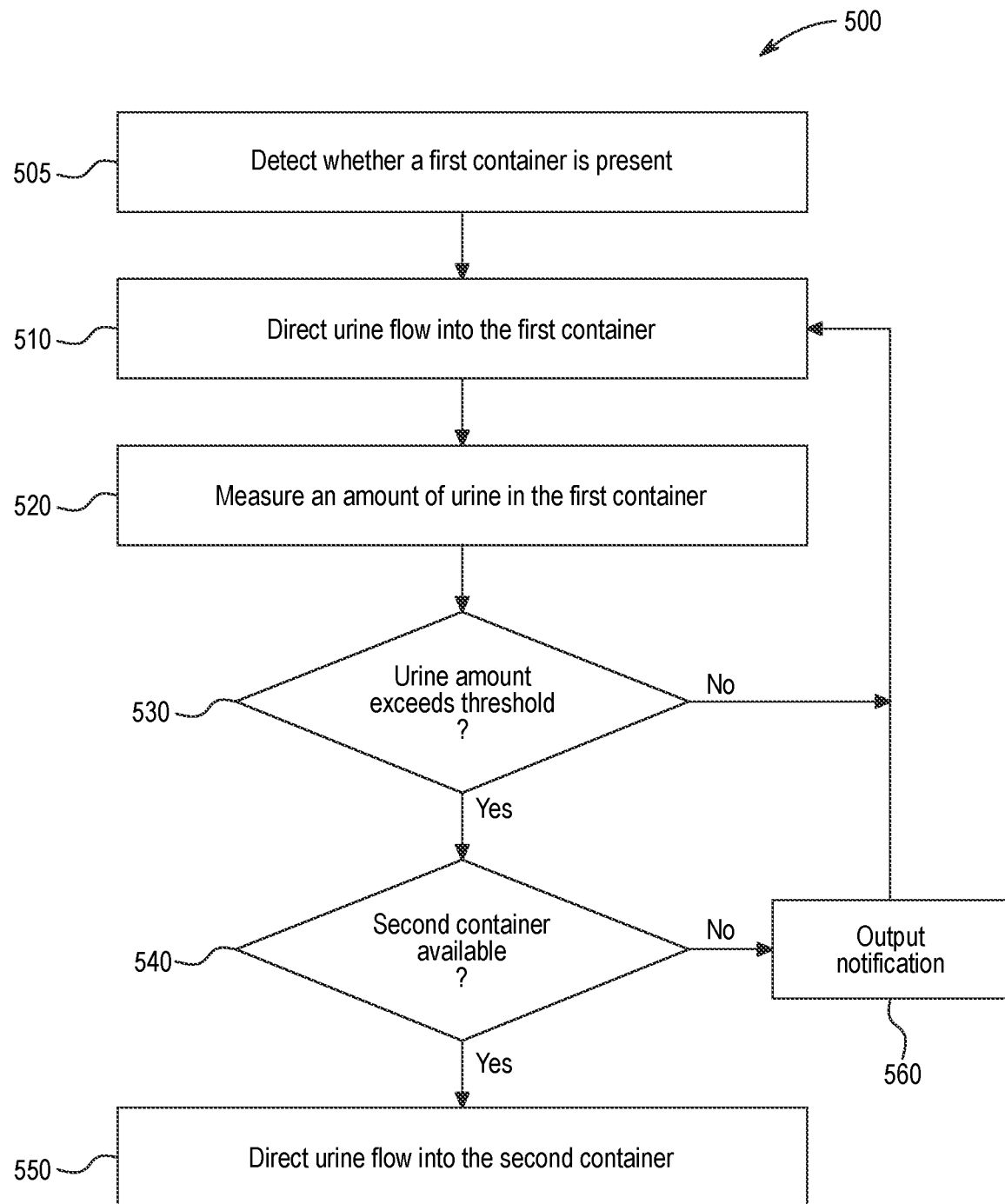
FIG. 5 is a flow diagram illustrating a method for collecting urine from a patient, in accordance with embodiments of the present technology.

FIG. 5 is a flow diagram illustrating a method 500 for collecting urine from a patient, in accordance with embodiments of the present technology. The method 500 can be performed by any embodiment of the systems and devices described herein, such as the system 300 of FIG. 3 or the system 400 of FIGS. 4A-4J. In some embodiments, some or all of the stages of the method 500 are performed by a system or device including one or more processors and a memory storing instructions that, when executed by the one or more processors, cause the system or device to perform one or more of the stages described herein. For example, the method 500 can be performed by a flow control assembly (e.g., flow control assembly 302 of FIG. 3 or flow control assembly 402 of FIGS. 4A-4J) that includes or is operably coupled to a controller (e.g., controller 312 of FIG. 3 or controller 412 of FIGS. 4A-4J). Optionally, some or all of the stages of the method 500 can performed automatically or semi-automatically by a suitable system or device, with little or no human intervention.

The method 500 begins at stage 505 with detecting whether a first container is present. The first container can be any container suitable for holding urine from a patient (e.g., the first container 404*a* of the system 400 of FIGS. 4A-4J). In some embodiments, stage 505 includes determining whether the first container is present and/or properly connected to the system based on sensor data. The sensor data can be generated by at least one sensor suitable for detecting the presence (e.g., location, proximity) of the first container, such as location sensors (e.g., sensors 466 and/or 468 of the system 400), optical sensors, RFID sensors, and so on. The sensor(s) can be part of and/or operably coupled to a flow control assembly associated with the first container, such as the flow control assembly 402 of the system 400. In some embodiments, the sensor(s) are part of and/or operably coupled to an individual subassembly associated with the first container, such as the first subassembly 424 of the system 400.

Optionally, stage 505 can also include detecting whether at least one second container (e.g., the second container 404*b* of the system 400 of FIGS. 4A-4J) is present. The techniques for detecting the additional container(s) can be identical or generally similar to the techniques for detecting the first container. Additionally, stage 505 can include additional processes for preparing the system for operation, such as priming one or more fluid lines connected to the containers. Examples of devices and techniques for priming fluid lines are described in greater detail below in connection with FIGS. 7 and 8.

At stage 510, the method 500 continues with directing urine flow into the first container. Stage 510 can include actuating a first valve operably coupled to the first container so urine and/or other fluid can flow into the first container. For example, the first container and first valve can be connected to a first fluid line for receiving urine from the patient, and the first valve can be actuated to an open configuration to allow fluid to flow through the first fluid line. In some embodiments, stage 510 also includes locking the first container with a first retainer so the first container cannot be removed from the flow control assembly. This can advantageously prevent spills or leaks caused by inadvertently removing the first container during operation. The first valve and first retainer can be or include any of the embodiments described above with reference to FIGS. 3-4J.

Optionally, stage 510 can include restricting urine flow into the second container, such as by actuating a second valve operably coupled to the second container to prevent fluid from entering the second container. For example, the second container and second valve can be connected to a second fluid line for receiving urine from the patient, and the second valve can be actuated to a closed configuration to prevent fluid from flowing through the second fluid line. In such embodiments, stage 510 can further includes unlocking the second container with a second retainer so the second container can be removed from the flow control assembly. The second valve and second retainer can be or include any of the embodiments described above with reference to FIGS. 3-4J.

At stage 520, the method 500 includes measuring an amount of urine in the first container. The urine amount can be quantified based on weight, volume, fluid level, and/or any other suitable parameter. Alternatively or in combination, stage 520 can include measuring a urine flow rate into the first container. The urine amount and/or flow rate can be determined based on sensor data from any suitable sensor, such as any of the sensors described herein with reference to FIGS. 3-4J. In some embodiments, the urine amount and/or flow rate is measured once every second, 5 seconds, 10 second, 30 seconds, 1 minute, 2 minutes, 5 minutes, 10 minutes, or any other suitable time interval.

At stage 530, the method 500 continues with determining whether the amount of urine in the first container exceeds a threshold based on the measurements from stage 520. The threshold can be a value or range indicating that the first container is partially or completely full. The threshold can correspond to a parameter (e.g., volume, weight, fluid level, etc.) of the first container when the first container is at least 50%, 60%, 70%, 75%, 80%, 85%, 90%, 95%, 99%, or 100% full. For example, the threshold can be a weight value corresponding to 50%, 60%, 70%, 75%, 80%, 85%, 90%, 95%, 99%, or 100% of the maximum weight of the first container (e.g., the weight of the first container when completely full). As another example, the threshold can be a volume value corresponding to 50%, 60%, 70%, 75%, 80%, 85%, 90%, 95%, 99%, or 100% of the maximum volume of fluid that the first container can hold. Optionally, the threshold can vary based on the urine flow rate, e.g., the threshold is lower if the urine flow rate is high, and is higher if the urine flow rate is low.

If the amount of urine is less than or equal to the threshold, the method 500 can return to stage 510 to continue the flow of urine into the first container. If the urine amount exceeds the threshold, the method 500 can proceed to stage 540 to determine whether the second container is available. For example, stage 540 can include detecting whether the second container is present, using any of the techniques previously described in connection with stage 505. Additionally, stage 540 can include measuring an amount of urine in the second container to determine whether the second container has space to hold urine, based on sensor data from at least one sensor as described above with respect to stage 520. For example, the second container can be considered to be "available" if the amount of urine in the second container is less than or equal to a threshold (e.g., a threshold corresponding to the volume, weight, and/or fluid level of the second container when the second container is at least 50%, 60%, 70%, 75%, 80%, 85%, 90%, 95%, 99%, or 100% full). In such embodiments, the threshold for the second container can be the same as the threshold for the first container, or can be a different threshold (e.g., a higher or lower threshold value). As another example, the second container can be considered to be available if the amount of urine in the second container is less than the amount of urine in the first container. In yet another example, the second container can be considered to be available if the second container is less full than the first container.

If the second container is available in stage 540, the method 500 can proceed to stage 550 with directing urine flow into the second container. Stage 550 can include actuating the second valve to open the second fluid line and allow fluid to enter the second container. Optionally, stage 550 can also include locking the second container with the second retainer so the second container cannot be removed from the flow control assembly. The method 500 can then return to stage 510 as described above, except that the method 500 now involves monitoring the amount of urine in the second container, rather than in the first container.

In some embodiments, stage 550 also includes directing urine flow away from the first container, such as by actuating the first valve to close the first fluid line and prevent fluid from entering the first container. The first container can be unlocked from the flow assembly by actuating the first retainer, thus allowing a user to remove, empty, and/or replace the first container. Stage 550 can include concurrently or subsequently alerting the user (e.g., via a light, a sound, a message, and/or other notification) that the first container should be emptied and/or replaced.

If the second container is unavailable (e.g., not present or too full) in stage 540, the method 500 can instead proceed to stage 560 to output a notification alerting the user than the first container is full or nearly full, and that the user should either insert a second container into the system (if the second container is not present) or empty the second container (if the second container is present but too full). The notification can include any of the embodiments described herein, such as a light, a sound, a message displayed on a user interface, a message transmitted to a user device, or suitable combinations thereof. The method 500 can then return to stage 510 with continue with directing urine flow into the first container until the second container becomes available.

In some embodiments, some or all of the stages of the method 500 are performed as part of a medical procedure for a patient. The medical procedure can be or include any diagnostic or therapeutic regimen involving monitoring the patient's urine output. For example, the medical procedure can include treating the patient for a fluid overload condition (e.g., as previously described with respect to FIGS. 1A and 2). The method 500 can be performed multiple times during the medical procedure to provide continuous or substantially continuous urine output monitoring and/or collection. Accordingly, the method 500 can advantageously reduce the number of times the healthcare professional needs to check on the status of the containers and/or empty the containers during the medical procedure.

In some embodiments, the medical procedure is performed by a semi-automated or fully automated fluid management system (e.g., the system 100 of FIG. 1A) and the method 500 is performed by a flow control assembly (e.g., the flow control assembly 302 of FIG. 3 or flow control assembly 402 of FIGS. 4A-4J) that is included in or otherwise operably coupled to the system. In such embodiments, the operations of the system and the flow control assembly can be coordinated. For example, once the flow control assembly detects that one or both containers are present and ready for use (e.g., as described in stage 505), the flow control assembly can transmit a signal to the system to indicate that the medical procedure can begin (e.g., infusing a diuretic and/or hydration fluid into the patient to elicit urine output). As another example, the system can send a signal to the flow control assembly once the medical procedure has ended (e.g., the patient has exhibited the desired amount of net fluid loss, a predetermined time period has elapsed, and/or the patient has been disconnected from the urine collection system), and the flow control assembly can automatically shut off fluid flow to both containers, and, optionally, unlock both containers for removal.

Although the method 500 is described herein with in connection with two containers, in other embodiments, the method 500 can be modified to accommodate a different number of containers (e.g., three, four, five, or more containers). In such embodiments, the method 500 can include directing urine flow into a single container at a time, and switching to the next container when the previous container is full. Alternatively, the method 500 can include directing urine flow into multiple containers concurrently, and then shutting off flow to each container individually when the container becomes full.

Figure 6A:
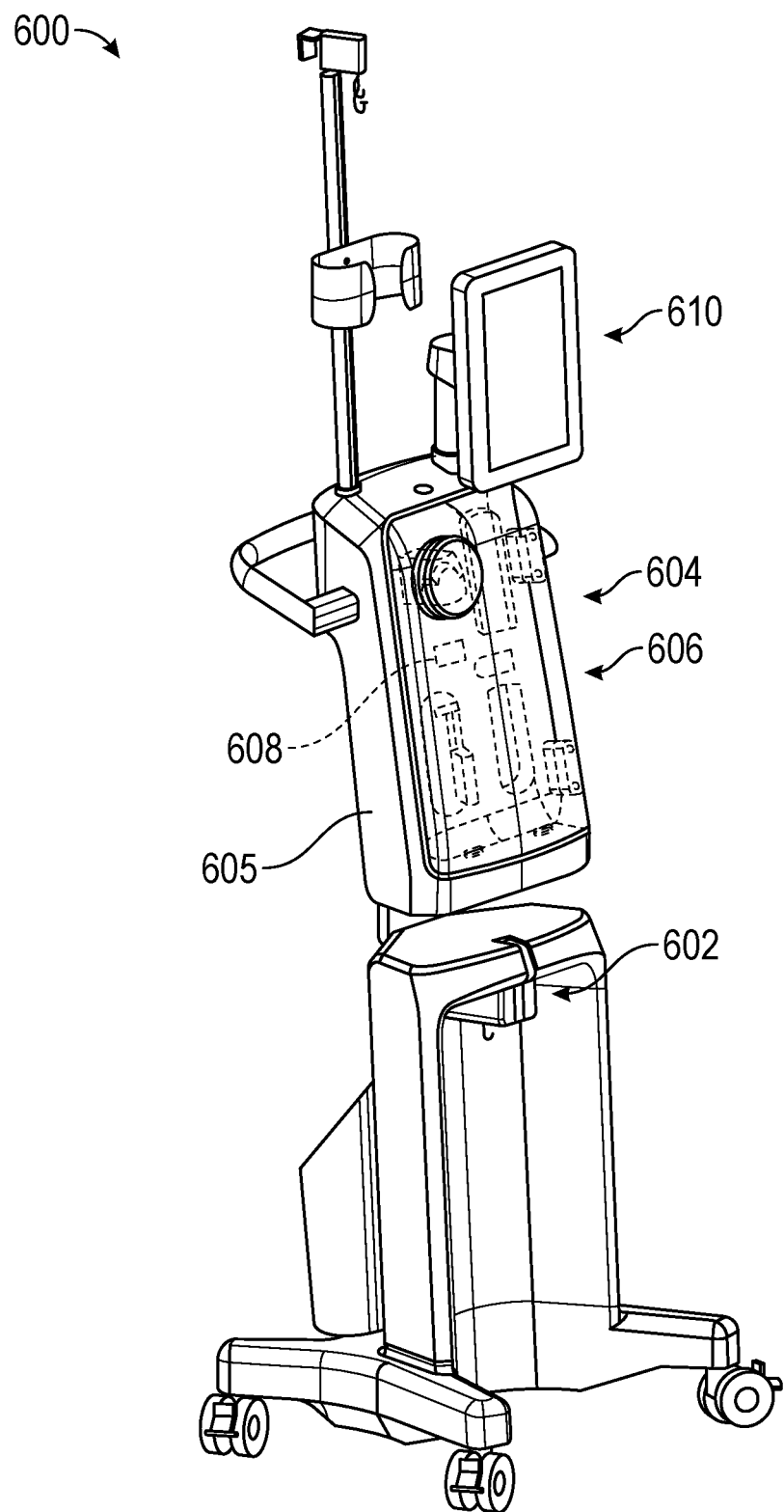
FIGS. 6A-6H illustrate a representative example of a urine collection system, in accordance with embodiments of the present technology.

FIGS. 6A-6F illustrate a representative example of another urine collection system 600 ("system 600") configured in accordance with embodiments of the present technology. More specifically, FIG. 6A is a perspective view of the system 600, and FIGS. 6B-6F are various views of a urine system 602 of the system 600. The system 600 can include at least some aspects that are generally similar or identical in structure and/or function to one or more of the embodiments described herein (e.g., the systems 100, 160, 170, 180 of FIGS. 1A-1D, the system 300 of FIG. 3, and/or the system 400 of FIG. 4A-4J), such as one or more of the components for monitoring and/or managing fluid levels previously described with reference to FIG. 1A. Additionally or alternatively, any of the features of the embodiments of FIGS. 6A-6F can be combined with each other and/or with any of other systems and devices described herein (e.g., the system 100 of FIG. 1A and/or the system 300 of FIG. 3).

Referring to FIG. 6A, the system 600 includes a urine collection and monitoring system 602 ("urine system 602"), an automated hydration fluid infusion system 604 ("hydration system 604"), an automated diuretic infusion system 606 ("diuretic system 606"), a controller or control system 608 ("controller 608"), and a display or input/output unit 610 ("display 610"). The controller 608 can be operably coupled to each of the urine system 602, hydration system 604, diuretic system 606, and/or display 610. The system 600 can further include a console or structure 605 ("console 605") that incorporates, houses, and/or otherwise supports all or portions of the urine system 602, hydration system 604, diuretic system 606, the controller 608, and/or the display 610. Similar to the embodiments described above, the urine system 602 collects and monitors urine from a patient while the automated hydration fluid infusion system 604 automatically delivers fluid to the patient and/or the automated diuretic infusion system 606 automatically delivers a diuretic to the patient based on, in part, data obtained from the urine system 602. For example, as described herein, the amount of diuretic and/or hydration fluid provided to the patient is based on urine output from the patient, as measured via the urine system 602.

Figure 6B:
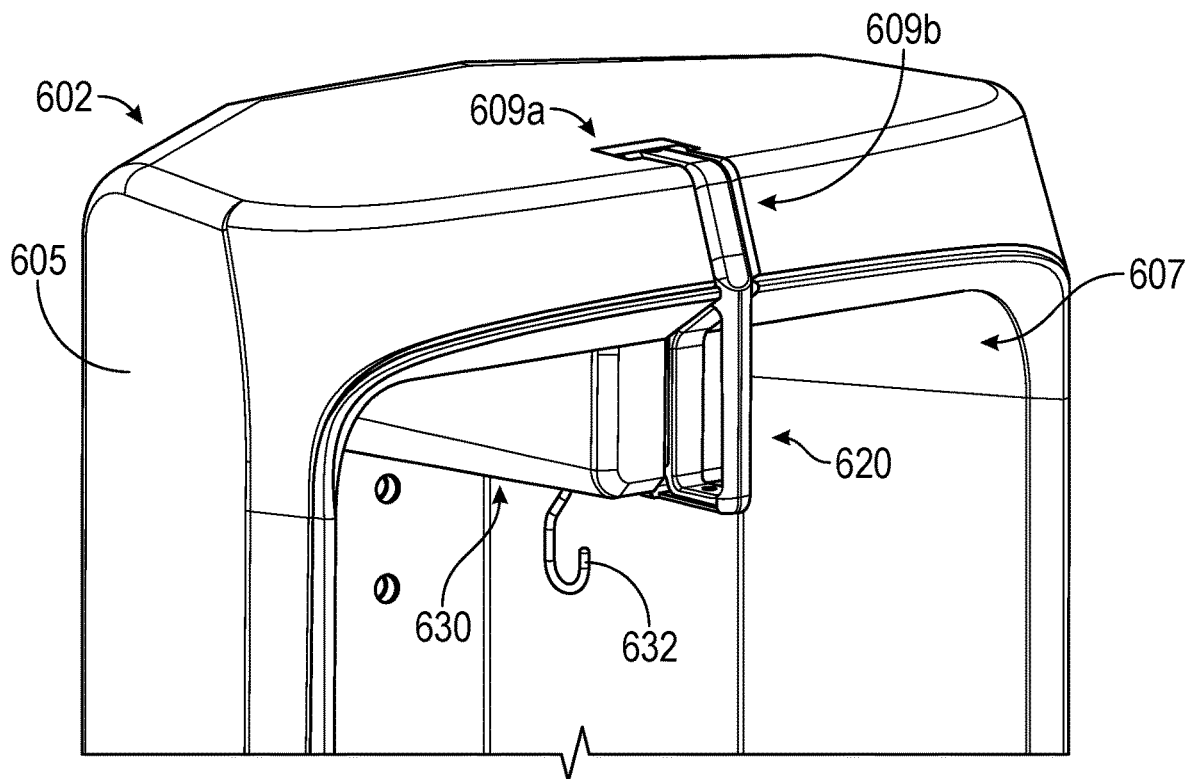
Figure 6C:
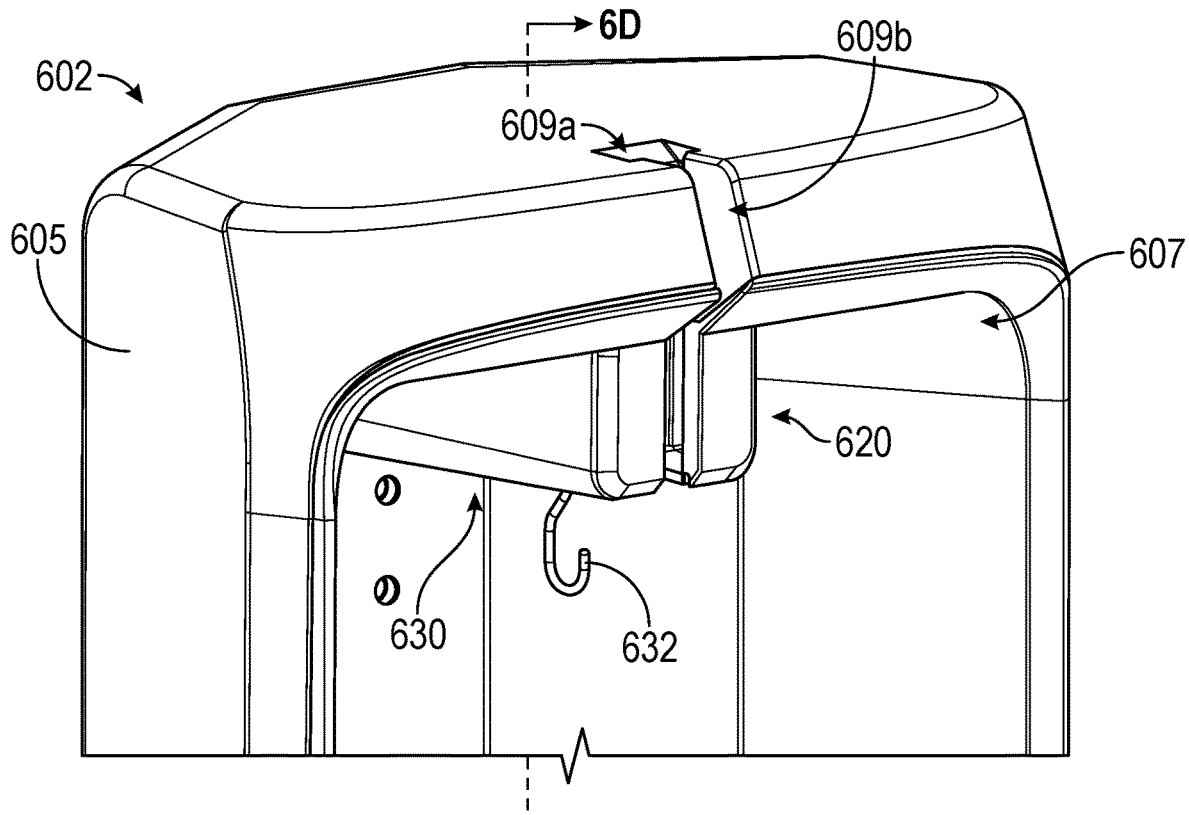

FIGS. 6B and 6C are perspective views of the urine system 602. The urine system 602 can include a urine cartridge 620 (FIG. 6B) and a urine flow assembly 630. The urine cartridge 620 and the urine flow assembly can together be referred to as a flow control assembly. The urine flow assembly 630 can include a container mounting component 632 ("mounting component 632"). In the illustrated embodiment, the mounting component 632 includes a coupler (e.g., a hook) from which a container (e.g., the container 112; FIGS. 1B-1D) can hang or be supported. The mounting component 632 is movable between a first unstressed position and a second stressed position when the mounting component 632 is supporting a weight of the container. As such, when in the second position or not in the first position, the mounting component 632 can indicate the presence of the container thereon. When in the second position, the mounting component 632 can engage components of the urine flow assembly 630, e.g., by activating one or more sensors to monitor and/or determine a urine output rate of the patient. As shown in FIGS. 6B and 6C, the urine cartridge 620 and/or the urine flow assembly 630 can be positioned at least partially within a chamber or recessed area 607 defined in part by the console 605. For example, the mounting component 632 and container (not shown) hanging therefrom can be in the recessed area 607, which can be behind a door so as to limit the likelihood of physically disturbing the container and/or mounting component 632.

The urine cartridge 620 can be detachably coupled to the system 602. For example, the urine system 602 can include one or more receiving features 609 (identified by reference numbers 609a and 609b) configured to receive the urine cartridge 620. In the illustrated embodiment, the urine system 602 includes a pivotal receiving feature 609a and a slot receiving feature 609b, which together can couple the urine cartridge 620 to the urine system 602. As shown in FIG. 6B, which omits the urine cartridge 620 for illustrative purposes, the pivotal receiving feature 609a can pivotally engage the urine cartridge 620 such that the urine cartridge 620 can pivot toward and/or at least partially into the slot receive feature 609b. As described elsewhere herein (e.g., with reference to FIGS. 6D-6F), the urine cartridge 620 can include tubing configured to direct urine from the patient to the container, and when coupled to the system 602, the urine cartridge 620 can position and orient the tubing relative to aspects of the urine flow assembly 630 to enable urine flow measurement and to provide a urine output (e.g., an average urine output rate). In some embodiments, the tubing is coupled (e.g., adhered) to the urine cartridge 620 prior to attached the urine cartridge 620 to the console 605 at the receiving feature 609.

Figure 6D:
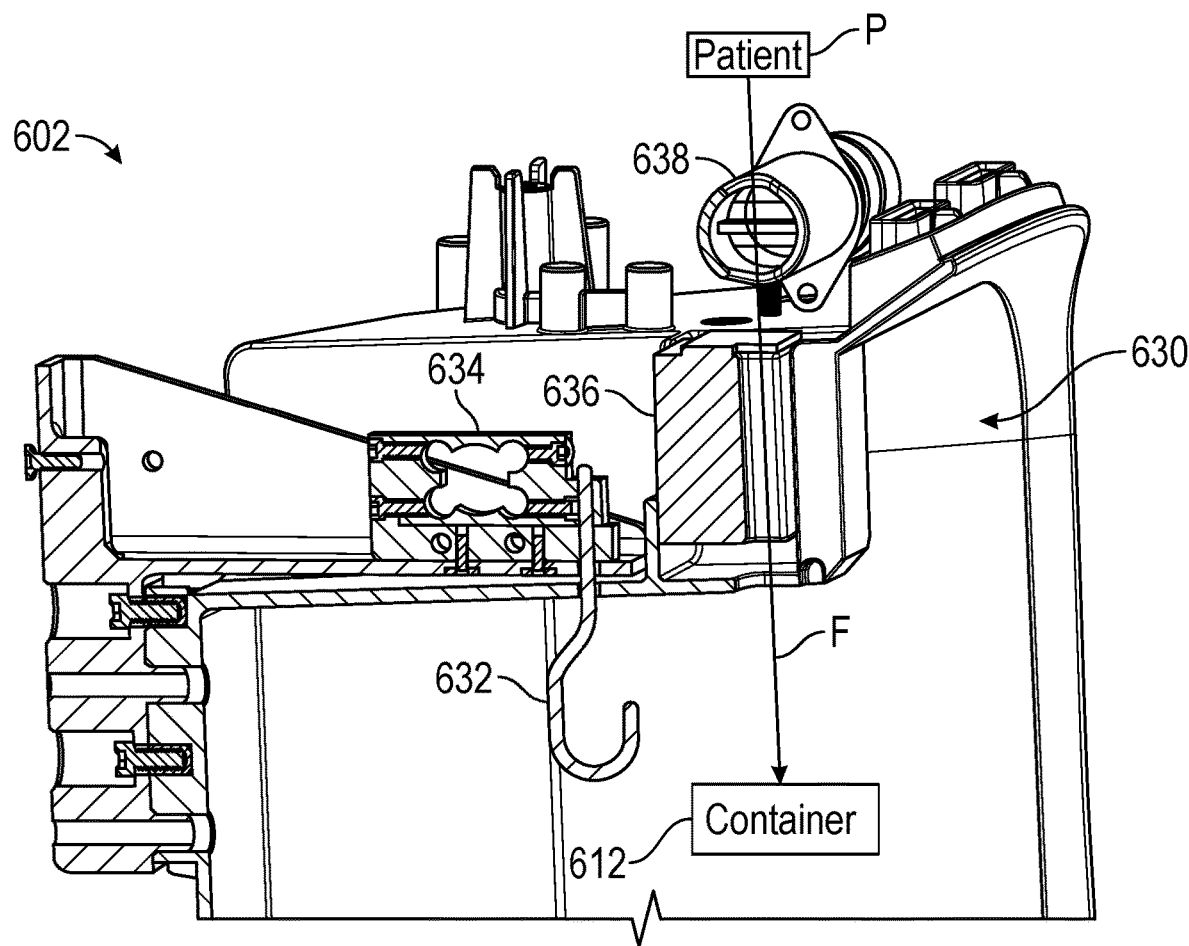

FIG. 6D is a partially-schematic, cross-sectional perspective view of the urine system 602 taken along line 6D-6D in FIG. 6C. As shown in FIG. 6D, fluid F (e.g., urine) from the patient P can flow through a portion of the urine system 602 and into a container 612 (e.g., the container 112; FIGS. 1B-1D) via one or more fluid lines (e.g., the fluid line 119; FIGS. 1B-1D). The urine flow assembly 630 can include one or more fluid sensors operable to measure and/or determine the flow of the fluid F through the urine system 602. As shown in FIG. 6D, the urine flow assembly 630 includes a first fluid sensor 634 (e.g., the second sensor 114b; FIG. 1B) and a second fluid sensor 636 (e.g., the first sensor 114a; FIG. 1B). The first sensor 634 can include a load cell and be configured to measure or generate (e.g., on a continuous basis) first sensor data including a weight of the container 612 when coupled to the mounting component 632. The first sensor data (e.g., the weight and/or the change in weight of the container 612) can be used to generate a first patient urine output (e.g., an average volumetric flow rate). The second sensor 636 can include a flow sensor and be configured to measure or generate (e.g., on a continuous basis) second sensor data including a flow of the fluid F through the fluid line. The second sensor data can be used to generate a second patient urine output (e.g., an average volumetric flow rate).

The urine system 602 can further include one or more flow control devices 638 (e.g., the flow control device 138 of FIG. 1B). The flow control device 638 can include a pinch clamp or valve configured to fully or at least partially regulate fluid flow through the system 602, such as when priming one or more of the fluid lines. The flow control device 638 can also be used to regulate flow if the system 602 determines that the weight of the container 612 is decreasing, e.g., based on the first sensor data from the first sensor 634, or through user input. In such embodiments, the flow control device 638 may only regulate flow if the second sensor 636 is disabled or non-operational and only the first sensor 634 is operational. During the time the flow control device 638 is closed and there is no flow to the container 612, patient urine output is not measured. However, in such embodiments, the rate and/or volume of urine output can be calculated or estimated based on at least the time of no flow and the resulting flow measurement once flow resumes. The flow control device 638 can regulate the fluid flow without touching the fluid by externally pinching the fluid line. Alternately, the flow control device 638 can be a gate, needle or other type of valve that can regulate fluid flow by being in contact with the fluid. The priming of fluid lines is discussed in detail herein, e.g., with reference to FIGS. 9A-14B. In the illustrated embodiment, the flow control device 638 is positioned upstream from the flow sensor 636. In other embodiments, the flow control device 638 can be positioned downstream from the flow sensor 636, and/or have any other suitable positions.

Figure 6F:
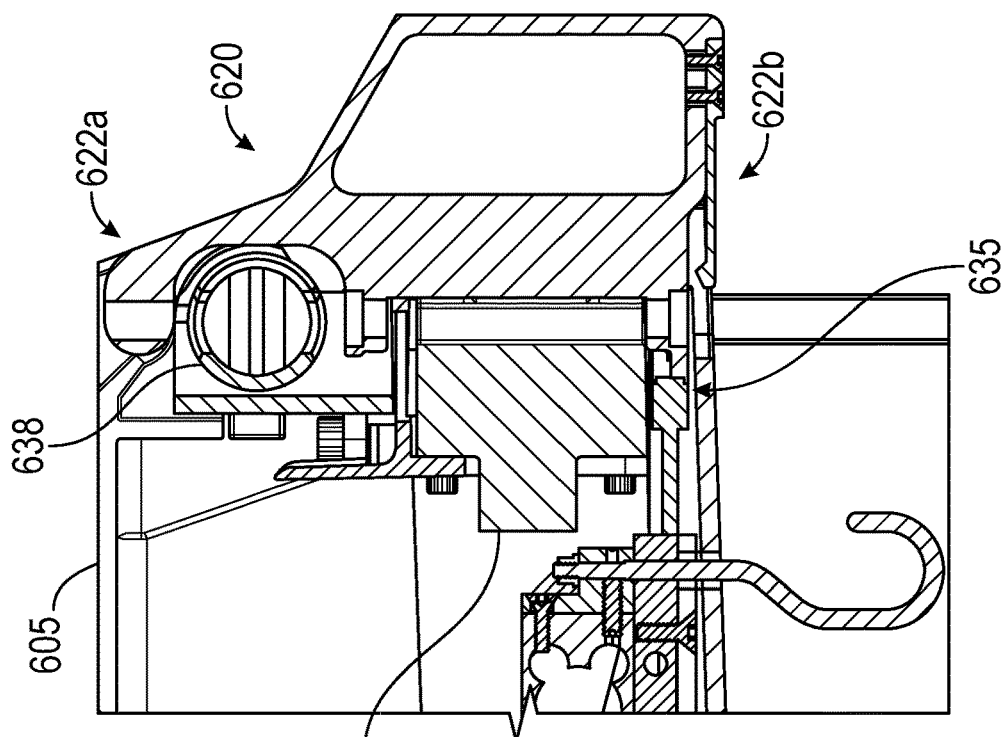
Figure 6E:
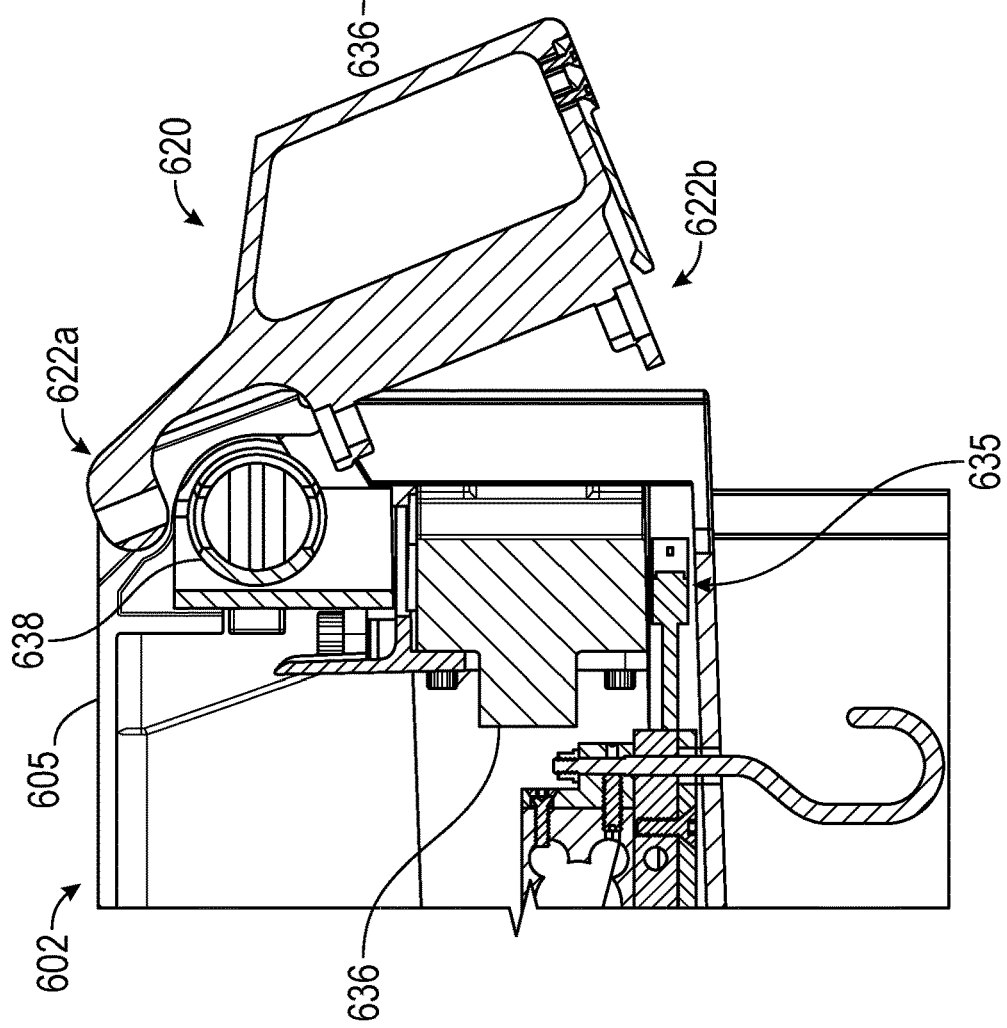

FIGS. 6E and 6F are partially-schematic, cross-sectional side views of the urine system 602, with FIG. 6E illustrating an upper portion 622a of the urine cartridge 620 engaging the console 605 and FIG. 6F illustrating the upper portion 622a and a lower portion 622b of the urine cartridge 620 engaging the console 605. As described in more detail with reference to FIG. 6H, the lower portion 622b can be fixedly attached to the console 605, e.g., by snapping into a corresponding feature of the console 605. The fluid line (e.g., the fluid line 619 of FIGS. 6G and 6H) is omitted from FIGS. 6E and 6F for illustrative purposes, but as described herein can extend through portions of the urine cartridge 620 and the flow control device 638, such that the fluid line 619 is positioned adjacent the second sensor 636.

As shown in FIGS. 6E and 6F, the system 602 can further include one or more detection sensors 635. In some embodiments, the one or more sensors 635 are optical interrupter sensors including an emitter emitting an infrared beam and a receiver positioned to receive the beam. When the urine cartridge 620 is correctly coupled to the console 605, the beam is interrupted and not received by the receiver. In response, the system 602 or controller can generate a signal indicating the urine cartridge 620 is present and/or correctly positioned, thus indicating that the fluid line is properly positioned relative to the second sensor 636. As shown in FIGS. 6D and 6E, the one or more sensors 635 is positioned adjacent (e.g., below) the second sensor 636, however in other embodiments the one or more sensors 635 can be positioned elsewhere on the console 605 or system 602. In some embodiments, the one or more sensors 635 can be a mechanical switch moveable between a first position, and a second position indicating the presence and/or correct positioning of the urine cartridge 620.

Figure 6G:
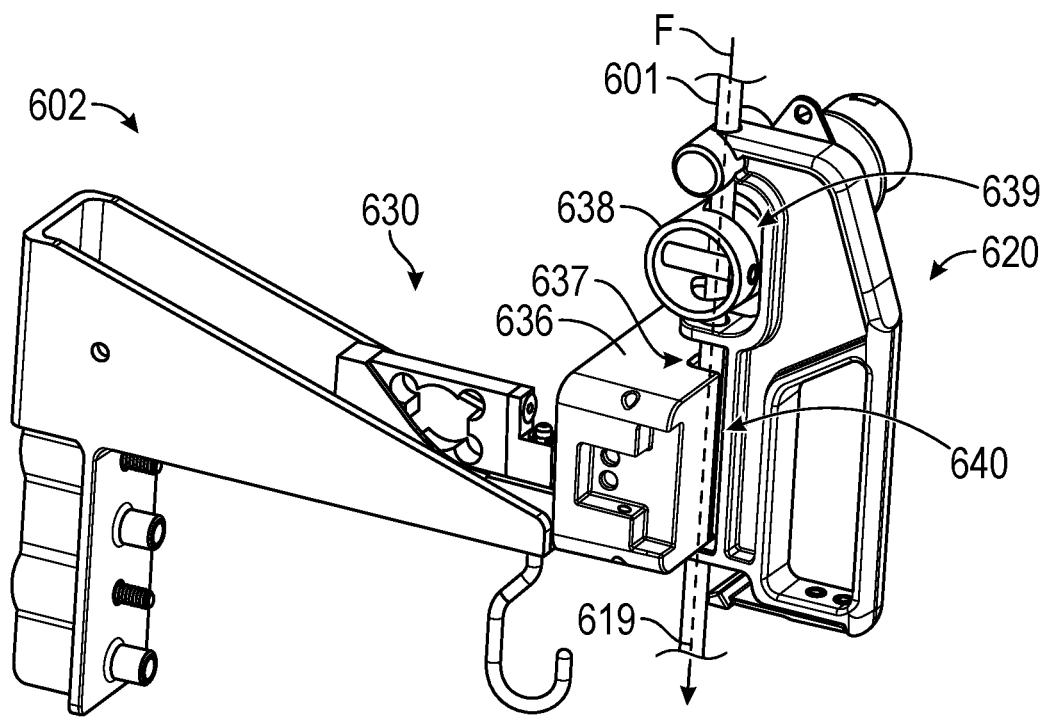

FIG. 6G is a perspective view of the urine cartridge 620 and the urine flow assembly 630. The urine cartridge 620 can be configured to receive a fluid line 619 (e.g., the fluid line 119; FIGS. 1B-1D). The fluid line 619 can fluidly couple the patient P (FIG. 6D) via a catheter (e.g., the catheter 118; FIG. 1B) with the container 612 (FIG. 6D). As shown in FIG. 6G, the flow sensor 636 can include a groove 637 (e.g., a U-shaped groove) that at least partially defines a slot or channel 640 ("slot 640") that receives the fluid line 619. The slot 640 is further defined on an opposing side by a portion of the urine cartridge 620. When the urine cartridge 620 is coupled to the system 602 and/or console 605 (FIGS. 6B and 6C), the urine cartridge 620 and flow sensor 636 can position and/or orient the fluid line 619 within the slot 640 to ensure an accurate and reliable flow measurement. In the illustrated embodiment, for example, the urine cartridge 620 can be configured to press and/or hold the fluid line 601 against the flow sensor 636, which can improve the accuracy of the urine output measured via the flow sensor 636.

As shown in FIG. 6G, the flow control device 638 can include a slot or groove 639 configured to receive the fluid line 619. The slot 639 can enable the fluid line 619 to be coupled to the urine cartridge 620 prior to the urine cartridge 620 being coupled to the console 605 (FIG. 6E) or rest of the system 602. The fluid line 619 can be coupled (e.g., adhered) to portions of the urine cartridge 620, which as previously noted can be removably attached to the console 605 (FIGS. 6B and 6C). In doing so, the position and orientation of the fluid line 619 within the slot 640 can be set (e.g., without a user or healthcare professional) prior to coupling the urine cartridge 620 to the console 605, e.g., to ensure a more accurate flow measurement via the flow sensor 636. Additionally or alternatively, in doing so the length of the fluid line 619 extending from the urine cartridge to the container 612 (FIG. 6D) can be set to the proper length, which can also ensure a more accurate flow measurement via the flow sensor 636. Stated differently, if the fluid line 619 is not properly set within the slot 640, or if length of fluid line 619 extending from the urine cartridge 620 to the container 612 is improper (e.g., too short), then the flow measurement via the flow sensor 636 can be less accurate and/or less consistent between measurements. For example, if the fluid line 619 extending from the urine cartridge 620 to the container 612 is too short, the container 612 may add additional stress on and/or physically dislodge the urine cartridge which can affect the flow measurement via the flow sensor 636. In addition, if the fluid line 619 extending from the urine cartridge 620 to the container 612 is too short, the container 612 may be pulled by the tubing 619 which can alter the container 612 weight reading of the first sensor 634 leading to inaccurate measurement of fluid flow rate or volume into the container 612.

The operation of the urine system 602 can be generally similar to the operation of other systems described herein, such as the fluid management system 160 of FIG. 1B. As the fluid F flows through the urine system 602 and into the container 612, the weight of the container 612 increases. Accordingly, the weight sensor 634 can measure the accumulation of the fluid F within the container 612 by measuring the weight of the container 612, and generate therefrom a urine output rate from the patient. At some point the fluid F may be drained or otherwise removed from the container 612 (e.g., via the drain valve 113 of FIG. 1B) when the container 612 is full or above a predetermined threshold. When the container 612 is being drained, the weight of the container 612 is expected to decrease or, since the container 612 is still collecting fluid F during draining, increase at a slower rate than expected. Additionally or alternatively, the container 612 may be replaced with another container.

The weight sensor 634 may provide less accurate urine output measurements when the container 612 is being replaced and/or emptied. However, during these times, the flow sensor 636, which can operate independent of the weight and/or presence of the container 612, can continue to measure the patient's urine output, such that the system 600 (FIG. 6A) can continue providing therapy while the container 612 is being replaced and/or emptied. In some embodiments, for example, the urine system 602 can detect a decrease in the weight of the container 612 associated with replacing and/or emptying the container 612 and, in response, switch to using the flow sensor 636 to measure the patient's urine output. The urine system 602 may return to using the weight sensor 634 when the urine system 602 detects an increase in weight associated with fluid collection within the container 612 or replacement of the container 612. Additionally or alternatively, the urine system 602 can use both the weight sensor 634 and the flow sensor 636 to measure the patient's urine output before, during, and/or after the container 612 is emptied and/or replaced, and/or may compare the measurements of both sensors 634, 636 to ensure accuracy, as described in detail above with reference to FIG. 1B. In some embodiments, one of the weight sensor 632 or the flow sensor 636 can be omitted.

Figure 6H:
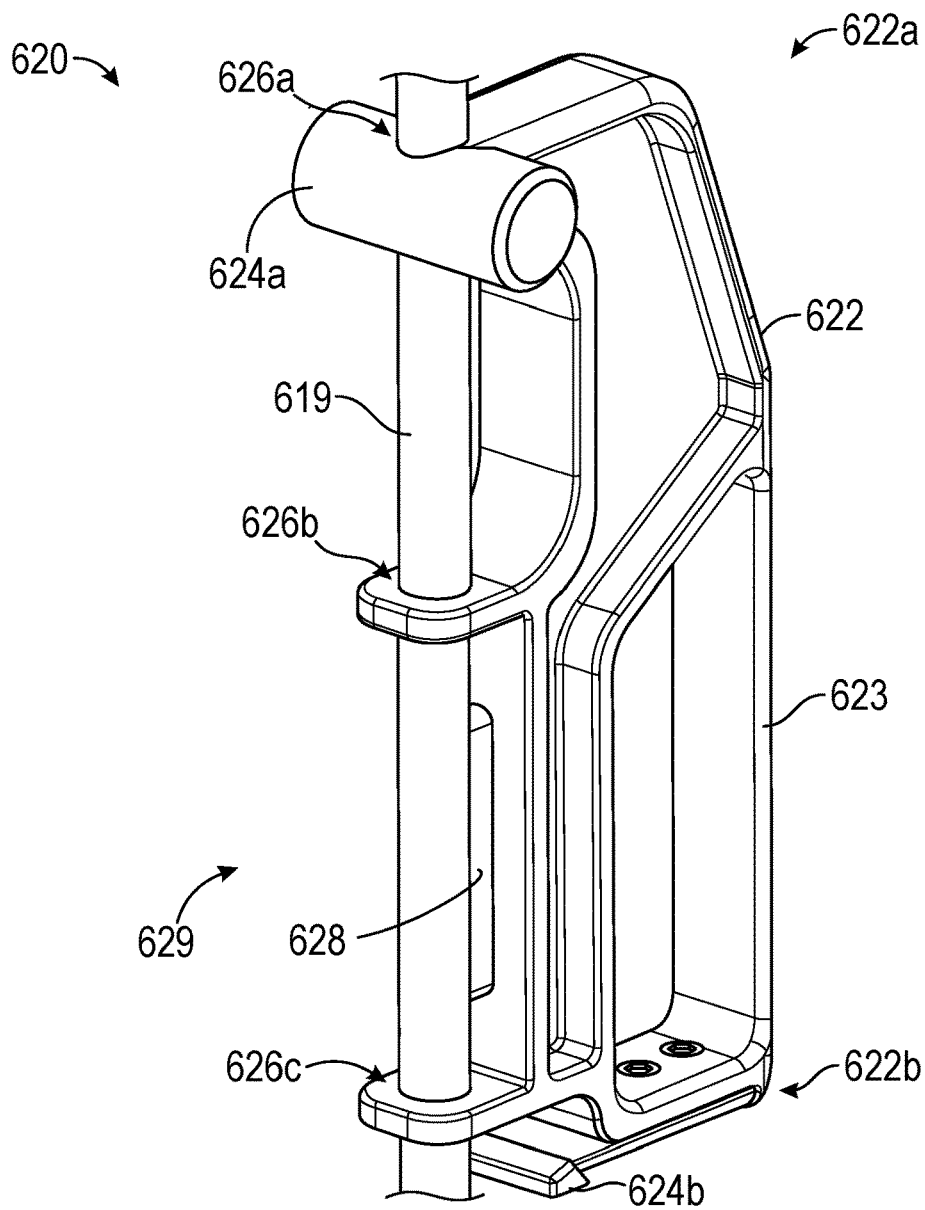
Figure 7:
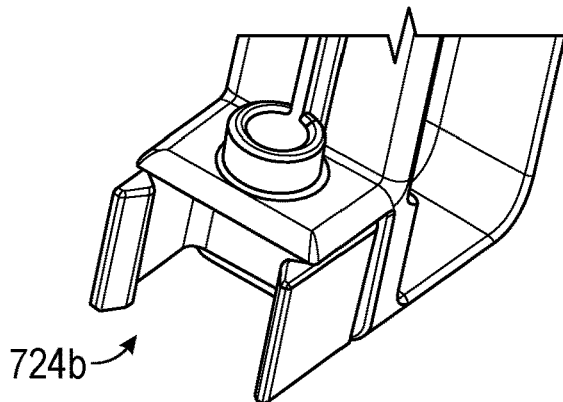
FIG. 7 illustrates an example of a urine cartridge of a urine collection system, in accordance with embodiments of the present technology.

FIG. 6H is a perspective view of the urine cartridge 620. The urine cartridge 620 can include a body 622 having a first or upper end portion 622a and a second or lower end portion 622b opposite the first end portion 622a. The first end portion 622a can include a first urine system coupling feature 624a ("first coupling feature 624a") and the second end portion 622b can include a second urine system coupling feature 624b ("second coupling feature 624b"). The first coupling feature 624a and the second coupling features 624b can ensure a precise placement of the fluid line 619 relative to the flow sensor 636 (FIG. 6G). In the illustrated embodiment, the first coupling feature 624a can be pivotally received by the pivotal receiving feature 609a (FIGS. 6B and 6C) and the second coupling feature 624b can be inserted within a correspondingly-shaped recess (not shown) in the console 605 (FIGS. 6B and 6C). The second coupling feature 624b can include a tab having a flared end or other shape. For example, in some embodiments, such as shown in FIG. 7, the urine cartridge 620 can include a coupling feature 724b having a plurality of vertically-aligned tabs, or any other suitable configuration.

Referring again to FIG. 6H, the urine cartridge 620 can further include one or more ports or apertures 626a-c (collectively referred to as "ports 626") through which the fluid line 619 is inserted. Stated differently, the ports 626 define a pathway for the fluid F to flow from the patient to the container. The urine cartridge 620 can include a sensing region 629 that at least partially defines the slot 640 (FIGS. 6D and 6G), and a fluid line engagement feature 628 ("engagement feature 628") configured to engage or abut the fluid line with the urine flow assembly 630. As previously described (e.g., with reference to FIG. 6G), the urine cartridge 620 in part can position and/or orient the fluid line 619 within the slot 640 to ensure an accurate and consistent flow measurement. In the illustrated embodiment, the engagement feature 628 includes a protrusion or tab extending from the body 622, and limits bending or an undesired orientation of the fluid line 619 at the sensing region 629. In some embodiments, the engagement feature 628 can have a different configuration and structure, and/or can be positioned between the apertures 626b-c.

Figure 8:
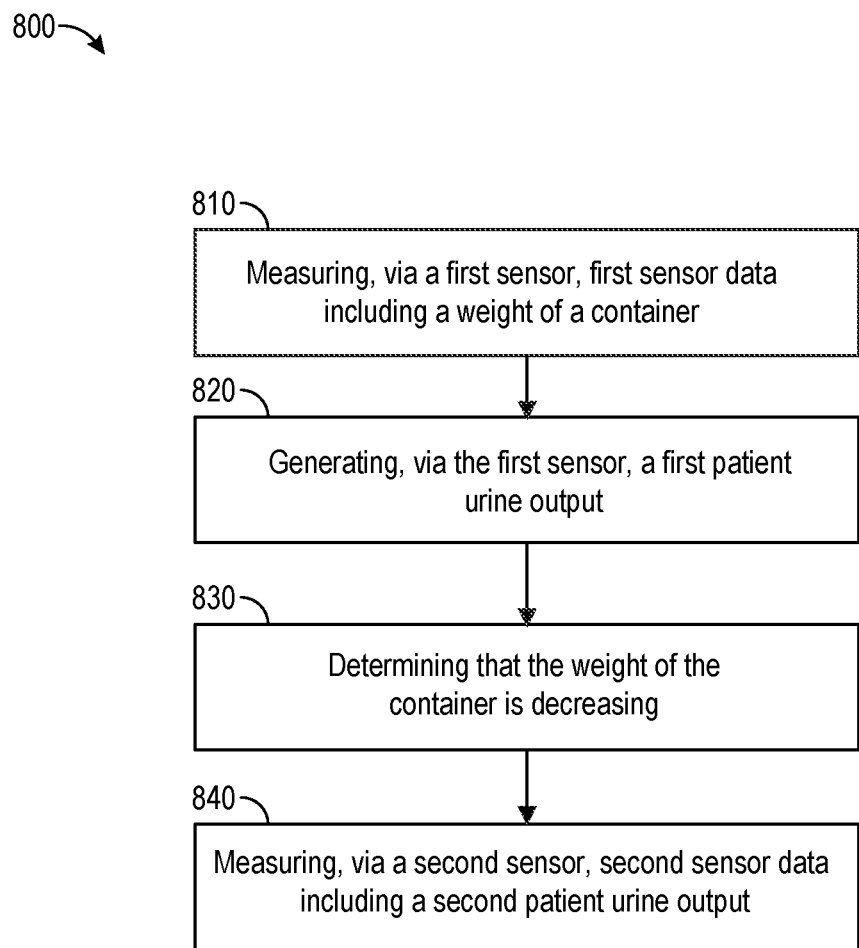
FIG. 8 is a flow diagram of a method for collecting urine from a patient, in accordance with embodiments of the present technology.

FIG. 8 is a flow diagram illustrating a method 800 for collecting urine from a patient, in accordance with embodiments of the present technology. The method 800 can be performed by embodiments of the systems and devices described herein, such as the system 160 of FIG. 1B or the system 600 of FIGS. 6A-7. In some embodiments, some or all of the stages of the method 800 are performed by a system or device including one or more processors and a memory storing instructions that, when executed by the one or more processors, cause the system or device to perform one or more of the stages described herein. For example, the method 800 can be performed by a urine system (e.g., urine system 602 of FIGS. 6A-6G) that includes or is operably coupled to a controller (e.g., controller 608 of FIG. 6A). Optionally, some or all of the stages of the method 800 can performed automatically or semi-automatically by a suitable system or device, with little or no human intervention. At least some stages of the method 800 can be generally similar or identical to one or more stages of the method 200 of FIG. 2 and/or the method 500 of FIG. 5.

The method 800 begins at stage 810 with measuring, via a first sensor (e.g., the second sensor 114b of FIG. 1B or the weight sensor 634 of FIGS. 6D-6G), first sensor data including a weight of a container (e.g., the container 112 of FIG. 1B or the container 612 of FIG. 6D). Measurement via the first sensor can occur on a continuous basis at particular intervals (e.g., every 1 second, 10 seconds, 30 seconds, 1 minute, etc.). In some embodiments, the method 800 can include, prior to measuring the weight of the container, detecting (e.g., via the first sensor) a presence of the container. In some embodiments, the method 800 can further include directing, via a flow control assembly, urine flow from the patient toward the container. The flow control assembly can correspond to the system 602 (FIGS. 6A-6G) or aspects thereof, such as the fluid line 619, the urine cartridge 620, flow control device 638.

The method 800 further includes at stage 820 generating, via the first sensor, a first patient urine output. The first patient urine output can be an average urine flow rate (e.g., volumetric flow rate) over the previous 30 seconds, 1 minute, 2 minute, or longer interval, and can be updated on a rolling basis. The first patient urine output can be based on the changing weight of the container. As described herein (e.g., with reference to FIGS. 1B and 6A-6H), the first patient urine output can be used as a primary input or source used for delivering therapy to the patient. For example, the first patient urine output can be used to determine, at least in part, the amount of diuretic and/or hydration fluid delivered to the patient.

The method 800 further includes at stage 830 determining that the weight of the container is decreasing. As described herein (e.g., with reference to FIGS. 1B and 6A-6H), the container can be drained via a drain valve (e.g., the drain valve 113; FIG. 1B) while still being fluidly coupled to the patient and/or without removing the container from the corresponding system or console. In such embodiments, draining the container can cause the weight of the container to decrease or, since the container 612 is still collecting fluid during draining, increase at a slower rate than expected. The decreasing weight or slower rate of increase of the container can cause the first urine output to cease being used as the primary source, e.g., for determining amount of diuretic and/or hydration fluid to be delivered to the patient. In some embodiments, the decreasing weight or slower rate of increase of the container can cause the current amount of diuretic and/or hydration fluid delivered to the patient to be temporarily maintained or decreased.

The method 800 further includes measuring, via a second sensor (e.g., the first sensor 114a of FIG. 1B or the flow sensor 636 of FIGS. 6D-6G), second sensor data including a second patient urine output. Measurement via the second sensor can occur on a continuous basis at particular intervals (e.g., every 1 second, 10 seconds, 30 seconds, 1 minute, etc.). The second patient urine output can be an average urine flow rate (e.g., volumetric flow rate) over the previous 30 seconds, 1 minute, 2 minute, or longer interval, and can be updated on a rolling basis.

Measuring the second sensor data can occur the entire time, including before, during, and after determining that the weight of the container is decreasing. As described herein (e.g., with reference to FIGS. 1B and 6A-6H), in some embodiments the first patient urine output determined via the first sensor data can be used as a primary input or source used for delivering therapy to the patient, but can be inaccurate at times, such as when the container is being drained. In such embodiments, the second patient urine output determined via the second sensor data may be utilized as the primary source. Additionally or alternatively, the second patient urine output may be used if the difference between the first patient urine output and the second patient urine output is at or above a predetermined threshold (e.g., a 5% difference, 10% difference, 20% difference, or 30% difference). The second patient urine output can remain as the primary source until another condition is met or event occurrence. Such conditions or events can include determining that the weight of the container is increasing, which can indicate that the container is no longer being drained, or an elapsed time (e.g., 10 second, 30 seconds, or 1 minute) after determining that the weight of the container is increasing.

In some embodiments, some or all of the stages of the method 800 are performed as part of a medical procedure for a patient. The medical procedure can be or include any diagnostic or therapeutic regimen involving monitoring the patient's urine output. For example, the medical procedure can include treating the patient for a fluid overload condition (e.g., as previously described with respect to FIGS. 1A and 2). The method 800 can be performed multiple times during the medical procedure to provide continuous or substantially continuous urine output monitoring and/or collection. Accordingly, the method 800 can advantageously reduce the number of times the healthcare professional needs to check on the status of the containers and/or empty the containers during the medical procedure.

In some embodiments, the medical procedure is performed by a semi-automated or fully automated fluid management system (e.g., the system 100 of FIG. 1A) and the method 800 is performed by a urine collection and monitoring system (e.g., the system 602 of FIGS. 6A-6G) that is included in or otherwise operably coupled to the system. In such embodiments, the operations of the system and the urine system can be coordinated. For example, once the urine system detects that the container is present and ready for use (e.g., as described in stage 810), the urine system can transmit a signal to the system to indicate that the medical procedure can begin (e.g., infusing a diuretic and/or hydration fluid into the patient to elicit urine output). As another example, the system can send a signal to the urine system to cause the urine system to switch to the second sensor (stage 860) once the urine system detects that urine is draining from the container (stage 850). As a further example, the system can send a signal to the urine system once the medical procedure has ended (e.g., the patient has exhibited the desired amount of net fluid loss, a predetermined time period has elapsed, and/or the patient has been disconnected from the urine collection system), and the urine system can automatically shut off fluid flow to the container.

Although the method 800 is described herein with in connection with one container and two sensors, in other embodiments, the method 800 can be modified to accommodate a different number of containers (e.g., two, three, four, five, or more containers) and/or sensors (e.g., three, four, five, or more sensors). In such embodiments, the method 800 can include directing urine flow into a single container at a time, and switching to the next container when the previous container is full. Alternatively, the method 800 can include directing urine flow into multiple containers concurrently, and then shutting off flow to each container individually when the container becomes full. In these and other embodiments, the method 800 can include selectively activating and/or deactivating one or more individual sensors when it is detected that urine is draining from the container.

B. Devices for Priming and/or Clearing Obstructions

In some embodiments, the urine collection systems and devices described herein use relatively small fluid lines to receive urine from the patient. For example, any of the fluid lines for described herein can have an inner diameter less than or equal to 0.5 in, 0.375 in, 0.25 in, 0.125 in, or 0.1 in. A smaller fluid line can be advantageous for maintaining a continuous or substantially continuous fluid column or volume of urine from the patient's body to the urine container (e.g., a fluid column or volume of urine including few or no gaps, air bubbles, etc., between the bladder and the container). This approach can improve the accuracy of urine output monitoring by ensuring the change in weight and/or volume at the container closely tracks the patient's actual urine production.

However, smaller fluid lines may be prone to air locks and/or other blockages that obstruct or otherwise disrupt urine flow. Air locks may also arise if air is introduced into the flow line before and/or during the urine collection procedure. For example, the fluid line can initially be primed with saline or another fluid before being connected to the patient's body. If the user does not clamp the fluid line when connecting the fluid line to the patient's body (e.g., via a catheter), the saline can flow prematurely into the container, thus introducing air into the fluid line. As another example, if the catheter is not primed with fluid when being connected into the patient's body, the air in the lumen of the catheter can enter the fluid line. The presence of air in the fluid line may lead to an air lock that partially or fully obstructs urine flow from the patient's body into the container. The obstructed urine flow can lead to a drop in measured urine output rate that does not accurately reflect the patient's actual urine output rate. Additionally, once the obstruction is cleared, urine that has pooled in the patient's bladder and/or fluid lines can be released in a large bolus, thus producing an artificially high measured urine output rate. These scenarios can interfere with monitoring urine output and/or managing fluid levels according to the processes of the present technology described herein.

Figure 9A:
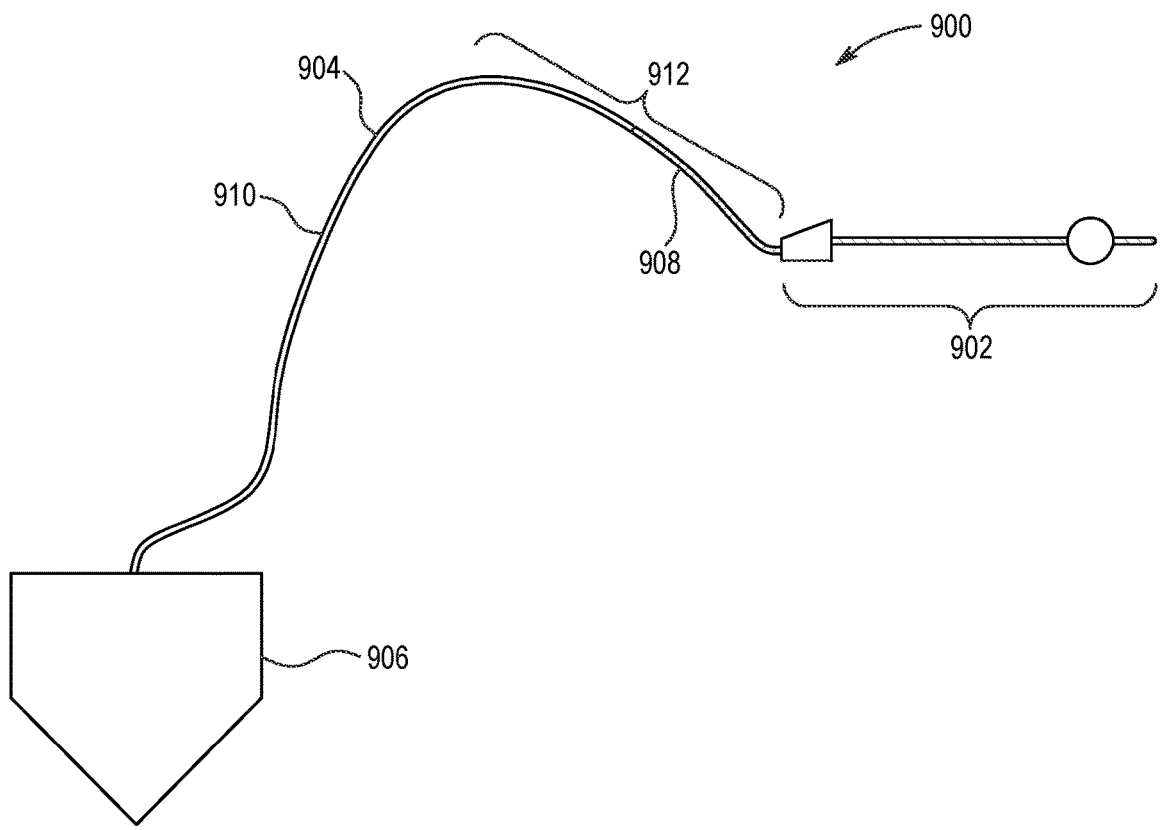
FIG. 9A illustrates an example of an air lock in a urine collection system, in accordance with embodiments of the present technology.

FIG. 9A illustrates an example of an air lock in a conventional urine collection system 900. The system 900 is coupled to a catheter 902 (e.g., a Foley catheter) which is connected to the patient's body (not shown). The system 900 includes a fluid line 904 coupled to the catheter 902 and a container 906 (e.g., a bag) coupled to the fluid line 904. In the illustrated embodiment, urine 908 from the patient is present in the catheter 902 and a portion of the fluid line 904 (indicated by hatching in FIG. 9A). The remaining portion of the fluid line 904 is filled with air 910 because the fluid line 904 includes an elevated region 912 between the catheter 902 and the container 906 that prevents further urine flow until there is sufficient internal pressure within the fluid line 904 to push the urine 908 past the elevated region 912. Once the urine 908 passes the elevated region 912, it creates a siphon to continue drawing fluid from the patient's body.

Figure 9B:
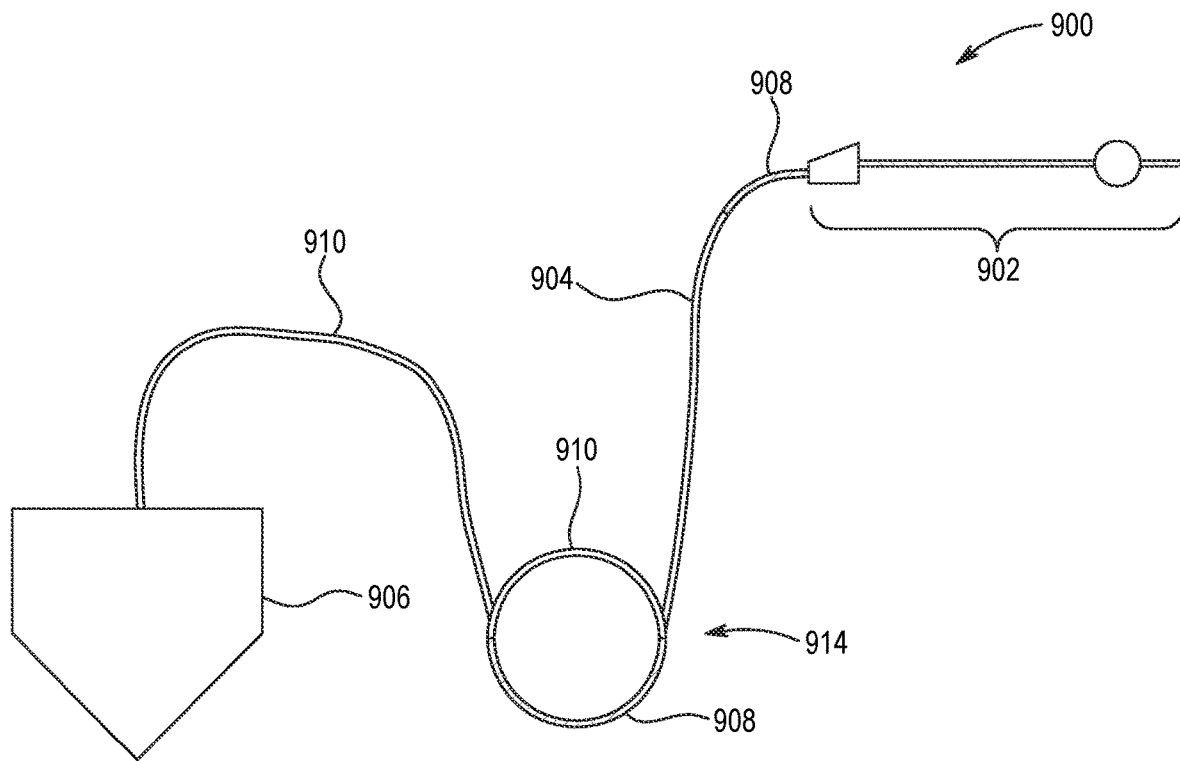
FIG. 9B illustrates another example of an air lock in a urine collection system, in accordance with embodiments of the present technology.

FIG. 9B illustrates another example of an air lock in the urine collection system 900. In FIG. 9B, the fluid line 904 includes a loop 914 between the catheter 902 and the container 906. A volume of urine 908 is trapped in the bottom of the loop 914, while the remaining portion of the loop is filled with air 910. Thus, the urine 908 is unable to flow into the container 906 until there is sufficient internal pressure within the fluid line 904 to push the air 910 and trapped urine 908 out of the loop 914. The pressure involved can cause patient discomfort and/or cause urine to leak from the around the catheter 902.

To overcome these and/or other challenges, the urine collection systems described herein can include a device for clearing air locks from a fluid line and/or priming the fluid line with a fluid (e.g., urine or saline) (also referred to herein as a "pumping device" or "priming device"). In some embodiments, the pumping device is in line with the fluid line, rather than being a separate component that is attached to the fluid line. This approach can reduce the risk of infection, since the pumping device can be sterilized with the fluid line and/or other urine collection components (e.g., catheter, container, etc.).

Figure 10:
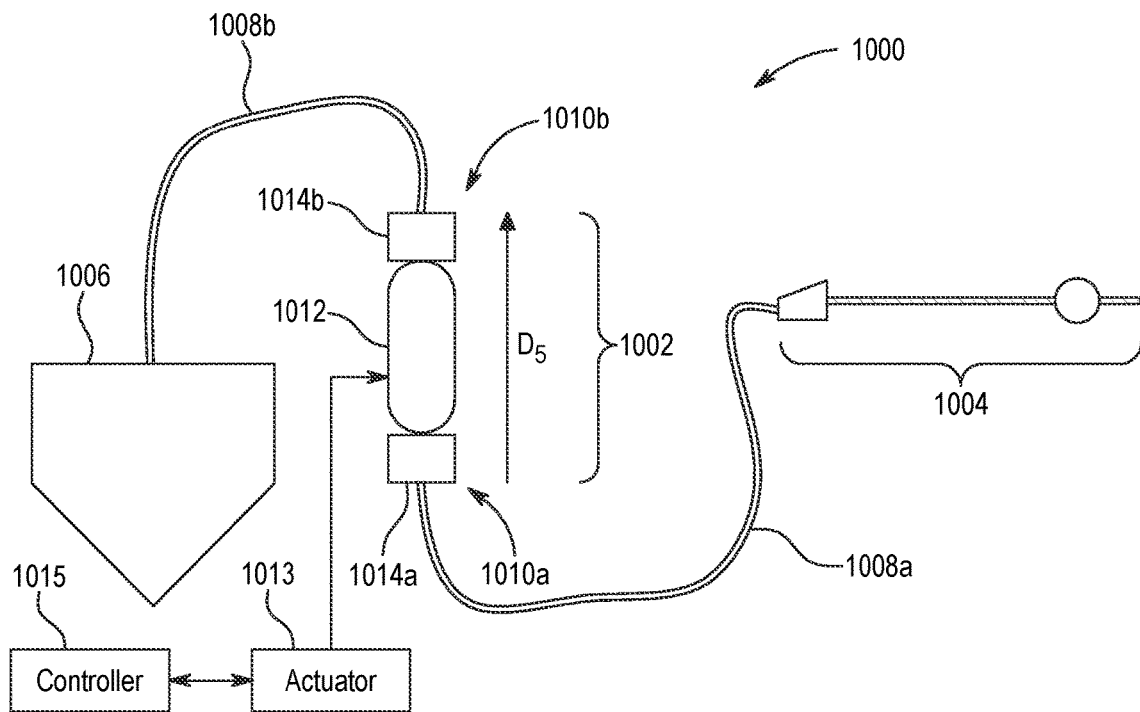
FIG. 10 is a schematic view of a urine collection system including a pumping device, in accordance with embodiments of the present technology.

FIG. 10 is a schematic view of a urine collection system 1000 including a pumping device 1002 configured in accordance with embodiments of the present technology. The system 1000 is configured to be coupled to a catheter 1004 (e.g., a Foley catheter), which can be connected to the patient's body (not shown). The system 1000 includes a container 1006 (e.g., a bag), a first fluid line 1008a fluidly coupling the catheter 1004 to the pumping device 1002, and a second fluid line 1006b fluidly coupling the pumping device 1002 to the container 1008. The pumping device 1002 is in line with the first and second fluid lines 1008a-b and is between the catheter 1004 and the container 1006. In some embodiments, the pumping device 1002 is located closer to the container 1006 than the catheter 1004, which can reduce the likelihood of the pumping device 1002 becoming caught on the patient's clothing and/or body, which can disconnect the catheter 1004 and/or apply force to the catheter 1004 that causes patient discomfort. For example, the length of the second fluid line 1008b between the pumping device 1002 and the container 1006 can be less than or equal to 100 cm, 50 cm, 40 cm, 30 cm, 20 cm, 10 cm, or 5 cm.

The pumping device 1002 can be a hollow structure or member including a lumen for fluid flow (e.g., urine, saline, air, etc.). In the illustrated embodiment, the pumping device 1002 includes a first end portion 1010a connected to the first fluid line 1008a, a second end portion 1010b connected to the second fluid line 1008b, and a flexible body portion 1012 between the first and second end portions 1010a-b. The flexible body portion 1012 can be a deformable bulb, balloon, chamber, etc., made of an elastic material (e.g., a polymeric and/or elastomeric material). The flexible body portion 1012 can be actuatable between a resting and/or unloaded configuration, and a loaded configuration. In some embodiments, the flexible body portion 1012 is actuated multiple times to incrementally pump fluid from the first fluid line 1008a, through the pumping device 1002, and into the second fluid line 1008b. For example, the flexible body portion 1012 can be compressed manually by a user (e.g., squeezed by hand), by an actuator 1013 (e.g., a servomotor or other electromechanical device), or suitable combinations thereof.

In some embodiments, the pumping device 1002 is configured to permit fluid flow in a single direction, e.g., from the first fluid line 1008a and into the first end portion 1010a, and from the second end portion 1010b into the second fluid line 1008b, as indicated by direction $D_5$ in FIG. 10. The pumping device 1002 can also restrict fluid flow in the opposite direction, such as from the second fluid line 1008b into the second end portion 1010b, and/or from the first end portion 1010a into the first fluid line 1008a. This unidirectional flow can reduce or prevent fluid backflow toward the patient's body to protect the patient from infection.

For example, in the embodiment of FIG. 10, the first end portion 1010a of the pumping device 1002 includes a first (e.g., proximal) valve 1014a, and the second end portion 1010b of the pumping device 1002 includes a second valve 1014b. The first valve 1014a can allow fluid flow from the first fluid line 1008a into the flexible body portion 1012, while restricting fluid flow from the flexible body portion 1012 into the first fluid line 1008a. Similarly, the second valve 1014b can allow fluid flow from the flexible body portion 1012 into the second fluid line 1008b, and can restrict fluid flow from the second fluid line 1008b into the flexible body portion 1012. The first and second valves 1014a-b can each be or include a check valve or other unidirectional flow mechanism. Examples of check valves include, but are not limited to, ball check valves (e.g., ball-in-cage check valves), swing check valves, diaphragm check valves, lift-check valves, duckbill check valves, and the like. In some embodiments, the first and second valves 1014a-b have little or no "crack pressure" (the pressure to open the valve in the forward flow direction) so that urine and/or other fluid can flow through the pumping device 1002 freely along direction $D_5$ when the pumping device 1002 is not being actuated. This can avoid issues with fluid build-up in the bladder due to insufficient fluid pressure to open the valves.

When the flexible body portion 1012 is compressed, the pressure within the flexible body portion 1012 can increase, thus closing the first valve 1014a and opening the second valve 1014b. Accordingly, fluid (e.g., air, urine, saline, etc.) can be pushed forward from the flexible body portion 1012 into the second fluid line 1008b, and/or from the second fluid line 1008b into the container 1006. In the illustrated embodiment, because the second end portion 1010b is higher than the first end portion 1010a, any air within the flexible body portion 1012 can rise to the top and thus be expelled first when the flexible body portion 1012 is compressed. When the flexible body portion 1012 is released, the elasticity of the flexible body portion 1012 can cause the flexible body portion 1012 to revert toward its resting configuration, thus decreasing the pressure within the flexible body portion 1012. The pressure drop can close the second valve 1014b and open the first valve 1014a. The pressure drop can also create a vacuum that draws fluid from the first fluid line 1008a, upward through the first end portion 1010a, and into the flexible body portion 1012. In some embodiments, little or no air external to the patient's body is drawn into the first and second fluid lines 1008a-b, pumping device 1002, container 1006, and/or catheter 1004 throughout the actuation process, such that the system 1000 remains closed to reduce the risk of infection.

The actuation process described herein can be repeated multiple times to incrementally pump fluid through the first and second fluid lines 1008a-b toward the container 1006. For example, the actuation process can be performed at the start of a medical procedure to prime the system 1000 by drawing urine from the patient's bladder and into the container 1006, thus creating a continuous column or volume of urine from the patient's body to the container 1006. The continuous column of urine can create a siphon that actively draws urine from the patient's body, thus reducing or eliminating any dead volume within the bladder. The siphon can also ensure that there is little or no delay from the time urine is produced in the patient's body to the time the urine reaches the container 1006, which can improve the accuracy of the urine monitoring techniques described herein. Optionally, if the patient's bladder is empty or substantially empty after the flexible body portion 1012 has been squeezed, the flexible body portion 1012 can remain in the compressed configuration due to its compliant properties. This can reduce or minimize the sustained vacuum on the patient's bladder, which can decrease the likelihood of suction injury due to the catheter inlet being sucked against the bladder wall.

As another example, the actuation process can be performed during a medical procedure to clear air locks and/or other obstructions from the first and/or second fluid lines 1008a-b. In some embodiments, repeated actuation of the pumping device 1002 can push trapped air out of the first and/or second fluid lines 1008a-b and into the container 1006. Similar to the priming process described above, the repeated actuation can also draw urine out of the patient's bladder and through the first and/or second fluid lines 1008a-b to create a continuous column of urine throughout the system 1000.

In a further example, the pumping device 1002 can be used to diagnose potential issues in the system 1000. For instance, if the flexible body portion 1012 is squeezed, but does not automatically re-inflate and fill with urine, this may indicate one or more of the following situations: (1) one or more components within or outside the patient's body (e.g., the catheter 1004, first fluid line 1008a, second fluid line 1008b) are kinked; (2) the catheter 1004 is against the bladder wall or is otherwise unable to draw fluid from the bladder; (3) there is a clog in the catheter 1004, first fluid line 1008a, and/or second fluid line 1008b; and/or (4) the patient's bladder is empty.

In some embodiments, a user (e.g., a nurse or other healthcare professional) manually actuates the pumping device 1002 to prime the system 1000 with fluid and/or clear air locks from the system 1000. In other embodiments, however, the actuation can be performed automatically or semi-automatically by the actuator 1013 coupled to the pumping device 1002. The actuator 1013 can be operably coupled to a controller 1015 (e.g., the controller 140 of the system 100 of FIG. 1A) and/or urine collection system (e.g., system 300 of FIG. 3, system 400 of FIGS. 4A-4J, and/or system 600 of FIGS. 6A-6G). For example, during a setup process for a medical procedure (e.g., a procedure to treat fluid overload), the controller 1015 can operate the actuator 1013 to actuate the pumping device 1002 to prime the first and second fluid lines 1008a-b with fluid. The priming can be performed in response to a suitable signal, such as user input indicating that the first and second fluid lines 1008a-b have been connected to the patient's body via the catheter 1004. As another example, during the medical procedure, the controller 1015 can detect whether an air lock or other obstruction is present (e.g., based on sensor data indicating an unexpected drop in urine output rate, changes in pressure, and/or other suitable indicators), and can actuate the pumping device 1002 until the air lock has been cleared (e.g., based on sensor data indicating that urine output has resumed). The controller 1015 can additionally actuate the pumping device 1002 to maintain urine flow through the first and second fluid line 1008a-b during the procedure.

Figure 11:
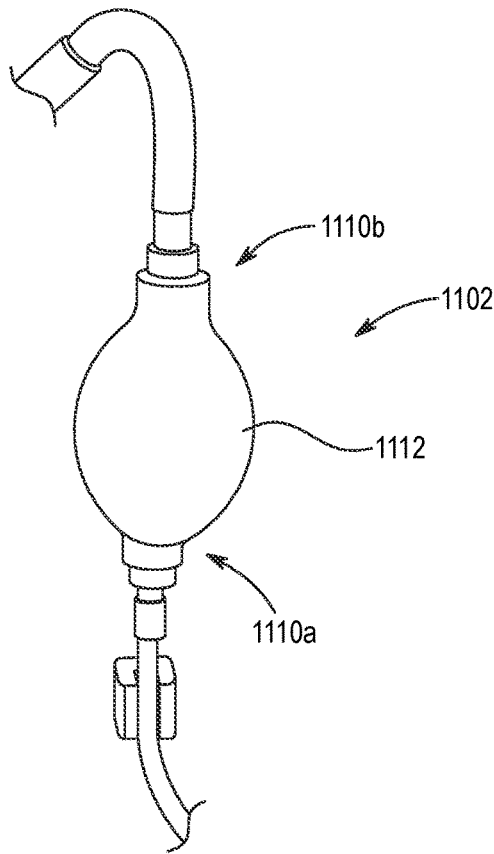
FIG. 11 is a perspective view of a priming bulb, in accordance with embodiments of the present technology.

FIG. 11 is a perspective view of a priming bulb 1102 configured in accordance with embodiments of the present technology. The priming bulb 1102 can serve as the pumping device 1002 in the system 1000 of FIG. 10. As shown in FIG. 11, the priming bulb 1102 includes a first end portion 1110a including a first check valve (not shown), a second end portion 1110b including a second check valve (not shown), and a flexible body portion 1112 between the first and second end portions 1110a-b. The flexible body portion 1112 can have a rounded shape suitable for squeezing by hand and/or by an actuator. Optionally, the flexible body portion 1112 can be transparent or translucent to allow the user to view the amount of fluid within the flexible body portion 1112. In some embodiments, the size of the priming bulb 1102 is sufficiently large so the priming bulb 1102 can pump fluid with a relatively small number of compressions (e.g., less than ten, five, four, three, or two compressions), but not so large that an excessive amount of force is needed to compress the priming bulb 1102. For example, the interior volume of the priming bulb 1102 can be within a range from 10 ml to 50 ml, or within a range from 20 ml to 30 ml.

Referring again to FIG. 10, the system 1000 can alternatively or additionally use other types of pumping devices to prime the first and second fluid lines 1008a-b and/or to clear air locks, such as peristaltic pumps, syringe pumps, and the like. For example, in other embodiments, a T-shaped fitting could be installed between the first fluid line 1008a and second fluid line 1008b, with a check valve on between each end of the T-shaped fitting and the corresponding fluid line. The check valves can be oriented to allow fluid flow from the patient's body to the container 1006 (e.g., similar to the first and second valves 1014a-b), while limiting fluid flow in the opposite direction. A syringe mechanism can be connected to the third leg of the T-shaped fitting. The syringe mechanism can be drawn back to create a vacuum that pulls fluid from the bladder into the first fluid line 1008a and/or syringe body. The syringe mechanism can then be depressed to force fluid from the syringe body and/or second fluid line 1008b into the container 1006. This process can be repeated to clear an air lock and/or create a column of urine for proper flow. Optionally, the syringe mechanism can then be decoupled from the T-shaped fitting, and the third leg of the T-shaped fitting can be blocked with a stopcock or other sealing element. Alternatively, the third leg can include a needleless luer connector or other element that automatically seals when the syringe mechanism is removed.

Figure 12:
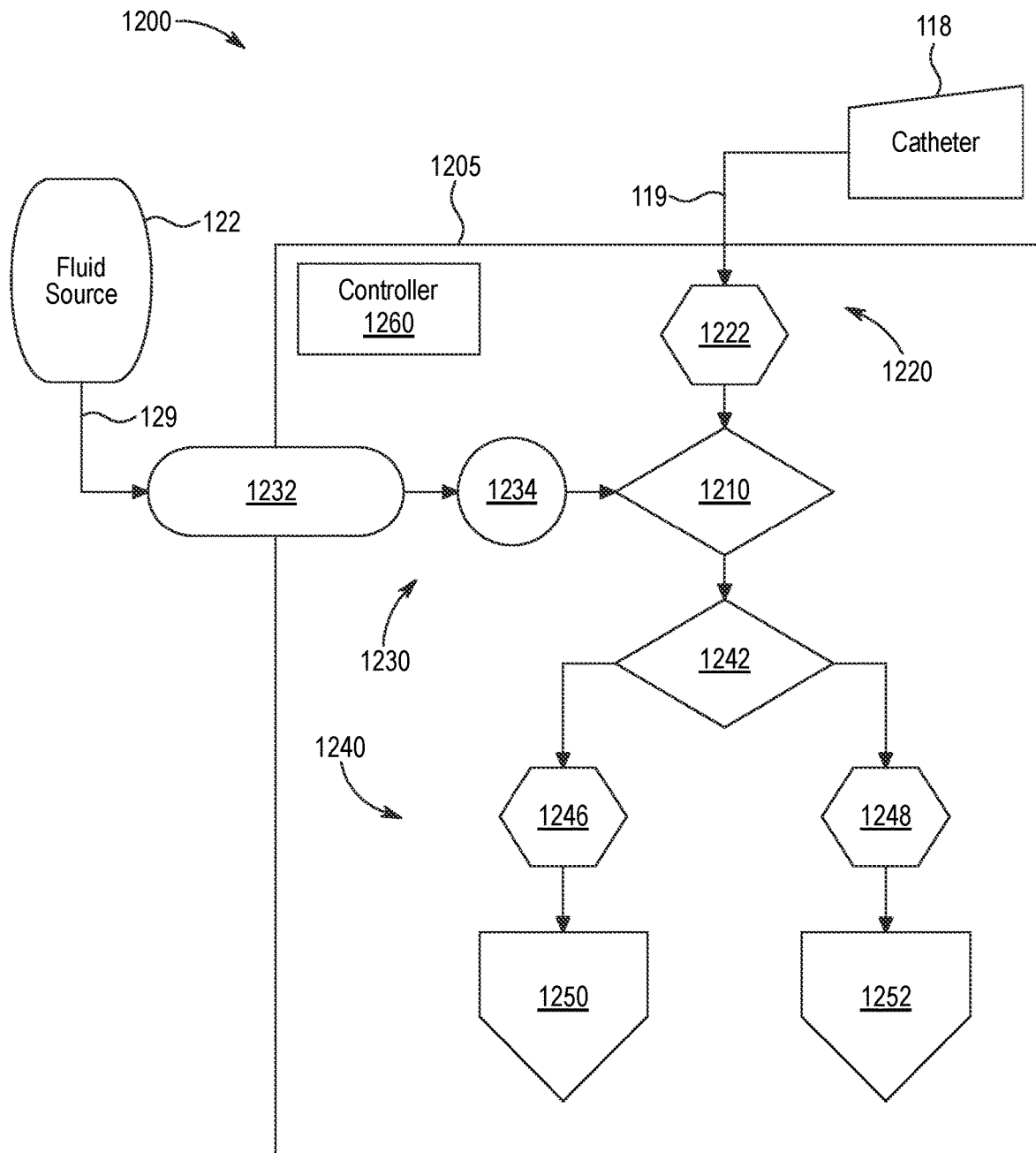
FIGS. 12-14B illustrate examples of schematic urine collection systems, in accordance with embodiments of the present technology.

In some embodiments, catheters supplied from manufacturers are pre-connected to urine drain lines and containers, which can make priming of the entire tubing system associated with catheter more difficult. Some embodiments of the present technology include systems, devices, and methods for priming such systems. FIG. 12, for example, illustrates a schematic urine collection system 1200, in accordance with embodiments of the present technology. As shown in FIG. 12, the system 1200 can include a device 1205 (e.g., a cartridge) configured to be fluidly coupled to the fluid source 122 (as previously described with reference to FIG. 1A) via the fluid line 129 and to the catheter 118 (as previously described with reference to FIG. 1A) via the fluid line 119. The device 1205 can include (i) a coupler 1210 (e.g., a T-fitting), (ii) a first supply line 1220 fluidly coupled to a first inlet of the coupler 1210 and including a valve 1222 positioned between and configured to regulate fluid from the catheter 118, and (iii) a second supply line 1230 fluidly coupled to a second inlet of the coupler 1210 and including a port 1232 (e.g., a luer connector or needleless luer connector) configured to be fluidly coupled to the fluid source 122, and optionally a valve 1234 (e.g., a check valve) positioned between the port 1232 and the coupler 1210. The port 1232, when disconnected from the fluid line 129 and/or fluid source 122, can be configured to prevent any fluid outflow from the second supply line 1230. The valve 1234 can be configured to prevent any back flow of fluid to the fluid line 129 and/or fluid source 122. The device 1205 can further include an outlet line 1240 fluidly coupled to an outlet of the coupler 1210. The outlet line 1240 can include a connector 1242 having a first end fluidly coupled to a valve 1246 and a first container 1250 downstream of the valve 1246, and a second end fluidly coupled to a valve 1248 and a second container 1252 downstream of the valve 1248. The system 1200 and/or device 1205 can further include a controller 1260 operably coupled at least to the valves 1222, 1246, 1248, and thus configured to regulate fluid flow through the device 1205. The controller 1260 can be the same as or similar to the controller 140 described elsewhere herein.

The system 1200 can be used to prime the device 1205 with fluid (e.g., saline) from the fluid source 122 and thereby remove air from the system 1200. In doing so, the system 1200 can maintain a continuous or substantially continuous fluid column or volume of urine from the patient's body to the container(s) 1250, 1252 (e.g., a fluid column or volume of urine including few or no gaps, air bubbles, etc., between the bladder and the container). As previously described, this approach can improve the accuracy of urine output monitoring by ensuring that the change in weight and/or volume at the container(s) 1250, 1252 closely tracks the patient's actual urine production. Additionally, the column of fluid generated by priming can generate a vacuum or negative pressure (e.g., less than or equal to 0.5 psi) in the bladder once the catheter 118 is connected to the patient. This can increase the removal of urine from the bladder and/or stimulate additional urine production.

In operation, fluid from the fluid source 122 can be infused to the device 905 to remove air in the first supply line 1220, second supply line 1230, and outlet line 1240. For example, one method of priming the system 1200 can include closing valves 1222, 1246, 1248, and fluidly coupling the fluid source 122 to the coupler 910 via the fluid line 129, port 932 and valve 1234. Valves 1246, 1248, and 1250 can then be individually opened and closed to allow fluid flow therethrough and air to be purged. For example, after infusing fluid from the fluid source through the port 1232 and valve 1234, (i) the valve 1246 can be opened and then closed once the line between the connector 1242 and container 1250 is filled with fluid, (ii) the valve 1248 can be opened and then closed once the line between the connector 1242 and container 1252 is filled with fluid, and (iii) the valve 1222 can be opened to flow fluid from the coupler 1210 through the valve 1222 and fluid line 119 to the catheter 118, and then closed once the line between the valve 1222 and catheter 118 is filled with fluid. The above-described method can be performed manually by a user, or automatically via the controller 1260. Once priming is complete, the catheter 118 can be inserted into the patient. Advantageously, by priming the system 1200 prior to connecting the catheter 118 to the patient, embodiments of the present technology can decrease the likelihood of catheter acquired urinary tract infection (CAUTI) relative to systems that do not or are unable to prime the system in the manner described herein.

Figure 13:
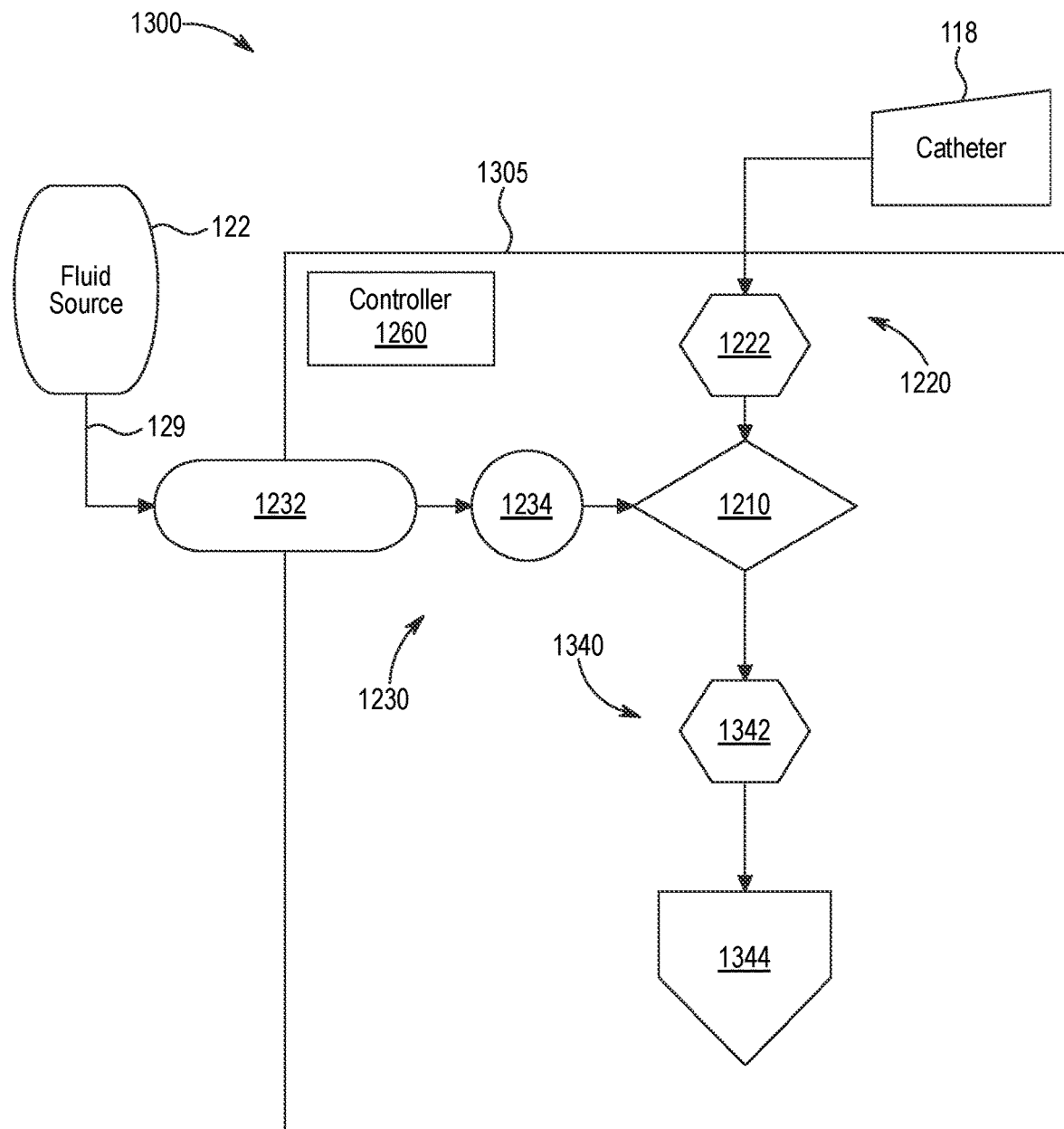

FIG. 13 illustrates another example of a schematic urine collection system 1300 in accordance with embodiments of the present technology. The system 1300 includes a device 1305 having many of the same features and functionality of the device 1205, but only includes a single container instead of multiple containers. As shown in FIG. 13, the device 1205 includes an outlet line 1340 fluidly coupled to an outlet of the coupler 1210, in which the outlet line 1240 includes a valve 1342 and a container 1344 downstream of the valve 1342. Priming of the system 1300 is substantially the same as the method for priming the system 1000 described herein.

Figure 14A:
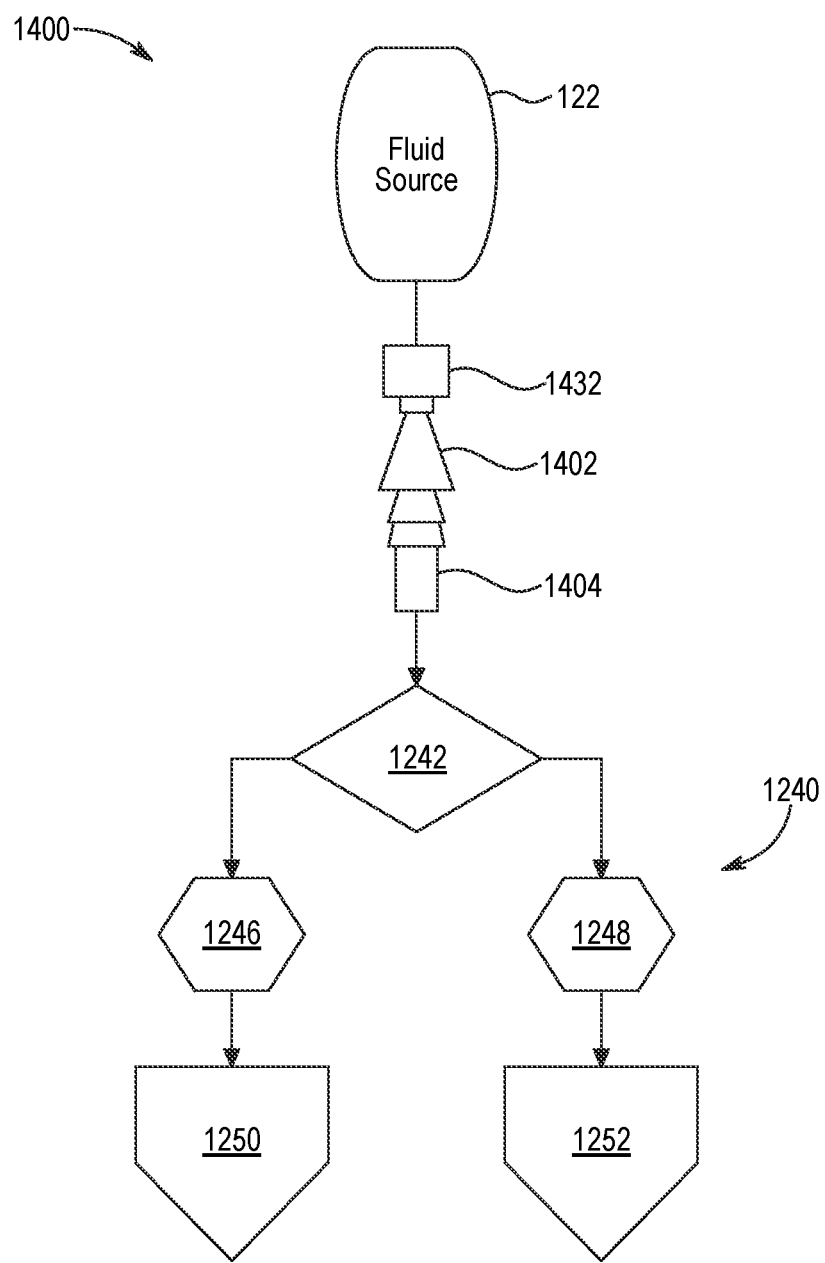
Figure 14B:
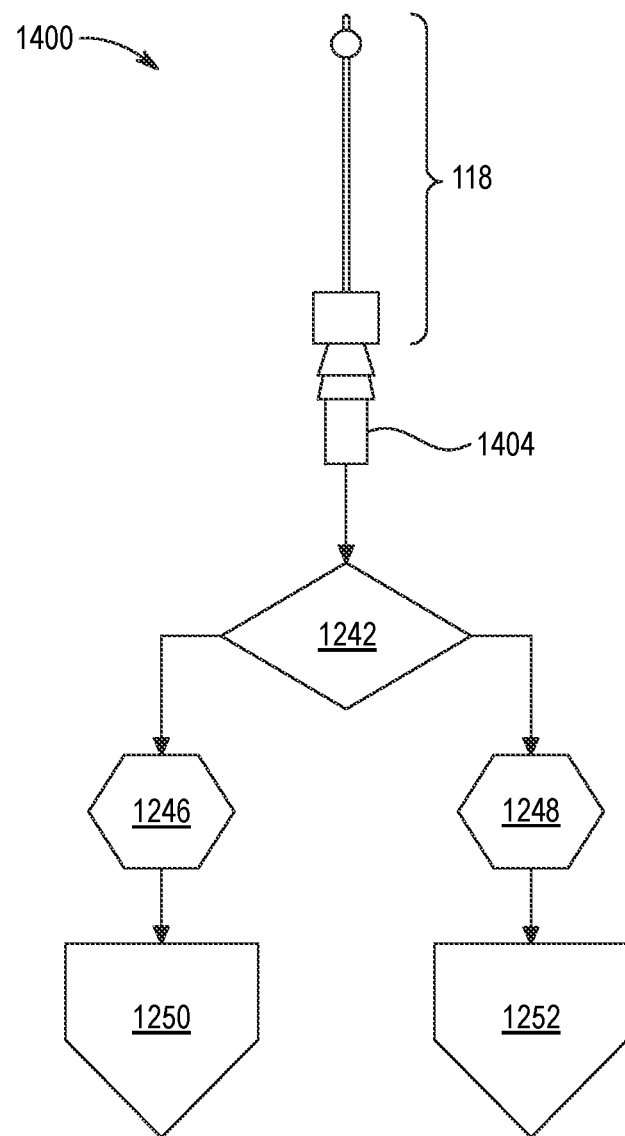

As previously described, some catheters supplied from manufacturers are not pre-connected to urine drain lines and containers. For such catheters, alternative systems, devices, and methods different from those described in FIGS. 12 and 13 may be used to prepare such catheters and related devices for use. FIGS. 14A and 14B, for example, illustrate a schematic urine collection system 1400, in accordance with embodiments of the present technology. As shown in FIG. 14A, the system 1400 can include the fluid source 122 and port 1232 (as previously described in FIGS. 12 and 13), as well as an adapter 1402 (e.g., an adapter including an outlet luer fitting) coupled to and downstream of the port 1232, a connector 1404 coupled to and downstream of the adapter 1402, and the outlet line 1240 (as previously described in FIGS. 12 and 13) coupled to and downstream of the connector 1404. The outlet line 1240 can include the connector 1242 having a first end fluidly coupled to the valve 1246 and the first container 1250 downstream of the valve 1246, and a second end fluidly coupled to the valve 1248 and the second container 1252 downstream of the valve 1248. In some embodiments, the outline line 1240 may only include a single container.

In operation, the system 1400 can be primed by infusing fluid from the fluid source 122 through the port 1232, adapter 1402, connector 1404, and outlet line 1240. As previously described, the valves 1246, 1248 can be individually opened and closed until fluid fills the corresponding lines. Once the system 1400 is primed, and the valves 1246, 1248 are closed, the fluid source 122 can be decoupled from the connector 1404. Referring next to FIG. 14B, the catheter 118 can be coupled to the connector 1404 and then inserted into the patient for use.

Figure 15A:
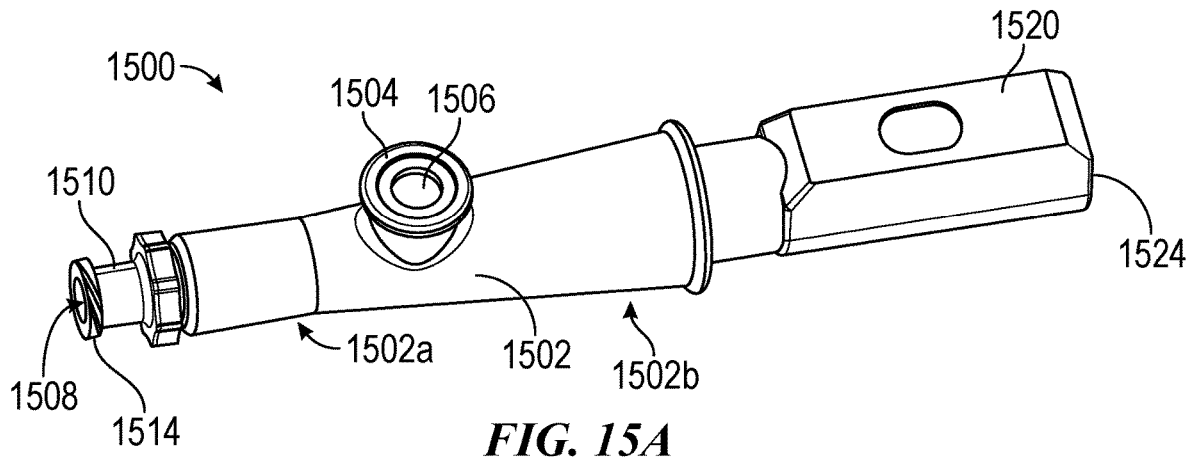
FIGS. 15A and 15B are perspective and cross-sectional views, respectively, of a priming assembly, in accordance with embodiments of the present technology.
Figure 15B:
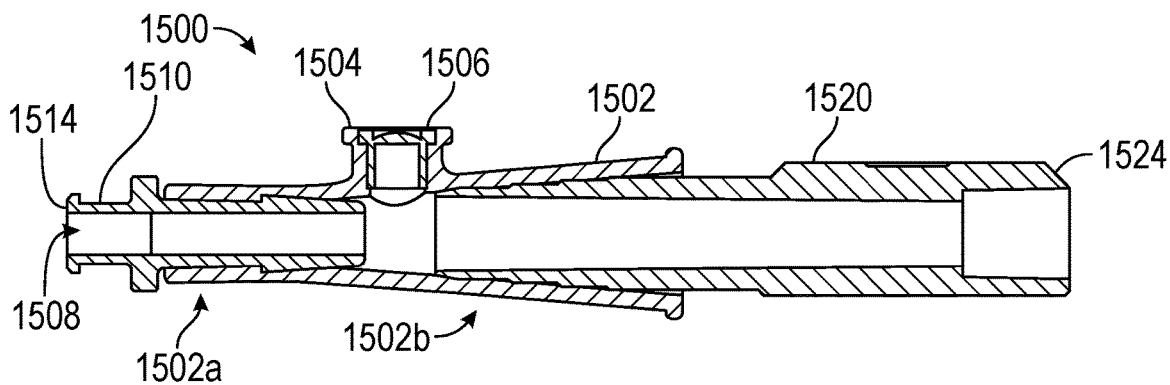

FIGS. 15A and 15B are perspective and cross-sectional views, respectively, of another pumping and/or priming assembly 1500 ("assembly 1500") configured in accordance with embodiments of the present technology. The assembly 1500 can include an elongate adapter body 1502 having a first end portion 1502a and a second end portion 1502b opposite the first end portion 1502a. The body 1502 can include a priming element 1506 contained at least partially within a priming portion 1504. In the illustrated embodiment, the priming portion 1504 has a cylindrical shape and extends radially outward from the body 1502 in a direction generally perpendicular to a longitudinal axis of the body 1502. In other embodiments the priming portion 1504 can have any other shape and/or configuration. The priming element 1506 can be generally flexible and configured to bend or flex within the priming portion 1054, for example, to drive fluid flow through the assembly 1500 to prime the assembly 1500 and/or one or more components connected thereto. In some embodiments, the priming element 1506 can include an air filter, such as a X5008 hydrophobic air filter marketed by Qosina Corp., headquartered in Ronkonkoma, New York, or any other suitable air filter.

The body 1502 can be configured to receive one or more components. In the illustrated embodiment, for example, the first end portion 1502a of the body 1502 is configured to receive a first fluid line coupling component 1510 ("first component 1510") and a second fluid line coupling component 1520 ("second component 1520"). The first component 1510 can include fitting 1514 configured to couple a fluid line (e.g., the fluid line 119 of FIG. 1A) or another suitable portion of a fluid management system. The second component 1520 can include a port 1524 configured to couple to a Foley catheter (e.g., the Foley catheter 118 of FIG. 1B). The body 1502, the first component 1510, and the second component 1520 can each be hollow and define an overall lumen 1508 extending through the assembly 1500. In some embodiments, the first component 1510 includes a barb fitting, such a 61764 barb fitting marketed by Qosina Corp., or any other suitable barb fitting. In some embodiments, the second component 1520 includes a Foley catheter adapter, such as a 09-875-7104 Sample Port Connector manufactured by Carmo A/S, based in Denmark, or any other suitable Foley catheter adapter.

Figure 15C:
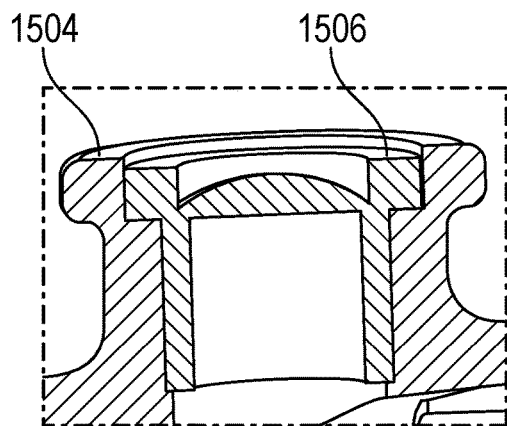
FIGS. 15C and 15D are cross-sectional views of portions of the priming assembly of FIGS. 15A and 15B.
Figure 15D:
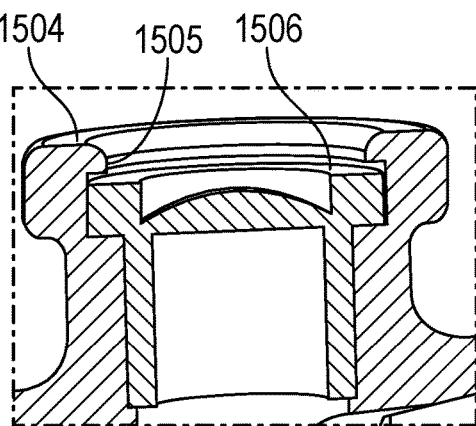

FIGS. 15C and 15D are enlarged cross-sectional views of the priming portion 1504 in accordance with embodiments of the present technology. Referring to FIG. 15C, in some embodiments the priming element 1506 can be press-fit within the priming portion 1504. Referring to FIG. 15D, in some embodiments the priming portion 1504 can include an annular lip or rim 1505, and the priming element 1506 can be positioned beneath the rim 1505.

Referring to FIGS. 15A-15D together, priming of the assembly 1500 is substantially the same as the method for priming the system 1000 described herein. For example, the priming element 1506 can be repeated pressed in a radially inward direction to remove air from one or more fluid lines and/or other components of a fluid management system coupled to the assembly 1500.

Any of the pumping and/or priming devices described herein can be incorporated into any of the other systems and devices described herein. For example, the pumping device 1002 of FIG. 10 can be incorporated in any fluid line that receives urine from a patient, such as the fluid line 119 of FIG. 1A, the fluid lines 426a and/or 426b of FIGS. 4A-4J, and so on. Similarly, any of the processes for priming the fluid line and/or clearing obstructions from the fluid line described herein can be performed before and/or during any of the treatment procedures of the present technology.

III. CONCLUSION

The present technology is illustrated, for example, according to various aspects described below. Various examples of aspects of the present technology are described as numbered examples (1, 2, 3, etc.) for convenience. These examples do not limit the present technology. It is noted that any of the dependent examples may be combined in any combination, and placed into a respective independent example.

EXAMPLES

1. A system for collecting urine from a patient, the system comprising:
   a first container;
   a second container;
   at least one sensor configured to generate sensor data indicative of an amount of urine in the first and second containers; and
   a flow control assembly configured to direct a urine flow from the patient into the first container or the second container, based on the sensor data.
2. The system of example 1 wherein the at least one sensor includes one or more of the following: a weight sensor, a flow sensor, or a fluid level sensor.
3. The system of example 1 or example 2 wherein the sensor data includes first sensor data indicative of a first amount of urine in the first container and second sensor data indicative of a second amount of urine in the second container.
4. The system of example 3 wherein the flow control assembly is configured to direct the urine flow away from the first container and into the second container when the first sensor data indicates that the first amount of urine exceeds a threshold value.
5. The system of example 4, further comprising at least one second sensor configured to detect presence of the second container, wherein the flow control assembly is configured to direct the urine flow into the second container when the first amount of urine exceeds the threshold value and the second container is present.
6. The system of example 4 or example 5, further comprising a notification device configured to output a notification when the first amount of urine exceeds the threshold value.
7. The system of example 6, wherein the notification includes one or more of the following: a light, a sound, a message displayed on a user interface of the system, or a message transmitted to a separate device.
8. The system of any one of examples 1-7 wherein the flow control assembly includes:
   a first valve coupled to the first container,
   a second valve coupled to the second container, and
   at least one actuator configured to actuate the first and second valves to control fluid flow into the first and second containers, respectively.
9. The system of example 8 wherein the first and second valves each include a rotatable cam unit.
10. The system of any one of examples 1-9, further comprising:
    a first retainer configured to secure to the first container to the flow control assembly, and
    a second retainer configured to secure the second container to the flow control assembly.
11. The system of example 10 wherein the flow control assembly is configured to:
    lock the first retainer and unlock the second retainer when the urine flow is being directed into the first container, and
    lock the second retainer and unlock the first retainer when the urine flow is being directed into the second container.
12. The system of any one of examples 1-11 wherein the flow control assembly is coupled to a catheter on or in the patient's body.
13. A method for collecting urine from a patient, the method comprising:
    directing, via a flow control assembly, a urine flow from the patient into a first container;
    measuring, using at least one sensor, an amount of urine within the first container;
    detecting, using at least one sensor, that the amount of urine within the first container exceeds a threshold value; and
    actuating the flow control assembly to direct the urine flow away from the first container and into a second container.
14. The method of example 13, further comprising measuring, using at least one second sensor, an amount of urine within the second container.
15. The method of example 14 wherein the urine flow is directed away from the first container and into the second container when (1) the amount of urine within the first container exceeds the threshold value and (2) the amount of urine within the second container is below the threshold value.
16. The method of example 15, further comprising:
    detecting, using the at least one sensor, that the amount of urine in the first container is below the threshold value,
    detecting, using the at least one second sensor, that the amount of urine within the second container exceeds a threshold value; an and
    actuating the flow control assembly to direct the urine flow away from the second container and into the first container.
17. The method of any one of examples 13-16, further comprising detecting, using at least one third sensor, whether the second container is present.
18. The method of example 17 wherein the urine flow is directed away from the first container and into the second container when (1) the amount of urine within the first container exceeds the threshold value and (2) the second container is present.
19. The method of any one of examples 13-18, further comprising:
    locking the first container to the flow control assembly when the urine flow is being directed into the first container, and
    unlocking the first container from the flow control assembly when the urine flow is being directed into the second container.
20. The method of any one of examples 13-19, further comprising outputting a notification indicating that the amount of urine within the first container exceeds the threshold value.
21. The method of any one of examples 13-20, further comprising:
    detecting, using at least one fourth sensor, whether one or more of the first or second containers are present, and
    outputting a first signal indicating that a medical procedure for the patient can begin.
22. The method of example 21 wherein the medical procedure includes treating the patient for a fluid overload condition.

23. The method of example 21 or example 22 wherein the medical procedure includes monitoring urine output of the patient.
24. The method of any one of examples 21-23, further comprising:
    receiving a second signal indicating that the medical procedure has ended, and
    unlocking one or more of the first or second containers from the flow control assembly.
25. A device for collecting urine from a patient, the device comprising:
    a first fluid line configured to couple to the patient's body;
    a second fluid line configured to couple to a urine container; and
    a hollow member including:
        a first end portion coupled to the first fluid line, the first end portion including a first check valve;
        a second end portion coupled to the second fluid line, the second end portion including a second check valve; and
        a flexible body portion fluidly coupling the first and second end portions to allow fluid flow from the patient's body to the urine container.
26. The device of example 25 wherein:
    the first check valve is configured to restrict fluid flow from the hollow member into the first fluid line, and
    the second check valve is configured to restrict fluid flow from the second fluid line into the hollow member.
27. The device of example 25 or example 26 wherein the flexible body portion is actuatable between a resting configuration and a compressed configuration.
28. The device of example 27 wherein the flexible body portion is configured to be repeatedly actuated to move air from one or more of the first or second fluid lines into the urine container.
29. The device of example 27 or example 28 wherein the flexible body portion is configured to be repeatedly actuated to draw fluid from the patient's body into one or more of the first or second fluid lines.
30. The device of any one of examples 27-29 wherein the flexible body portion is configured to be manually actuated.
31. The device of any one of examples 27-30 wherein the flexible body portion is configured to be actuated by an automated mechanism.
32. The device of any one of examples 25-31 wherein, when in use, the hollow member is oriented with the second end portion above the first end portion.
33. The device of any one of examples 25-32 wherein one or more of the first or second fluid lines have an inner diameter less than or equal to 1/8 inch.
34. The device of any one of examples 25-33, further comprising a catheter configured to couple the first fluid line to the patient's body.
35. A method for collecting urine from a patient, the method comprising:
    connecting a urine container to the patient's body via at least one fluid line, wherein the at least one fluid line is fluidly coupled to a pumping device between the patient's body and the urine container;
    actuating a flexible body portion of the pumping device to move fluid through the at least one fluid line and toward the urine container; and
    restricting fluid flow away from the urine container via at least one valve of the pumping device.
36. The method of example 35 wherein the actuating includes compressing the flexible body portion one or more times.
37. The method of example 35 or 36, further comprising detecting an air lock in the at least one fluid line, wherein the actuating is performed to clear the air lock.
38. The method of any one of examples 35-37 wherein the actuating is performed to draw urine from the patient's body into the at least one fluid line.
39. The method of any one of examples 35-38 wherein the actuating is performed during a medical procedure to treat the patient for fluid overload.
40. The method of any one of examples 35-39 wherein the at least one valve includes at least one check valve.
41. The method of any one of examples 35-40 wherein the at least one fluid line includes a first fluid line connected to the patient's body and a second fluid line connected to the urine container, and the pumping device fluidly couples the first fluid line to the second fluid line.
42. A system configured to collect urine from a patient, comprising:
    a coupler including a first inlet, a second inlet, and an outlet;
    a first line coupled to the first inlet of the coupler and configured to be fluidly coupled to a fluid source;
    a second line coupled to the second inlet of the coupler and including a first valve, the second line being configured to be fluidly coupled to a catheter or patient; and
    a third line coupled to the outlet of the coupler and including a second valve and a container downstream of the second valve.
43. The system of example 42, wherein the first line includes a port configured to be fluidly coupled to the fluid source, and a check valve between the port and the coupler.
44. The system of example 43, wherein the port is a needleless luer connector.
45. The system of any one of examples 42-44, further comprising a controller operably coupled to and configured to regulate the first valve and the second valve.
46. The system of any one of examples 42-45, further comprising the fluid source, wherein the fluid source comprises saline.
47. The system of any one of examples 42-46, further comprising the catheter, wherein the catheter is a Foley catheter.
48. The system of any one of examples 42-47, wherein the container is a first container, the third line further including a connector having a first end fluidly coupled to the second valve and first container, and a second end fluidly coupled to a third valve and a second container downstream of the third valve.
49. A method for priming a system configured to collect urine from a patient, the method comprising:
    providing the system of any one of examples 42-47;
    infusing fluid from the fluid source through the first valve by regulating the first valve; and
    infusing fluid from the fluid source to the container by regulating the second valve.
50. A method for priming a system configured to collect urine from a patient, the method comprising:
    providing the system of example 48;
    infusing fluid from the fluid source through the first valve by regulating the first valve;

infusing fluid from the fluid source to the first container by regulating the second valve; and infusing fluid from the fluid source to the second container by regulating the third valve.

51. A system for collecting urine from a patient, the system comprising:
    a container configured to collect urine;
    a first sensor configured to obtain a weight of the container;
    a supply line fluidly coupled to the container and configured to receive urine from a patient;
    a second sensor configured to obtain a flow rate of the urine in the supply line; and
    a controller operably coupled to the first sensor and the second sensor.

52. The system of example 51, further comprising a valve operably coupled to the controller and positioned on the supply line between second sensor and the container, wherein the controller is configured to actuate the valve closed if the weight of the container is below a predetermined threshold.

53. The system of example 52, further comprising a reservoir fluidly positioned on the supply line between the second sensor and the valve.

54. A patient treatment system, comprising:
    the system of any one of the examples herein; and
    the device of any one of examples herein.

55. A system for collecting urine from a patient, the system comprising:
    a container configured to collect urine;
    a first sensor configured to generate first sensor data indicative of an amount of urine in the container;
    a second sensor configured to generate second sensor data indicative of the amount of urine in the container;
    one or more processors; and
    one or more non-transitory computer readable media have instructions that, when executed by the one or more processors, cause the system to—
        determine the patient's urine output based at least partially on the first sensor data,
        detect when urine is being emptied from the container, and
        at least while the urine is being emptied from the container, determine the patient's urine output based at least partially on the second sensor data.

56. The system of example 55 wherein the first sensor includes a weight sensor, and wherein the second sensor includes a flow sensor.

57. The system of any of examples 55-56 wherein the first sensor data includes a weight of the container and second sensor data includes a urine flow rate.

58. The system of any of examples 55-57, further comprising a container mounting component operably coupled to the first sensor, wherein the container mounting component is configured to releasably hold the container.

59. The system of example 58 wherein the container mounting component includes a hook configured to suspend the container while the container operably engages the first sensor.

60. The system of any of examples 57-59 wherein the instructions to detect when urine is being emptied from the container include instructions to detect when urine is being emptied from the container based at least partially on a decrease in the weight of the container.

61. The system of example 60 wherein the instructions further include instructions to detect when urine is no longer being emptied from the container.

62. The system of example 61 wherein the instructions to detect when urine is no longer being emptied from the container include instruction to detect when urine is no longer being emptied from the container based at least partially on an increase in the weight of the container.

63. The system of any of examples 55-62, further comprising:
    a urine supply line fluidly coupling the patient and the container; and
    a urine cartridge configured to operably engage at least a portion the urine supply line with the second sensor.

64. The system of example 63 wherein the urine cartridge includes one or more apertures configured to receive at least the portion of the urine supply line.

65. The system of example 63 or example 64 wherein the urine cartridge includes a tab configured to engage the portion of the urine supply line toward at least one of the first sensor or the second sensor.

66. A method for collecting urine from a patient, the method comprising:
    directing, via a flow control assembly, a urine flow from the patient into a container;
    measuring, using a first sensor, an amount of urine within the container;
    detecting, using the first sensor, that urine is being emptied from the container; and
    at least when the urine is draining, measuring, using a second sensor, the patient's urine output.

67. The method of example 66 wherein the first sensor includes a weight sensor, and wherein measuring the amount of urine within the container includes measuring a weight of the container using the weight sensor.

68. The method of any of examples 66-67 wherein the second sensor includes a flow sensor, and wherein measuring the patient's urine output includes measuring a urine flow rate using the second sensor.

69. The method of any of examples 66-68 wherein detecting when urine is being emptied from the container includes detecting when urine is being emptied from the container based at least partially on a decrease in the weight of the container.

70. The method of any of examples 66-69, further comprising detecting when urine is no longer being emptied from the container.

71. The method of example 70 wherein detecting when urine is no longer being emptied from the container includes detecting when urine is no longer being emptied from the container based at least partially on the first sensor.

72. The method of any of examples 70-71 wherein detecting when urine is no longer being emptied from the container includes detecting when urine is no longer being emptied from the container based at least partially on an increase in the weight of the container.

73. A urine collection system, comprising:
    a first sensor configured to generate first sensor data based on a weight of a container positioned to collect urine from a patient;
    a second sensor configured to generate second sensor data based on urine flow from the patient to the container;

one or more processors; and
one or more non-transitory computer readable media having instructions that, when executed by the one or more processors, cause the system to perform operations comprising—
  determining a first patient urine output based on the first sensor data; and
  determining a second patient urine output based on the second sensor data.

74. The system of example 73, wherein the operations further comprise:
  determining, via the first sensor data, that the weight of the container is decreasing; and
  after determining that the weight of the container is decreasing, utilizing the second patient urine output as a primary input,
  wherein the first patient urine output and the second patient urine output are average volumetric flow rates over a period of time.

75. The system of example 74, wherein the operations further comprise, prior to determining that the weight of the container is decreasing, utilizing the first patient urine output as the primary input.

76. The system of example 74, wherein the operations further comprise:
  after determining that the weight of the container is decreasing, determining that the weight of the container is increasing; and
  after determining that the weight of the container is increasing, utilizing the first patient urine output as the primary input.

77. The system of any one of examples 73-76, wherein the operations further comprise:
  utilizing the first patient urine output as a primary input if a difference between the first patient urine output and the second patient urine output is below a predetermined threshold; and
  utilizing the second patient urine output as the primary input if the difference between the first patient urine output and the second patient urine output is not below the predetermined threshold.

78. The system of any one of examples 73-77, further comprising a mounting component operably coupled to the first sensor and configured to support the container positioned to collect urine, wherein the weight of the container is conveyed to the first sensor the mounting component.

79. The system of example 78, further comprising the container including a drain valve, wherein the container is configured to be drained while being supported by the mounting component.

80. The system of example 78, further comprising a console (i) encasing the first sensor and the second sensor and (ii) at least partially defining a recessed area, wherein—
  the mounting component is positioned in the recessed area, and
  the first sensor and the second sensor are above the recessed area.

81. The system of any one of examples 73-80, further comprising:
  a console including (i) a receiving area, and (ii) the second sensor positioned at the receiving area; and
  a urine flow assembly removably attached to the console at the receiving area, such that a portion of the second sensor and a portion of the urine flow assembly together define a slot configured to receive tubing, wherein the tubing is configured to direct urine from the patient to the container.

82. The system of any one of examples 73-81, further comprising:
  a console including (i) a receiving area, and (ii) the second sensor positioned at the receiving area; and
  a urine flow assembly removably attached to the console and including a plurality of ports defining a tubing pathway for directing urine from the patient to the container.

83. The system of any one of examples 73-82, further comprising a pinch valve upstream of the container and positioned to receive tubing configured to direct urine flow from the patient to the container, wherein the pinch valve is configured to regulate urine flow without contacting the urine.

84. A method for collecting urine from a patient, the method comprising:
  measuring, via a first sensor, first sensor data including a weight of a container configured to receive urine flow from a patient;
  generating, via the first sensor data, a first patient urine output;
  determining that the weight of the container is decreasing; and
  after determining that the weight of the container is decreasing, measuring, via a second sensor, second sensor data including a second patient urine output.

85. The method of example 84, further comprising:
  utilizing the first patient urine output if a difference between the first patient urine output and the second patient urine output is below a predetermined threshold; and
  utilizing the second patient urine output if the difference between the first patient urine output and the second patient urine output is not below the predetermined threshold.

86. The method of any one of examples 84-85, further comprising:
  prior to determining that the weight of the container is decreasing, utilizing the first patient urine output as a primary input; and
  after determining that the weight of the container is decreasing, utilizing the second patient urine output as the primary input.

87. The method of example 86, further comprising:
  after determining that the weight of the container is decreasing, determining that the weight of the container is increasing; and
  after determining that the weight of the container is increasing, utilizing the first patient urine output as the primary input.

88. The method of any one of examples 84-87, wherein determining that the weight of the container is decreasing comprises detecting, via the first sensor, that the weight of the container is decreasing.

89. The method of any one of examples 84-88, further comprising directing, via a flow control assembly, urine flow from the patient toward the container.

90. The method of example 89, further comprising, prior to directing the urine flow from the patient toward the container, detecting, via the first sensor, a presence of the container.

91. The method of example 89, wherein:
  the flow control assembly includes a plurality of ports, and tubing extending through the ports to the container, directing the urine flow from the patient toward the container comprises directing the urine flow from the patient toward the container via the tubing, and measuring the second patient urine output comprises measuring the urine flow directed toward the container via the tubing.

92. A fluid therapy system, comprising:
   a first pump configured to provide a diuretic to a patient;
   a second pump configured to provide a hydration fluid to the patient; and
   a urine system including—
      a urine collection device,
      a flow control assembly configured to direct a urine flow from the patient to the urine collection device, and
      a urine measurement device including a first sensor configured to generate first sensor data based on a weight of the container, and a second sensor configured to generate second sensor data based on the urine flow from the patient to the container.

93. The system of example 92, further comprising:
   one or more processors; and
   one or more non-transitory computer readable media having instructions that, when executed by the one or more processors, cause the system to perform operations comprising—
      determining a first patient urine output based on the first sensor data; and
      determining a second patient urine output based on the second sensor data.

94. The system of example 93, the operations further comprising determining an amount of the diuretic to be provided to the patient based on the first patient urine output.

95. The system of example 94, wherein the operations further comprise:
   determining that the weight of the urine collection device is decreasing; and
   after determining that the weight of the container is decreasing, determining the amount of the diuretic to be provided to the patient based on the second patient urine output.

96. The system of example 95, the operations further comprising:
   after determining that the weight of the urine collection device is decreasing, determining that the weight of the urine collection device is increasing; and
   after determining that the weight of the container is increasing, determining the amount of the diuretic to be provided to the patient based on the first patient urine output.

97. The system of any one of examples 92-97, the operations further comprising:
   utilizing the first patient urine output as a primary input if a difference between the first patient urine output and the second patient urine output is below a predetermined threshold; and
   utilizing the second patient urine output as the primary input if the difference between the first patient urine output and the second patient urine output is not below the predetermined threshold.

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although stages of methods may be presented herein in a particular order, alternative embodiments may perform the stages in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing volumes, flow rates, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. When used, the term "about" refers to values within +/−10% of the stated value. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:
1. A fluid therapy system, comprising:
   a urine collection device;
   a fluid line configured to direct urine flow from a patient to the urine collection device; and a urine measurement device including a first sensor configured to generate first sensor data based on an amount of urine in the urine collection device, and a second sensor configured to generate second sensor data based on urine flow from the patient to the urine collection device; and a urine cartridge, wherein the second sensor and the urine cartridge together define opposing sides of a channel that directly receives a portion of the fluid line between the opposing sides, and wherein the second sensor immobilizes the portion of the fluid line.

2. The fluid therapy system of claim 1, further comprising:
a console;
wherein the urine cartridge is configured to be coupled to the console.

3. The fluid therapy system of claim 2, wherein the console has a first side and a second side, and wherein the second sensor is positioned within the console at the first side and the urine cartridge is configured to be coupled to the console at the second side.

4. The fluid therapy system of claim 1, further comprising a first pump configured to provide a diuretic to the patient and a second pump configured to provide a hydration fluid to the patient.

5. The fluid therapy system of claim 1, further comprising:
one or more processors; and
one or more non-transitory computer readable media having instructions that, when executed by the one or more processors, cause the fluid therapy system to perform operations comprising—
determining a first patient urine output based on the first sensor data;
determining a second patient urine output based on the second sensor data; and
determining an amount of a diuretic and/or a hydration fluid to be provided to the patient based, at least in part, on the first patient urine output.

6. The fluid therapy system of claim 5, wherein the operations further comprise:
determining whether the amount of urine in the urine collection device is decreasing; and
after determining whether the amount of urine in the urine collection device is decreasing, determining the amount of the diuretic and/or the hydration fluid to be provided to the patient based, at least in part, on the second patient urine output.

7. The fluid therapy system of claim 6, the operations further comprising:
after determining whether the amount of urine in the urine collection device is decreasing, determining whether the amount of urine in the urine collection device is increasing; and
after determining whether the amount of urine in the urine collection device is increasing, determining the amount of the diuretic and/or the hydration fluid to be provided to the patient based, at least in part, on the first patient urine output.

8. The fluid therapy system of claim 5, the operations further comprising:
if a difference between the first patient urine output and the second patient urine output is below a predetermined threshold, then determining the amount of the diuretic and/or the hydration fluid to be provided to the patient based, at least in part, on the first patient urine output; and if the difference between the first patient urine output and the second patient urine output is not below the predetermined threshold, determining the amount of the diuretic and/or the hydration fluid to be provided to the patient based, at least in part, on the second patient urine output.

9. The fluid therapy system of claim 2 wherein the urine collection device is configured to be suspended from the console, and wherein the urine collection device is operably connected to the first sensor when suspended from the console.

10. The fluid therapy system of claim 1 wherein the urine collection device is a first urine collection device and wherein, when the amount of urine in the first urine collection device exceeds a predetermined threshold, the fluid line is configured to direct the urine flow into a second urine collection device.

11. The fluid therapy system of claim 1 wherein the first sensor is configured to detect (i) a weight of the urine collection device or (ii) a volume of urine in the urine collection device.

12. The fluid therapy system of claim 1 wherein the second sensor is a flow sensor, a thermal flow sensor, or a mechanical flow sensor.

13. A fluid therapy system, comprising:
a urine collection device;
a fluid line configured to direct urine from a patient to the urine collection device; and
a console operably coupled to the urine collection device and the fluid line, wherein the console includes—
a urine measurement device including one or more sensors configured to detect a urine output based on the urine provided from the patient, and
a urine cartridge configured to be releasably coupled to the console;
wherein at least one of the one or more sensors and the urine cartridge together define opposing sides of a channel that receives a portion of the fluid line between the opposing sides, and
wherein the at least one of the one or more sensors immobilizes the portion of the fluid line.

14. The fluid therapy system of claim 13 wherein the urine measurement device is configured to determine a rate of change of a weight of the urine collection device based at least in part on the urine output detected by the one or more sensors.

15. The fluid therapy system of claim 13 wherein the one or more sensors include a first sensor configured to generate first sensor data based on a weight of the urine collection device and a second sensor configured to generate second sensor data based on urine flow to the urine collection device, the system further comprising:
one or more processors; and
one or more non-transitory computer readable media having instructions that, when executed by the one or more processors, cause the system to perform operations comprising:
determining a first patient urine output based on the first sensor data;
determining a second patient urine output based on the second sensor data;
determining, via the first sensor data, a rate of change of a weight of the urine collection device; and
after determining whether the rate of change is less than a predetermined threshold rate, determining an amount of a diuretic and/or a hydration fluid to be provided to the patient based, at least in part, on the second patient urine output.

16. The fluid therapy system of claim 13 wherein the one or more sensors include a first sensor and a second sensor, and wherein the second sensor defines one of the opposing sides of the channel, the console further comprising a mounting component configured to be operably coupled to the first sensor and configured to support the urine collection device positioned to collect urine, wherein a weight of the urine collection device is conveyed to the first sensor via the mounting component.

17. The fluid therapy system of claim 16, wherein the urine collection device includes a drain valve, and wherein the urine collection device is configured to be drained while supported by the mounting component.

18. A fluid therapy system, comprising:
- a urine collection device;
- a fluid line configured to direct urine flow from a patient to the urine collection device; and
- a urine measurement device including a sensor configured to generate sensor data based on urine flow from the patient to the urine collection device; and
- a urine cartridge,
- wherein the sensor and the urine cartridge together define opposing sides of a channel that receives a portion of the fluid line between the opposing sides.

19. The fluid therapy system of claim 18, wherein the sensor is a flow sensor, and wherein the urine measurement device includes a mounting component operably coupled to a weight sensor configured to support the urine collection device and determine a weight of urine within the urine collection device.

* * * * *